US007811998B2

(12) United States Patent
Blagg et al.

(10) Patent No.: US 7,811,998 B2
(45) Date of Patent: Oct. 12, 2010

(54) NOVOBIOCIN ANALOGUES AS ANTICANCER AGENTS

(75) Inventors: Brian S. Blagg, Lawrence, KS (US); Len Neckers, Bethesda, MD (US); Xiao Ming Yu, Beijing (CN)

(73) Assignees: University of Kansas, Lawrence, KS (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/571,899

(22) Filed: Oct. 1, 2009

(65) Prior Publication Data

US 2010/0048882 A1 Feb. 25, 2010

Related U.S. Application Data

(63) Continuation of application No. 11/266,149, filed on Nov. 3, 2005, now Pat. No. 7,608,594.

(60) Provisional application No. 60/624,566, filed on Nov. 3, 2004.

(51) Int. Cl.
*A01N 43/04* (2006.01)
*A61K 31/70* (2006.01)

(52) U.S. Cl. .............................. 514/27; 514/24; 514/25; 514/28; 536/4.1; 536/13

(58) Field of Classification Search ........................ None
See application file for complete search history.

(56) References Cited

U.S. PATENT DOCUMENTS

| 5,382,572 | A | 1/1995 | Afonso et al. |
| 6,579,902 | B1 | 6/2003 | Demassey et al. |
| 7,622,451 | B2 | 11/2009 | Blagg et al. |
| 2007/0270452 | A1 | 11/2007 | Blagg et al. |
| 2009/0163709 | A1 | 6/2009 | Blagg |
| 2009/0187014 | A1 | 7/2009 | Blagg et al. |

FOREIGN PATENT DOCUMENTS

WO WO2006-050501 5/2006

OTHER PUBLICATIONS

International Search Report mailed Apr. 13, 2010 re: PCT/US10/24729.
Lubbers (2005) Thesis paper submitted to the University of Kansas in partial fulfillment for the degree of Masters of Science "Synthetic and computational efforts toward the understanding and development of novobiocin-derived inhibitors of Hsp90".
Donnelly et al. (2008) Curr. Med. Chem. 15(26):2702-2717 "Novobiocin and Additional Inhibitors of the Hsp90 C-Terminal Nucleotide-binding Pocket".
Burlison et al. (2006) J. Am. Chem. Soc. 128(48):15529-15536 (epublished on Nov. 10, 2006) "Novobiocin: redesigning a DNA Gyrase Inhibitor for Selective Inhibition of Hsp90".
Gebhart et al. (1985) Anitimicrobial Agents and Chemotherapy 27(1):55-59 "In Vitro Activities of 47 Antimicrobial Agents Against Three Campylobacter ssp. from Pigs".
Gombert and Aulicino (1984) Antimicrobial Agents and Chemotherapy 26(6):933-934 "Susceptibility of Multiply Antibiotic-Resistant Pneumococci to the New Quinoline Antibiotics, Nalidixic Acid, Coumermycin, and Novobiocin".
Le Bras et al. (2007) Med. Chem. 6189-6200 "New Novobiocin Analogues as Antiproliferative Agents in Breast Cancer Cells and Potential Inhibitors of Heat Shock Protein 90".
Madhavan et al. (2003) Bioorg. Med. Chem. Lett. 13:2547 "Novel Coumarin Derivatives of Heterocyclic Compounds as Lipid Lowering Agents".
Marcu et al. (2000) J. Biol. Chem 275:37181-37186 "The Heat Shock Protein 90 Antagonist Novobiocin Interacts with a Previously Unrecognized ATP-binding Domain in the Carboxy Terminis of the Chaperone".
Messaoudi et al. (2008) Med. Chem. 8:761-782 "Recent Advances in Hsp90 Inhibitors as Antitumor Agents, Anti-Cancer Agents".
Radanyi et al. (2009) Cancer Lett. 274:88-94 "Antiproliferative and Apoptotic Activities of Tosylcylconovobiocic Acids as Potent Heat Shock Protein 90 Inhibitors in Human Cancer Cells".
Radanyi et al. (2008) Biorg. Med. Chem. Lett. 18:2495-2498 "Synthesis and Biological Activity of Simplified Denoviose-Coumarins Related to Novobiocin as Potent Inhibitors of Heat Shock Protein 90 (Hsp90)".
Radanyi et al. (2009) Biochem. Biophys. Res. Comm. 379:514-518 "Tosylcyclonovobiocic Acids Promote Cleavage of the Hsp90-associated Cochaperone p23".
Setlow et al. (1984) J. of Bacteriology 160(2):662-667 "Mechanism of Acquisition of Chromosomal Markers by Plasmids in *Haemophilus influenzae*".
Shen et al. (2004) Bioorganic & Medicinal Chemistry Letters 14:5903-5906 "Syntheses of photolabile novobiocin analogues".
Wells et al. (1971) J. Org. Chem. 36:1503-1506 "Facile synthesis of 3-acylaminoisocoumarins".
Yu et al. (2004) J. Org. Chem. 69:7375-7378 "Synthesis of (-)-Noviose from 2,3-O-Isopropylidene-D-erythronolactol".
Yu et al. (2005) J. Org. Chem. 70:5599-5605 "Synthesis of Mono- and Dihydroxylated Furanoses, Pyranoses, and an Oxepanose for the Preparation of Natural Product Analogue Libraries".
Yu et al. (2005) J. Am. Chem. Soc. 127:12778-12779 "Hsp90 Inhibitors Identified from a Library of Novobiocin Analogues".

*Primary Examiner*—Patrick T Lewis
(74) *Attorney, Agent, or Firm*—Merchant & Gould

(57) ABSTRACT

Novel analogues and derivatives of novobiocin are provided, including compounds having modifications to the amide side chain, coumarin ring, and sugar moieties. The compounds of the present invention are useful as heat shock protein 90 inhibitors, and may be used as anticancer and neuroprotective agents.

18 Claims, 3 Drawing Sheets

NOVOBIOCIN ANALOGUES AS ANTICANCER AGENTS

CROSS-REFERENCE TO RELATED APPLICATIONS

This application is a continuation of U.S. patent application Ser. No. 11/266,149 filed on Nov. 3, 2005, which claims the benefit of U.S. Provisional Application No. 60/624,566 filed on Nov. 3, 2004, each of which is incorporated by reference herein in its entirety.

STATEMENT REGARDING FEDERALLY SPONSORED RESEARCH OR DEVELOPMENT

The present invention was sponsored by the National Institutes of Health COBRE in Protein Structure and Function Grant No. NIH 31207, and the government may have certain rights in the invention.

BACKGROUND OF THE INVENTION

1. Field of the Invention

The present invention is directed to the synthesis and identification of novobiocin analogues useful as a class of anticancer agents and/or neuroprotective agents. The compounds of the present invention act by inhibition of the Hsp90 protein-folding machinery.

2. Description of Related Art

The 90 kDa heat shock proteins ("Hsp90") belong to a family of chaperones that regulate intracellular functions and are required for the refolding of denatured proteins following heat shock, as well as the conformational maturation of a large number of key proteins involved in cellular processes. The Hsp90 family of chaperones is comprised of four different isoforms. Hsp90α (inducible/major form) and Hsp90β (constitutive/minor form) are found predominately in the cytosol, the 94-kDa glucose-regulated protein ("GRP94") is localized to the endoplasmic reticulum, and Hsp75/tumour necrosis factor receptor associated protein 1 ("TRAP-1") resides mainly in the mitochondrial matrix. These Hsp90s bind to client proteins in the presence of cochaperones, immunophilins, and partner proteins to make the multiprotein complex responsible for conformational maturation of newly formed nascent peptides into biologically active three-dimensional structures.

As discussed more fully below, Hsp90 is an ATP-dependent protein with an ATP binding site in the N-terminal region of the active homodimer. Disruption of the ATPase activity of Hsp90 results in the destabilization of multiprotein complexes and subsequent ubiquitination of the client protein, which undergoes proteasome-mediated hydrolysis. More specifically, in an ATP-dependent fashion, Hsp70 binds to newly synthesized proteins cotranslationally and/or post-translationally to stabilize the nascent peptide by preventing aggregation. Stabilization of the Hsp70/polypeptide binary complex is dependent upon the binding of Hsp70 interacting protein ("HIP"), which occurs after Hsp70 binds to the newly formed peptide. Hsp70-Hsp90 organizing protein ("HOP") contains highly conserved tetratricopeptide repeats ("TPRs") that are recognized by both Hsp70 and Hsp90, promoting the union of Hsp70/HIP and Hsp90, which results in a heteroprotein complex. In the case of telomerase and steroid hormone receptors, the client protein is transferred from the Hsp70 system to the Hsp90 homodimer with concomitant release of Hsp70, HIP, and HOP. Upon binding of ATP and an immunophilin with cis/trans peptidyl prolyl-isomerase activity (FKBP51, FKBP52, or CyPA), the ensemble folds the client protein into its three-dimensional structure. In a subsequent event, p23 binds Hsp90 near the N-terminal region promoting the hydrolysis of ATP and release of the folded protein, Hsp90 partner proteins, and ADP.

Examples of proteins dependent upon Hsp90 for conformational maturation include oncogenic and cellular Src kinases (v-Src, Hck, Lck), Raf, p185, mutant p53 (not normal p53), telomerase, steroid hormone receptors, polo-like kinase ("PLK"), protein kinase B ("AKT"), death domain kinase ("RIP"), MET kinase, focal adhesion kinase ("FAK"), aryl hydrocarbon receptor, RNA-dependent protein kinase ("PKR"), nitric oxide synthase ("NOS"), centrosomal proteins, PI3 kinases, androgen receptor ("AR"), matrix metalloproteinase-2 ("MMP2") and others. In addition, other proteins, such as cyclin dependent kinase 4 ("CDK4"), cyclin dependent kinase 6 ("CDK6"), estrogen receptor, human epidermal growth factor receptor 2 ("Her-2" or "erbB2") are thought to be client proteins of Hsp90. Of these Hsp90 client proteins, Raf, PLK, RIP, AKT, FAK, telomerase, HER-2, and MET kinase are directly associated with the six hallmarks of cancer: (1) self-sufficiency in growth signals; (2) insensitivity to antigrowth signals; (3) evasion of apoptosis; (4) unlimited replication potential; (5) sustained angiogenesis; and (6) tissue invasion/metastasis. Consequently, Hsp90 is a target for the development of cancer therapeutics because multiple signaling pathways can be simultaneously inhibited by disruption of the Hsp90 protein folding machinery.

Hsp90 contains two nucleotide-binding sites: the N-terminal ATP binding site is the region to which geldanamycin ("GDA"), 17-(allylamino)-17-demethoxygeldanamycin ("17-AAG"), herbimycin A ("HB"), and radicicol bind (see Roe et al., Structural Basis for Inhibition of the Hsp90 Molecular Chaperone by the Antitumor Antibiotics Radicicol and Geldanamycin, *J. Med. Chem.* 1999, 42, 260-266) and the C-terminus, which was recently shown to bind novobiocin (see Marcu et al., The Heat Shock Protein 90 Antagonist Novobiocin Interacts with a Previously Unrecognized ATP-binding Domain in the Carboxy Terminis of the Chaperone, *J. Biol. Chem.* 2000, 276, 37181).

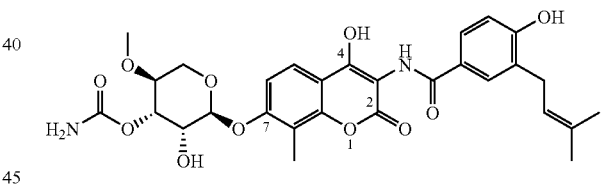

Novobiocin

The C-terminal portion of Hsp90 is required for dimerization and represents a promising target for inhibitors. Unfortunately, the ability of novobiocin to cause degradation of Hsp90 clients is relatively weak (about 700 μM in SKBr3 breast cancer cells). Thus, there remains a need to develop other Hsp90 inhibitors as useful anti-cancer agents. Most preferably, these new Hsp90 inhibitors have decreased toxicity, increased solubility, and/or increased selectivity for Hsp90.

It is also contemplated that the Hsp90 inhibitors of the present invention will be useful as neuroprotective agents. The accumulation of protein aggregates within or outside neurons is a common characteristic of the two most common age-related neurodegenerative diseases, Alzheimer's disease, with plaques enriched in β-amyloid peptides ("Aβ") and neurofibrillary tangles ("NFTs") containing hyperphosphorylated Tau protein, and Parkinson's disease ("PD") with Lewy bodies composed primarily of fibrillar α-synuclein. However, even less frequent but equally debilitating nervous system diseases such as Huntington's disease, amyotrophic lateral sclerosis ("ALS"), prion diseases, and the tauopathies also share the characteristic of aggregated protein deposits. A growing body of evidence now indicates that strategies that promote either refolding or degradation of hyperphosphorylated Tau enhance cell survival in the presence of over-expressed Tau or mutant human Tau. See, e.g., Shimura et al., Binding of Tau to heat shock protein 27 leads to decreased concentration of hyperphosphorylated tau and enhanced cell survival, *J. Biol. Chem.*, 2004, 279:17957-17962; Dou et al., Chaperones increase association of Tau protein with microtubules, *Proc. Natl. Acad. Sci. USA,* 2003, 100:721-726; Kosik & Shimura, Phosphorylated tau and the neurodegenerative foldopathies, *Biochim. Biophys. Acta.*, 2005, 1739: 298-310; Shimura et al., CHIP-Hsc70 complex ubiquitinates phosphorylated tau and enhances cell survival, *J. Biol. Chem.*, 2005 279:4869-4876. Such observations suggest that the cellular machinery needed for removal of misfolded proteins may be compromised in neurodegenerative diseases.

More specifically, the interaction of Hsp90 with cochaperones that regulate cell-specific responses to stress has led to the identification of Hsp90 and the cochaperones Hsp70 and CHIP (carboxy-terminus of the Hsp70-interacting protein) as strong candidates in determining the fate of neuronal protein aggregates. This has been most clearly demonstrated in the case of the hyperphosphorylated Tau protein in NFTs in Alzheimer's disease and the "tauopathies" due to mutations in the tau gene. Low concentrations of Hsp90 inhibitors appear to up-regulate expression of Hsp90 and co-chaperones that decrease aggregated Tau and increase neuronal survival. However, most of the known Hsp90 inhibitors are toxic to many cell types, limiting their potential for chronic use to delay the progression of neurodegenerative diseases. Thus, there remains a need to develop other Hsp90 inhibitors as useful neuroprotective agents.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF SUMMARY OF THE INVENTION

The present invention is directed to novel compounds useful as Hsp90 inhibitors, and in particular as anti-cancer an neuroprotective agents.

In one aspect, the invention encompasses compounds according to Formula I

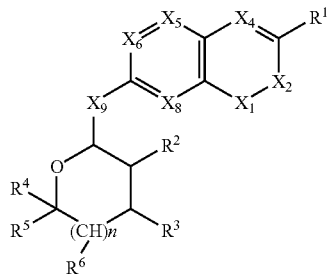

wherein $R^1$ is hydrogen, alkyl, alkenyl, alkynyl, carbocyclic, heterocyclic, aryl, aralkyl, carboxyl, amido, amino, sulfanyl, sulfenyl, sulfonyl, or ether; or $R^1$ together with $X^2$ and the atom to which $R^1$ is attached form a heterocyclic ring having 4 to 8 ring members with at least one heteroatom selected from oxygen or nitrogen; or $R^1$ together with $X^4$ and the atom to which $R^1$ is attached form a heterocyclic ring having 4 to 8 ring members with at least one heteroatom selected from oxygen or nitrogen;

wherein $R^2$ is hydrogen, hydroxy, or $-R^5-OR^9$, wherein $R^8$ is a covalent bond or alkyl, and $R^9$ is C-amido or acyl; or $R^2$ together with $R^3$ and the atoms to which they are attached form a heterocyclic ring having 4 to 8 ring members with at least one heteroatom selected from oxygen or nitrogen;

wherein $R^3$ is hydrogen, hydroxy, or $-R^{10}-O-R^{11}$, wherein $R^{10}$ is a covalent bond or alkyl, and $R^{11}$ is C-amido or acyl; or $R^3$ together with $R^2$ and the atoms to which they are attached form a heterocyclic ring having 4 to 8 ring members with at least one heteroatom selected from oxygen or nitrogen;

wherein $R^4$ is hydrogen, hydroxy, carboxyl, $-R^{12}-O-R^{13}$, or $-R^{12}-R^{14}$; and wherein $R^{12}$ is a covalent bond or alkyl, and $R^{13}$ is C-amido or acyl, and $R^{14}$ is N-amido, $-POR^{15}R^{16}-SO_2R^{17}$, or sulfonamido, and wherein $R^{15}$, $R^{16}$, $R^{17}$ are independently alkoxy;

wherein $R^5$ is hydrogen, alkyl, alkenyl, alkynyl, aryl, or aralkyl;

wherein $R^6$ is hydrogen, alkyl, alkenyl, alkynyl, aryl, aralkyl, alkoxy, aryloxy or aralkoxy;

wherein $X_1$ is $-O-$, $-CO-$, or $-N-$;

wherein $X_2$ is $-O-$, $-N-$, $-NR^{18}-$, $-CR^{19}-$, or $-CO-$; and wherein $R^{18}$ and $R^{19}$ are hydrogen, alkyl, alkenyl, or alkynyl; or $X_2$ together with $R^1$ and the atom to which $R^1$ is attached form a heterocyclic ring having 4 to 8 ring members with at least one heteroatom selected from oxygen or nitrogen;

wherein $X_4$ is $-O-$, $-CR^{20}-$, $-CO-$, or $-N-$, wherein $R^{20}$ is hydrogen, alkyl, alkenyl, alkynyl, or hydroxy; or wherein $X_4$ together with $R^1$ and the atoms to which they are attached form a heterocyclic ring having 4 to 8 ring members with at least one heteroatom selected from oxygen or nitrogen;

wherein $X_5$, is $-CR^{21}-$ or $-N-$, wherein $R^{21}$ is hydrogen, alkyl, alkenyl, or alkynyl;

wherein $X_6$, is $-CR^{22}-$ or $-N-$, wherein $R^{22}$ is hydrogen, alkyl, alkenyl, alkynyl, alkoxy, aryl, aralkyl, halogen, or nitro; or $X_6$ together with $X_9$ and the carbon at position 7 form a heterocylic ring having 4 to 8 ring members with at least one heteroatom selected from oxygen or nitrogen;

wherein $X_8$, is $-CR^{23}-$ or $-N-$, wherein $R^{23}$ is hydrogen, alkyl, alkenyl, or alkynyl;

wherein $X_9$ is alkyl, alkenyl, alkynyl, ether, secondary or tertiary amino, or sulfanyl; or $X_9$ together with $X_6$ and the carbon at position 7 form a heterocyclic ring having 4 to 8 ring members with at least one heteroatom selected from oxygen or nitrogen;

wherein at least one of $X_1$, $X_2$, $X_4$, $X_5$, $X_6$, $X_8$ is not $-CR-$; and wherein n is 0, 1, 2, or 3.

In still another aspect, the present invention is directed to compounds of Formula I that are coumarin compounds wherein $X_1$ is $-O-$ and $X_2$ is $-CO-$.

In still another aspect, the present invention is directed to compounds of Formula I that are isocoumarin compounds wherein $X_1$ is $-CO-$ and $X_2$ is $-O-$.

In still a further aspect, the present invention is directed to des(dimethyl) derivatives and analogues of novobiocin in which $R^4$ and $R^5$ are both hydrogen.

In still another aspect, the present invention is directed to desmethoxy derivatives and analogues of novobiocin in which $R^6$ is hydrogen.

In yet another aspect, the present invention is directed to compounds according to the Formula I(F):

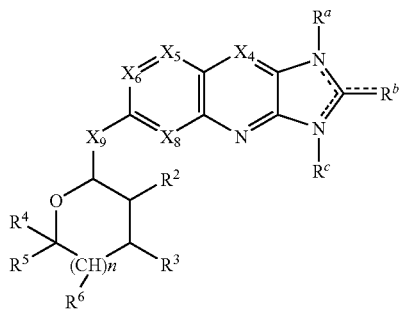

wherein $X_4$, $X_5$, $X_6$, $X_8$, $X_9$, $R^2$, $R^3$, $R^4$, $R^5$, $R^6$, and n are defined as set forth above, and wherein $R^a$, $R^b$ and $R^c$ are independently hydrogen, alkyl, alkenyl, alkynyl, carbocyclic, heterocyclic, aryl, or aralkyl; and wherein $R^b$ may also be oxidized to form a carbonyl.

In still another aspect, the invention encompasses compounds according to the Formula I(F)(i):

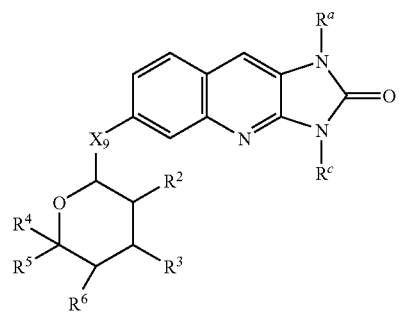

wherein $X_9$, $R^2$, $R^3$, $R^4$, $R^5$, and $R^6$ are defined as set forth above, and wherein $R^a$ and $R^c$ are independently hydrogen, alkyl, alkenyl, alkynyl, carbocyclic, heterocyclic, aryl, or aralkyl.

In still another aspect, the present invention is directed to compounds according to the Formula I(F)(ii):

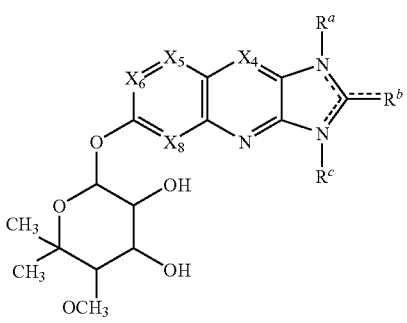

wherein $X_4$, $X_5$, $X_6$, and $X_8$ are defined as set forth above, and wherein $R^a$, $R^b$ and $R^c$ are independently hydrogen, alkyl, alkenyl, alkynyl, carbocyclic, heterocyclic, aryl, or aralkyl; and wherein $R^b$ may also be oxidized to form a carbonyl.

In still another aspect, the present invention is directed to compounds encompassed by the Formula I(F)(iii):

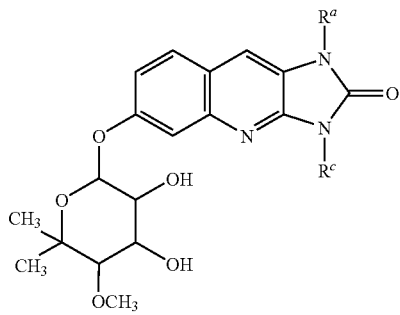

In yet another aspect, the present invention is directed to compounds according to the Formula I(G):

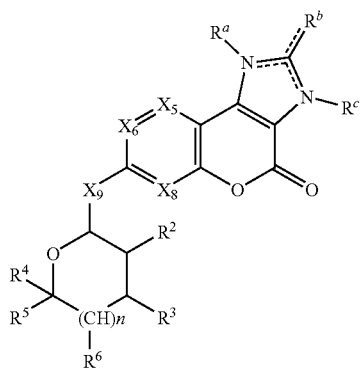

wherein $X_5$, $X_6$, $X_8$, $X_9$, $R^2$, $R^3$, $R^4$, $R^5$, $R^6$, and n are defined as set forth above, and wherein $R^a$, $R^b$ and $R^c$ are independently hydrogen, alkyl, alkenyl, alkynyl, carbocyclic, heterocyclic, aryl, or aralkyl; and wherein $R^b$ may also be oxidized to form a carbonyl.

In a further aspect, the present invention is directed to compounds according to the Formula I(G)(i):

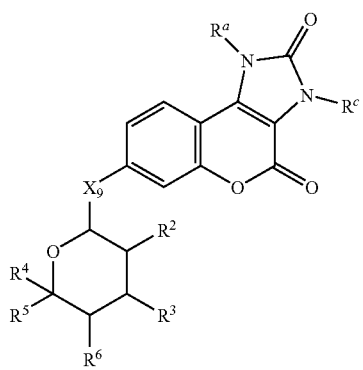

wherein $X_9$, $R^2$, $R^3$, $R^4$, $R^5$, $R^6$ are defined as set forth above, and wherein $R^a$ and $R^c$ are independently hydrogen, alkyl, alkenyl, alkynyl, carbocyclic, heterocyclic, aryl, or aralkyl.

In yet another aspect, the present invention is directed to compounds according to Formula I(G)(ii):

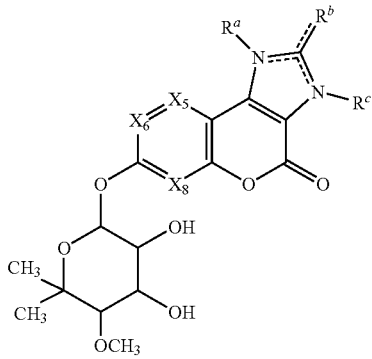

wherein $X_5$, $X_6$, and $X_8$ are defined as set forth above, and wherein $R^a$, $R^b$ and $R^c$ are independently hydrogen, alkyl, alkenyl, alkynyl, carbocyclic, heterocyclic, aryl, or aralkyl; and wherein $R^b$ may also be oxidized to form a carbonyl.

In still a further aspect, the present invention is directed to compounds according to Formula I(G)(iii):

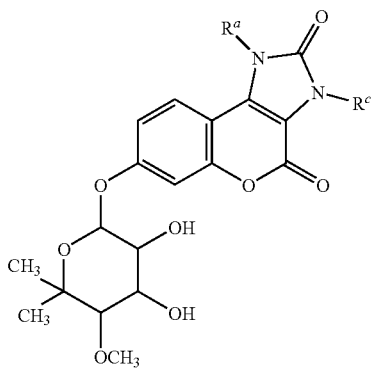

In a further aspect, the present invention is directed to compounds according to Formula I(H):

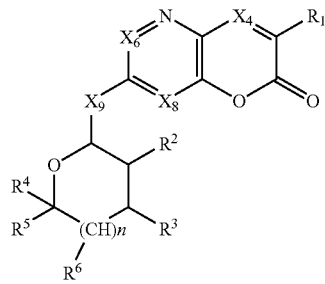

wherein $X_4$, $X_6$, $X_8$, $X_9$, $R^1$, $R^2$, $R^3$, $R^4$, $R^5$, $R^6$, and n are defined as set forth above.

In still a further aspect, the invention comprises compounds according to the Formula I(H)(i):

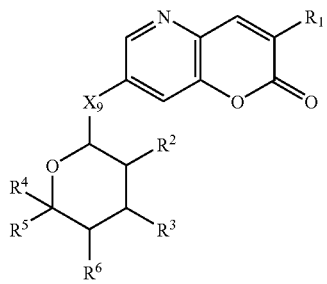

wherein $X_9$, $R^1$, $R^2$, $R^3$, $R^4$, $R^5$, and $R^6$ are defined as set forth above.

In still another aspect, the present invention is directed to compounds according to Formula I in which $R^2$ and $R^3$ form a cyclic carbonate.

In still another aspect, the present invention is directed to compounds according to Formula I in which the sugar ring is modified to include a diol at $R^2$ and $R^3$.

In still another aspect, the present invention is directed to compounds according to Formula I in which sugar is modified to include a 2'-carbamate at $R^2$.

In still another aspect, the present invention is directed to the compounds of Formula I in which the coumarin ring is modified to include a lower alkoxy or nitro substitution at the 6-position of the coumarin ring.

In a further aspect, the present invention encompasses compounds according to Formula I(J):

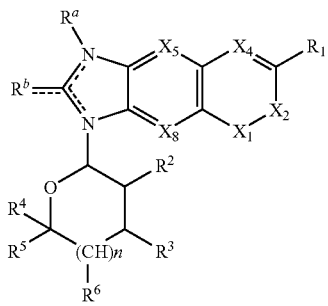

wherein $X_1$, $X_2$, $X_4$, $X_5$, $X_8$, $R^1$, $R^2$, $R^3$, $R^4$, $R^5$, $R^6$, and n are defined as set forth above; and wherein $R^a$ and $R^b$ are independently hydrogen, alkyl, alkenyl, alkynyl, carbocyclic, heterocyclic, aryl, or aralkyl; and wherein $R^b$ may also be oxidized to form a carbonyl.

In still a further aspect, the present invention is directed to compounds according Formula I(J)(i):

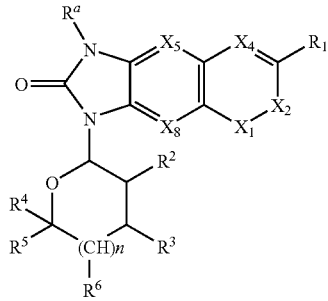

wherein $X_1$, $X_2$, $X_4$, $X_5$, $X_8$, $R^1$, $R^2$, $R^3$, $R^4$, $R^5$, $R^6$, n, and $R^a$ are defined as set forth above.

In still a further aspect, the present invention is directed to compounds according to the Formula I(J)(ii):

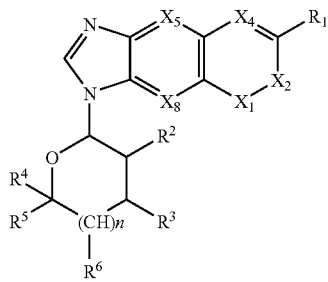

wherein $X_1$, $X_2$, $X_4$, $X_5$, $X_8$, $R^1$, $R^2$, $R^3$, $R^4$, $R^5$, $R^6$, n, and $R^a$ are defined as set forth above.

In still another aspect, the present invention is directed to compounds encompassed by Formula I(K):

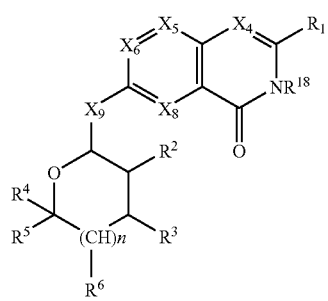

wherein $X_4$, $X_5$, $X_6$, $X_8$, $X_9$, $R^1$, $R^2$, $R^3$, $R^4$, $R^5$, $R^6$, and n are defined as set forth above; and wherein $R^{18}$ is hydrogen, alkyl, alkenyl, or alkynyl.

In yet another aspect, the present invention is directed to compounds encompassed by Formula I(K)(i):

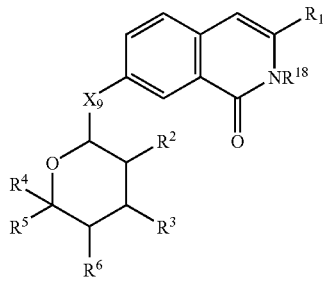

wherein $X_9$, $R^1$, $R^2$, $R^3$, $R^4$, $R^5$, and $R^6$ are defined as set forth above; and wherein $R^{18}$ is hydrogen, alkyl, alkenyl, or alkynyl.

In still a further aspect, the present invention is directed to 4-deshydroxy derivatives and analogues of novobiocin in which $X_4$ is —$CR^{20}$— and $R^{20}$ is hydrogen.

In yet a further aspect, the present invention is directed to 8-desmethyl derivatives and analogues of novobiocin in which $X_8$ is —$CR^{22}$— and $R^{22}$ is hydrogen.

In still another aspect, the present invention encompasses compounds according to the Formula I(L):

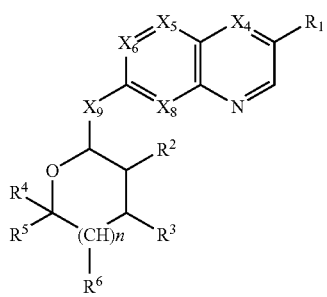

wherein $X_4$, $X_5$, $X_6$, $X_8$, $X_9$, $R^1$, $R^2$, $R^3$, $R^4$, $R^5$, $R^6$, and n are defined as set forth above.

In yet another aspect, the present invention is directed to compounds according Formula I(L)(i):

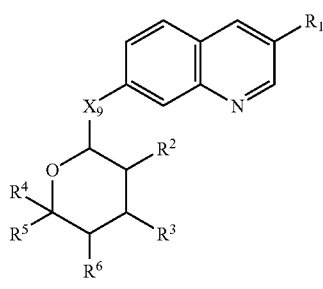

wherein $X_9$, $R^1$, $R^2$, $R^3$, $R^4$, $R^5$, $R^6$, and n are defined as set forth above.

In still another aspect of the present invention, the novobiocin derivatives and analogues of the present invention are modified so that the sugar is modified as set forth below:

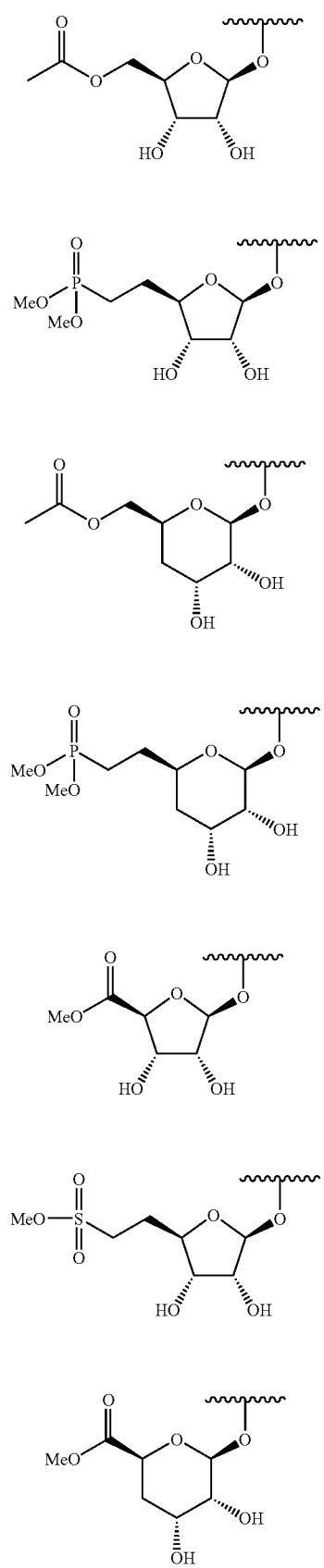
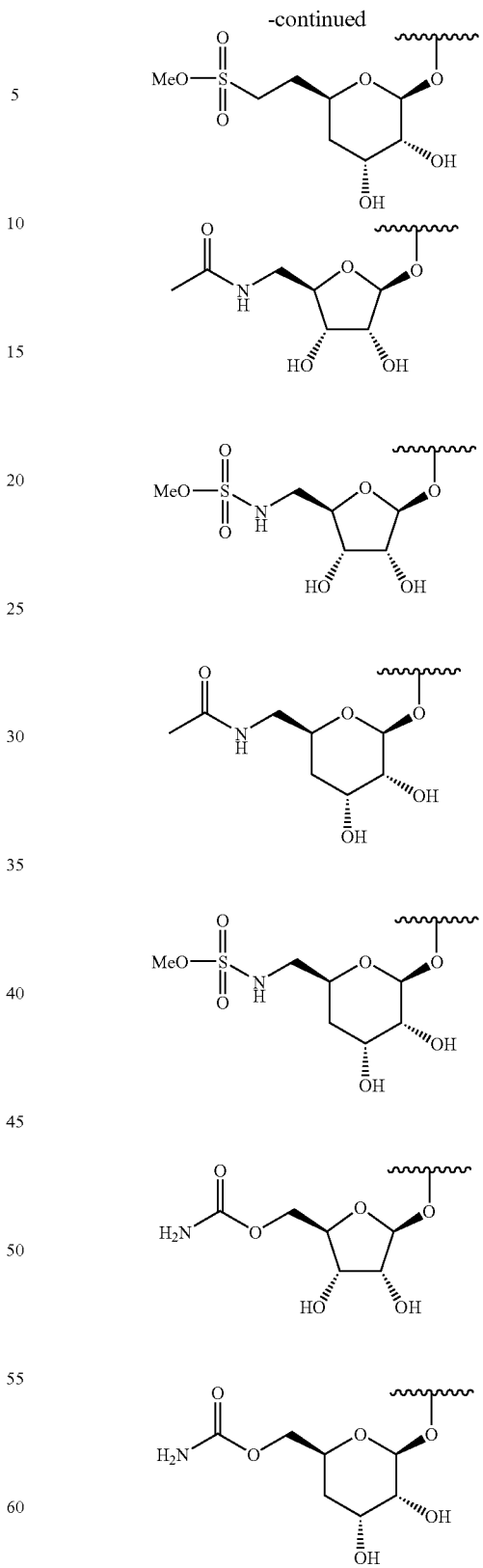
In still another aspect, the present invention is directed to dimers of the foregoing compounds. In particular, exemplary dimers are provided by the formula:

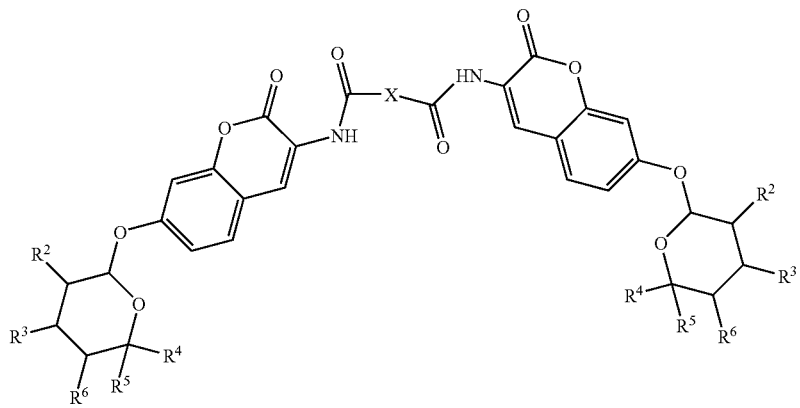

wherein X is alkyl, alkenyl, alkynyl, aryl, alkylaryl, carbocyclic or heterocyclic; and wherein $R^2$, $R^3$, $R^4$, $R^5$, and $R^6$ are set forth above.

In another aspect, the present invention comprises the in which the linker is a heterocylic pyrrole as shown below:

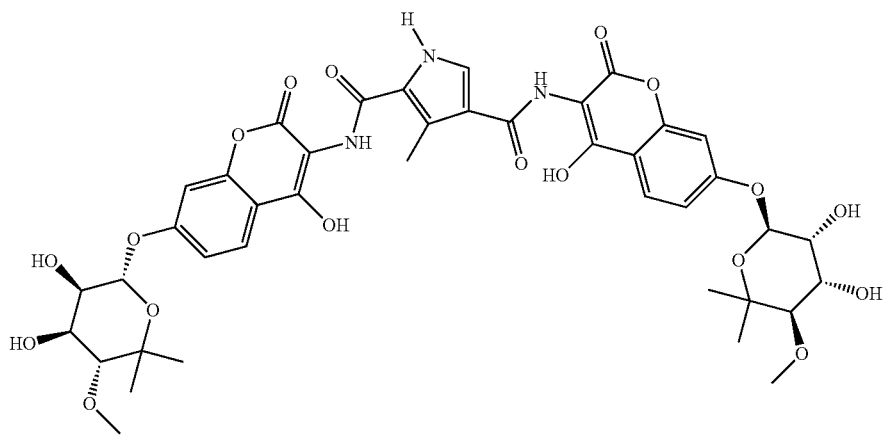

It is contemplated that one or more compounds of the present invention will be useful for inhibiting heat-shock protein 90 activity by administering one of more of the compounds of the present invention to a cell or subject and observing a decrease in the expression of a heat-shock protein 90 client protein.

According to another aspect, the present invention provides a pharmaceutical composition, which comprises a therapeutically-effective amount of one or more compounds of the present invention or a pharmaceutically-acceptable salt, ester or prodrug thereof, together with a pharmaceutically-acceptable diluent or carrier.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
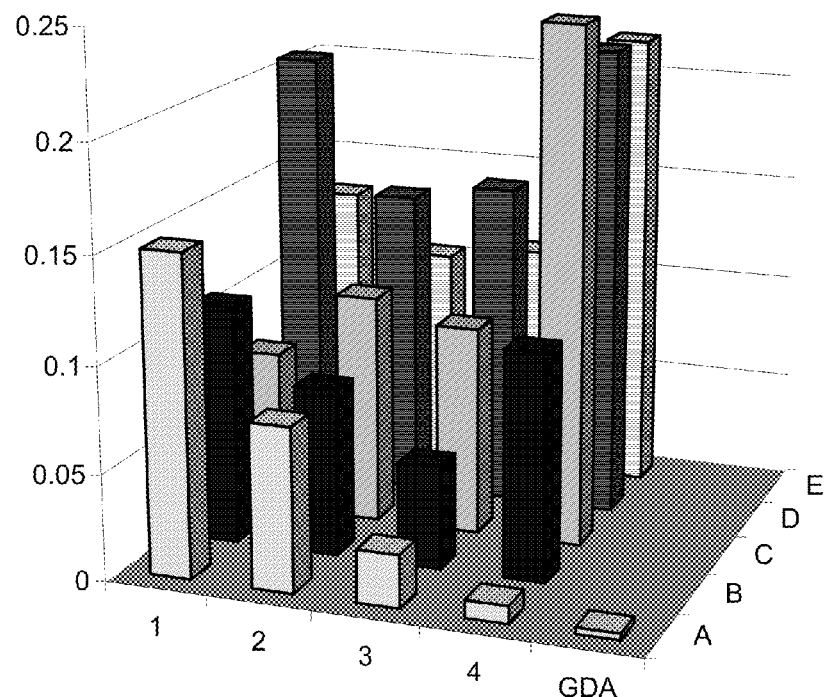
FIG. 1 shows the relative ratios of phospho-AKT by Western blot analyses when the compounds of Example 1 were tested for their ability to inhibit Hsp90 in Skbr3 breast cancer cells. Total protein concentration of each lysate was determined and equal amounts of protein were run in each lane of the gels. For the graphs shown in FIG. 1, the O.D.'s (optical density) of the Western bands for phospho-AKT were measured, as were the O.D.'s for actin probed as controls on the same blots. To obtain the graphed values, all specific O.D.'s (for Hsp90 clients) were normalized to the respective actin O.D.

Molecular terms, when used in this application, have their common meaning unless otherwise specified. It should be noted that the alphabetical letters used in the formulas of the present invention should be interpreted as the functional groups, moieties, or substitutents as defined herein. Unless otherwise defined, the symbols will have their ordinary and customary meaning to those skilled in the art.

The term "acyl" refers to —COR wherein R used in this definition is hydrogen, alkyl, alkenyl, alkynyl, carbocyclic, heterocylic, aryl, or aralkyl. Most preferably, R is hydrogen, alkyl, aryl, or aralkyl.

The term "amido" indicates either a C-amido group such as —CONR'R" or an N-amido group such as —NR'COR" wherein R' and R" as used in this definition are independently hydrogen, alkyl, alkenyl, alkynyl, alkoxy, carbocyclic, heterocylic, aryl, or aralkyl. A "sulfoamido" group includes the —NR'—SO$_2$—R". Most preferably, R' and R" are hydrogen, alkyl, aryl, or aralkyl.

The term "amino" signifies a primary, secondary or tertiary amino group of the formula —NR'R" wherein R' and R" as used in this definition are independently hydrogen, alkyl, alkyenyl, alkynyl, aralkyl, carbocyclic, heterocyclic, aralkyl, or other amino (in the case of hydrazide) or R' and R" together with the nitrogen atom to which they are attached, form a ring having 4-8 atoms. Thus, the term "amino", as used herein, includes unsubstituted, monosubstituted (e.g., monoalkylamino or monoarylamino), and disubstituted (e.g., dialkylamino or aralkylamino) amino groups. Amino groups include —NH$_2$, methylamino, ethylamino, dimethylamino, diethylamino, methyl-ethylamino, pyrrolidin-1-yl or piperidino, morpholino, etc. Other exemplary "amino" groups forming a ring include pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolizinyl. The ring containing the amino group may be optionally substituted with another amino, alkyl, alkenyl, alkynyl, halo, or hydroxyl group.

The term "alkyl" refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred "alkyl" groups herein contain 1 to 12 carbon atoms. Most preferred are "lower alkyl" which refer to an alkyl group of one to six, more preferably one to four, carbon atoms. The alkyl group may be optionally substituted with an amino, alkyl, halo, or hydroxyl group.

The term "alkoxy" denotes oxy-containing groups substituted with an alkyl, or cycloalkyl group. Examples include, without limitation, methoxy, ethoxy, tert-butoxy, and cyclohexyloxy. Most preferred are "lower alkoxy" groups having one to six carbon atoms. Examples of such groups include methoxy, ethoxy, propoxy, butoxy, isopropoxy, and tert-butoxy groups.

The terms "alkenyl" and "alkynyl" refer to unsaturated aliphatic groups analogous in length and possible substitution to the alkyls described above, but that contain at least one double bond or triple bond respectively.

The term "aryl" means a carbocyclic aromatic system containing one, two or three rings wherein such rings may be attached together in a pendant manner or may be fused. The term "fused" means that a second ring is present (i.e., attached or formed) by having two adjacent atoms in common (i.e., shared) with the first ring. The term "fused" is equivalent to the term "condensed." The term "aryl" embraces aromatic groups such as phenyl, naphthyl, tetrahydronaphthyl, indane, and biphenyl. The aryl group may optionally be substituted with an amino, alkyl, halo, hydroxyl, carbocyclic, heterocyclic, or another aryl group.

The term "aralkyl" embraces aryl-substituted alkyl moieties. Preferable aralkyl groups are "lower aralkyl" groups having aryl groups attached to alkyl groups having one to six carbon atoms. Examples of such groups include benzyl, diphenylmethyl, triphenylmethyl, phenylethyl, and diphenylethyl. The terms benzyl and phenylmethyl are interchangeable.

The term "aryloxy" embraces aryl groups, as defined above, attached to an oxygen atom. The aryloxy groups may optionally be substituted with a halo, hydroxyl, or alkyl group. Examples of such groups include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy)phenoxy.

The term "aralkoxy" embraces oxy-containing aralkyl groups attached through an oxygen atom to other groups. "Lower aralkoxy" groups are those phenyl groups attached to lower alkoxy group as described above. Examples of such groups include benzyloxy, 1-phenylethoxy, 3-trifluoromethoxybenzyloxy, 3-trifluoromethylbenzyloxy, 3,5-difluorobenzyloxy, 3-bromobenzyloxy, 4-propylbenzyloxy, 2-fluoro-3-trifluoromethylbenzyloxy, and 2-phenylethoxy.

The term "carboxyl" refers to —R'C(=O)OR", wherein R' and R" as used in this definition are independently hydrogen, alkyl, alkenyl, alkynyl, carbocyclic, heterocylic, aryl, or aralkyl or R' can additionally be a covalent bond. "Carboxyl" includes both carboxylic acids, and carboxylic acid esters. The term "carboxylic acid" refers to a carboxyl group in which R" is hydrogen. Such acids include formic, acetic, propionic, butyric, valeric acid, 2-methyl propionic acid, oxirane-carboxylic acid, and cyclopropane carboxylic acid. The term "carboxylic acid ester" or "ester" refers to a carboxyl group in which R" is alkyl, alkenyl, alkynyl, carbocyclic, heterocylic, aryl, or aralkyl.

The term "carbocyclic" refers to a group that contains one or more covalently closed ring structures, and that the atoms forming the backbone of the ring are all carbon atoms. The ring structure may be saturated or unsaturated. The term thus distinguishes carbocyclic from heterocyclic rings in which the ring backbone contains at least one non-carbon atom. The term carbocylic encompasses cycloalkyl ring systems.

The terms "cycloalkane" or "cyclic alkane" or "cycloalkyl" refer to a carbocyclic group in which the ring is a cyclic aliphatic hydrocarbon, for example, a cyclic alkyl group preferably with 3 to 12 ring carbons. "Cycloalkyl" includes, by way of example, cyclopropyl, cyclobutyl, cyclopentyl, cyclohexyl, cycloheptyl, or cyclooctyl, and the like.

The cycloalkyl group may be optionally substituted with an amino, alkyl, halo, or hydroxyl group.

The term "ether" refers to the group —R'—O—R" wherein R' and R" as used in this definition are independently hydrogen, alkyl, alkenyl, alkynyl, carbocyclic, heterocylic, aryl, or aralkyl, and R' can additionally be a covalent bond attached to a carbon.

The terms "halo" or "halogen" refer to fluoro, chloro, bromo or iodo, usually regarding halo substitution for a hydrogen atom in an organic compound.

The term "heterocyclic or heterocycle" means an optionally substituted, saturated or unsaturated, aromatic or non-aromatic cyclic hydrocarbon group with 4 to about 12 carbon atoms, preferably about 5 to about 6, wherein 1 to about 4 carbon atoms are replaced by nitrogen, oxygen or sulfur. Exemplary heterocyclic which are aromatic include groups pyridinyl, furanyl, benzofuranyl, isobenzofuranyl, pyrrolyl, thienyl, 1,2,3-triazolyl, 1,2,4-triazolyl, indolyl, imidazolyl, thiazolyl, thiadiazolyl, pyrimidinyl, oxazolyl, triazinyl, and tetrazolyl. Exemplary heterocycles include benzimidazole, dihydrothiophene, dioxin, dioxane, dioxolane, dithiane, dithiazine, dithiazole, dithiolane, furan, indole, 3-H indazole, 3-H-indole, imidazole, indolizine, isoindole, isothiazole, isoxazole, morpholine, oxazole, oxadiazole, oxathiazole, oxathiazolidine, oxazine, oxadiazine, piperazine, piperidine, purine, pyran, pyrazine, pyrazole, pyridine, pyrimidine, pyrimidine, pyridazine, pyrrole, pyrrolidine, tetrahydrofuran, tetrazine, thiadiazine, thiadiazole, thiatriazole, thiazine, thiazole, thiomorpholine, thiophene, thiopyran, triazine, and triazole. The heterocycle may be optionally substituted with an amino, alkyl, alkenyl, alkynyl, halo, hydroxyl, carbocyclic, thio, other heterocyclic, or aryl group. Exemplary heterocyclic groups include 1-pyrrolyl, 2-pyrrolyl, 3-pyrrolyl, 1-indolyl, 2-indolyl, 3-indolyl, 1-pyridyl, 2-pyridyl, 3-pyridyl, 4-pyridyl, 1-imidazolyl, 2-imidazolyl, 3-imidazolyl, 4-imidazolyl, 1-pyrazolyl, 2 pyrazolyl, 3-pyrazolyl, 4-pyrazolyl, 5-pyrazolyl, 1-pyrazinyl, 2-pyrazinyl, 1-pyrimidinyl, 2-pyrimidinyl, 4-pyrimidinyl, 5-pyrimidinyl, 1-pyridazinyl, 2-pyridazinyl, 3-pyridazinyl, 4-pyridizinyl, 1-indolizinyl, 2-indolizinyl, 3-indolizinyl, 4-indolizinyl, 5-indolizinyl, 6-indolizinyl, 7-indolizinyl, 8-indolizinyl, 1-isoindolyl, 2-isoindolyl, 3-isoindolyl, 4-isoindolyl, 5-isoindolyl.

The term "hydroxy" or "hydroxyl" refers to the substituent —OH.

The term "oxo" shall refer to the substituent =O.

The term "nitro" means —NO$_2$.

The term "sulfanyl" refers to —SR' where R' as used in this definition is hydrogen, alkyl, alkenyl, alkynyl, carbocyclic, heterocyclic, aryl, or aralkyl.

The term "sulfenyl" refers to —SOR' where R' as used is this definition is hydrogen, alkyl, alkenyl, alkynyl, carbocyclic, heterocyclic, aryl, or aralkyl.

The term "sulfonyl" refers to —SOR' where R' as used in this definition is hydrogen, alkyl, alkenyl, alkynyl, carbocyclic, heterocyclic, aryl, or aralkyl.

"Optional" or "optionally" means that the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution. "Optionally" is inclusive of embodiments in which the described conditions is present and embodiments in which the described condition is not present.

The compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention.

Also included in the family of compounds of the present invention are the pharmaceutically acceptable salts, esters, and prodrugs thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the present invention be prepared from inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, aralphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of the present invention include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compounds of by reacting, for example, the appropriate acid or base with the compounds of the present invention.

As used herein, the term "pharmaceutically acceptable ester" refers to esters which hydrolyze in vivo and include, but are not limited to, those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems*, Vol. 14 of the A.C.S. Symposium Series and in Edward B. Roche, ed., *Bioreversible Carriers in Drug*

*Design, American Pharmaceutical Association and Pergamon Press*, 1987, both of which are incorporated by reference herein.

According to another aspect, the present invention provides a pharmaceutical composition, which comprises a therapeutically-effective amount of one or more compounds of the present invention or a pharmaceutically-acceptable salt, ester or prodrug thereof, together with a pharmaceutically-acceptable diluent or carrier.

The compositions may be formulated for any route of administration, in particular for oral, rectal, transdermal, subcutaneous, intravenous, intramuscular or intranasal administration. The compositions may be formulated in any conventional form, for example, as tablets, capsules, caplets, solutions, suspensions, dispersions, syrups, sprays, gels, suppositories, patches and emulsions.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject lonidamine analogue or derivative from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The "patient" or "subject" to be treated with the compounds of the present invention can be any animal, and is preferably a mammal, such as a domesticated animal or a livestock animal. More preferably, the patient is a human.

The term "inhibit" or "inhibiting" refers to a statistically significant and measurable reduction in activity, preferably a reduction of at least about 10% versus control, more preferably a reduction of about 50% or more, still more preferably a reduction of about 80% or more.

A "therapeutically effective amount" is an amount of a compound of the present invention or a combination of two or more such compounds, which inhibits, totally or partially, the progression of the condition or alleviates, at least partially, one or more symptoms of the condition. A therapeutically effective amount can also be an amount that is prophylactically effective. The amount that is therapeutically effective will depend upon the patient's size and gender, the condition to be treated, the severity of the condition and the result sought. For a given patient and condition, a therapeutically effective amount can be determined by methods known to those of skill in the art. For example, in reference to the treatment of cancer using the compounds of the present invention, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

Several of the compounds of the present invention have been shown to inhibit Hsp90 in vitro. As such, it is contemplated that therapeutically effective amounts of the compounds of the present invention will be useful as anti-cancer agents and/or neuroprotective agents.

In the context of cancer and neuroprotection, it is contemplated that some of the compounds of the present invention may be used with other Hsp90 inhibitors, chemotherapeutic agents, and/or neuroprotective agents.

The following examples are provided to illustrate the present invention and are not intended to limit the scope thereof. Those skilled in the art will readily understand that known variations of the conditions and processes of the following preparative procedures can be used to prepare these compounds.

Example 1

Synthesis of Novobiocin Analogues

In an effort to increase the affinity of novobiocin for the C-terminal ATP binding site, a library of novobiocin analogue compounds that contained both modified coumarin and sugar derivatives was prepared. The compounds were prepared as set forth in the scheme below along with a procedure recently developed for the synthesis of noviose. See Yu et al., Synthesis of (−)-Noviose from 2,3-O-Isopropylidene-D-erythronolactol, *J. Org. Chem.* 2004, 69, 7375-7378, which is incorporated by reference.

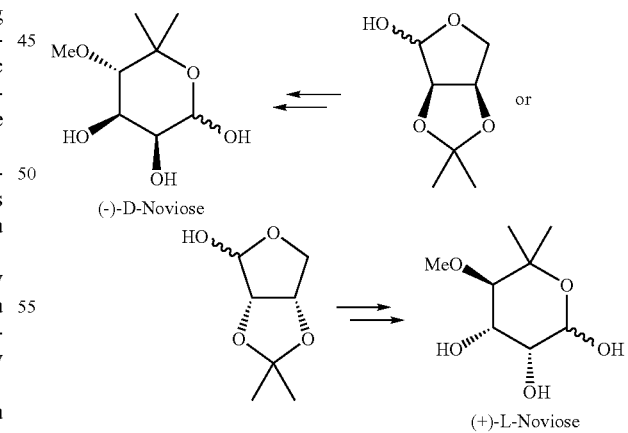

The novobiocin analogues prepared according to the scheme included modification of the coumarin ring by shortening of the amide side chain and removal of the 4-hydroxy substituent (A) (see Madhavan et al., Novel Coumarin Derivatives of Heterocyclic Compounds as Lipid Lowering Agents, *Bioorg. Med. Chem. Lett.* 2003, 13, 2547, which is incorporated by reference), removal of both the 4-hydroxy and amide linker (B), steric replacements of both the 4-hydroxy and benzamide ring (C), and 1,2-positional isomers of the noviosyl linkage (D and E).

These selected coumarin rings were coupled with trichloroacetimidate of noviose carbonate in the presence of boron trifluoride etherate as shown in scheme below. See Shen et al., Syntheses of Photolabile Novobiocin Analogues, *Bioorg. Med. Chem. Lett.* 2004, 14, 5903. The resulting cyclic carbonates (A1-E1) were treated with methanolic ammonia to provide 2'-carbamoyl (A2-E2), 3'-carbamoyl (A3-E3), and descarbamoyl products (A4-E4) in good yields. See also Yu et al., Hsp90 Inhibitors Identified from a Library of Novobiocin Analogues, *J. Am. Chem. Soc.* 2005, 127, 12778-12779, which is incorporated by reference.

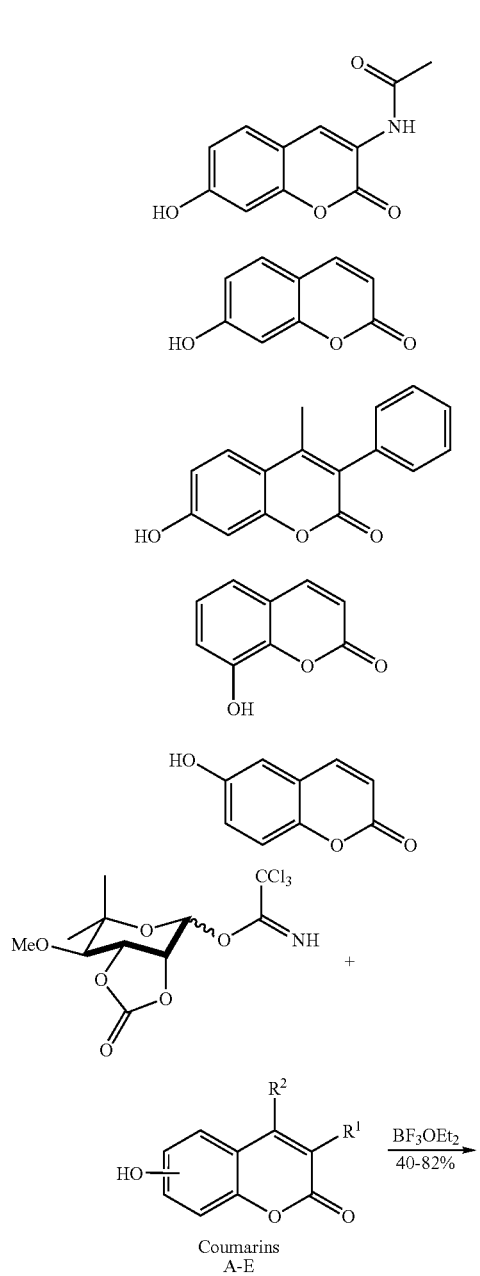
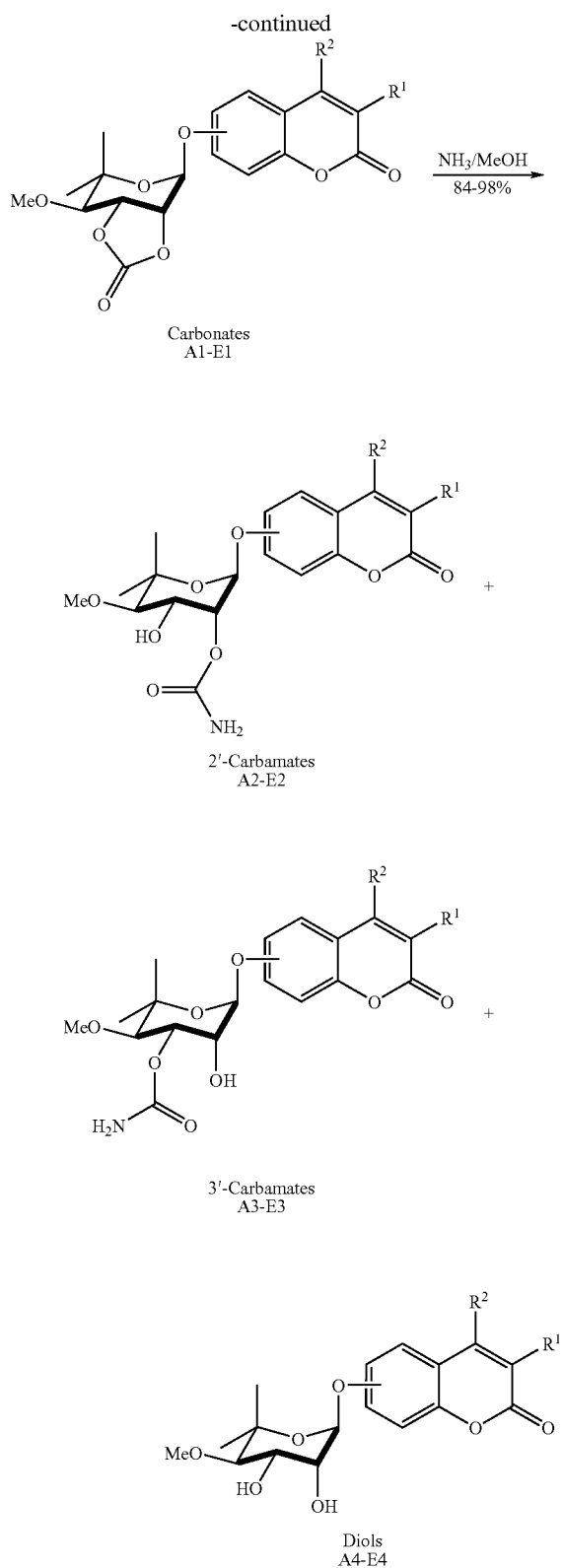

wherein $R^1$ in the above scheme is hydrogen, amido, amino, or aryl; and wherein $R^2$ in the above scheme is hydrogen, alkyl, or hydroxyl.

Overall, the following twenty-three (23) analogues of novobiocin were prepared, which are set forth below:
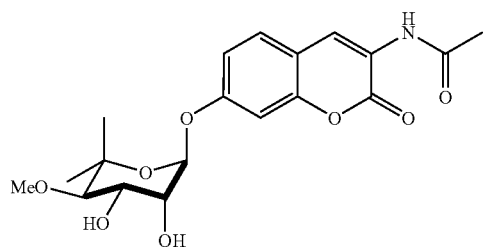
KU-1
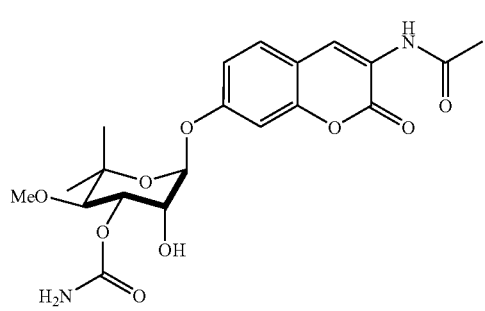
KU-2
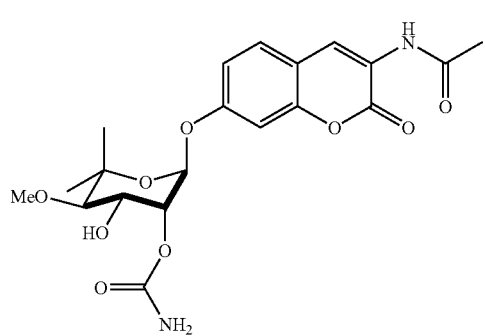
KU-3
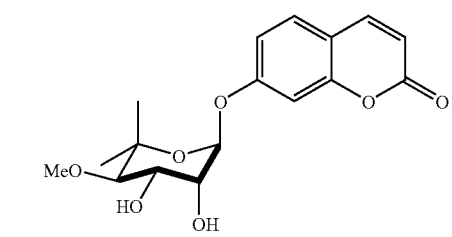
KU-4
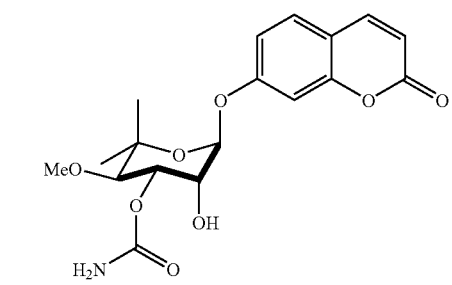
KU-5
-continued
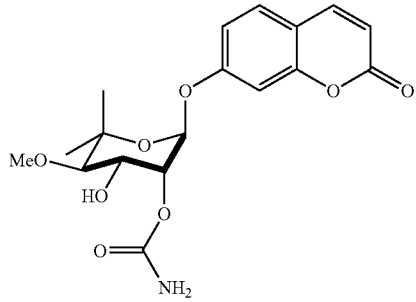
KU-6
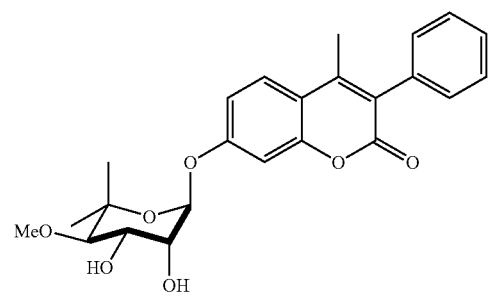
KU-7
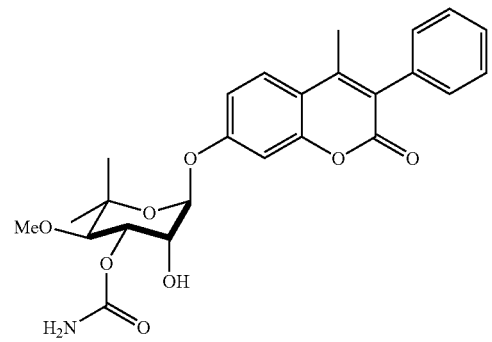
KU-8
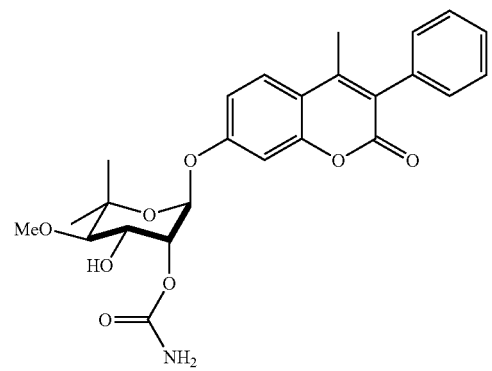
KU-9
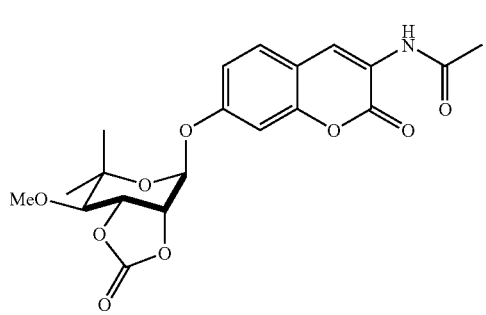
KU-10

KU-11
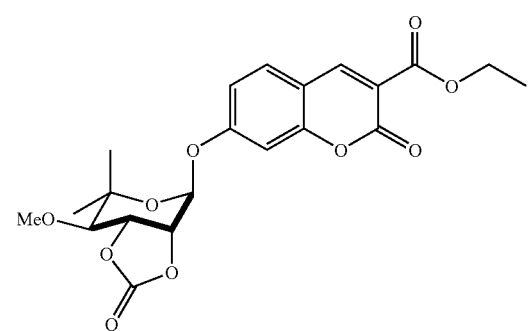
KU-12
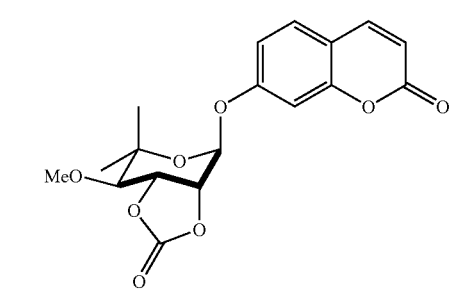
KU-13
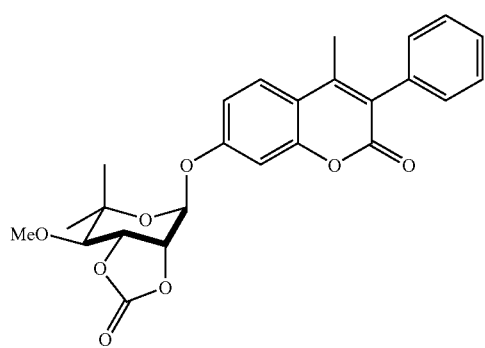
KU-14
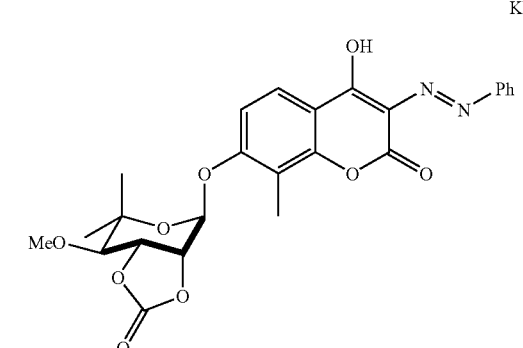
KU-15
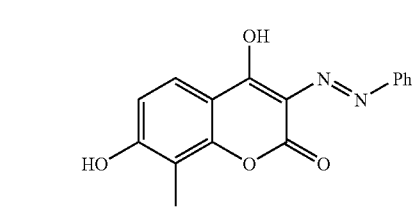
KU-16
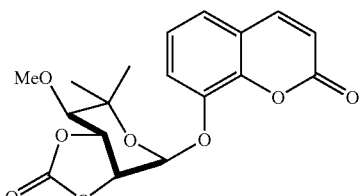
KU-17
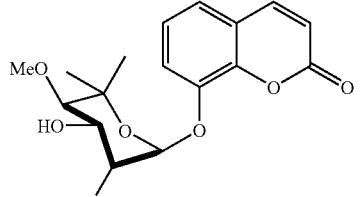
KU-18
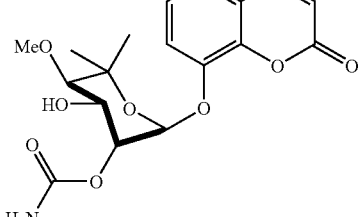
KU-19
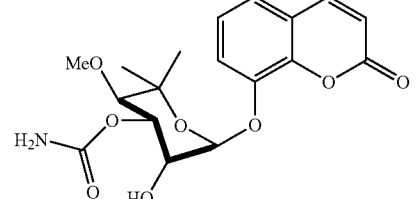
KU-20
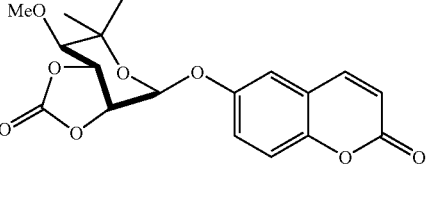
KU-21
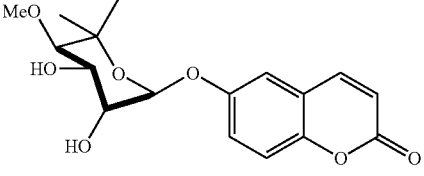
KU-22
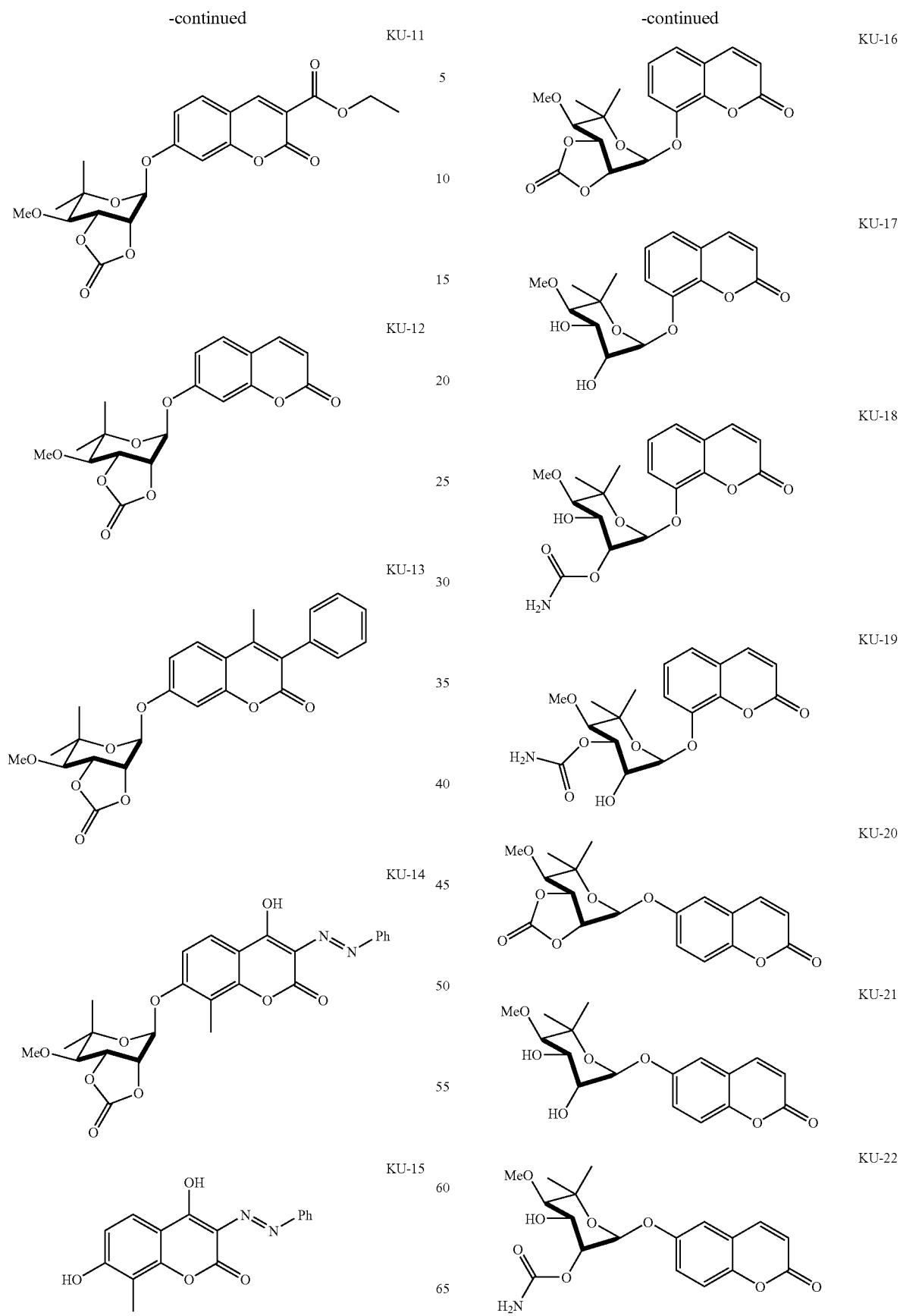

-continued

KU-23

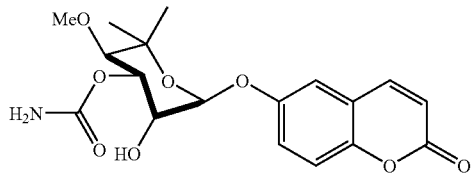

N-(7-((3aR,4R,7R,7aR)-7-methoxy-6,6-dimethyl-2-oxo-tetrahydro-3aH-[1,3]dioxolo[4,5-c]pyran-4-yloxy)-2-oxo-2H-chromen-3-yl)acetamide (A1). Noviose carbonate trichloroacetimidate (180 mg, 0.50 mmol) and 7-hydroxy-3-acetamino-coumarin A (133 mg, 0.60 mmol) were dissolved in $CH_2Cl_2$ (7 mL) before boron trifluoride etherate (30 μL, 0.03 mmol) was added to the suspension at 25° C. The mixture was stirred at 25° C. for 8 h and quenched with $Et_3N$ (0.4 mL, 2.8 mmol). The solvent was removed and the residue purified by chromatography ($SiO_2$, 5% acetone in $CH_2Cl_2$) to afford A1 (134 mg, 64%) as a colorless solid: $[\alpha]^{25}_D = -71.0°$ (c, 0.1, $CH_2Cl_2$); $^1$H NMR ($CD_3Cl$ 400 MHz) δ 8.67 (s, 1H), 8.00 (br s, 1H), 7.46 (d, J=8.6 Hz, 1H), 7.05 (d, J=2.3 Hz, 1H), 7.00 (dd, J=2.3, 8.6 Hz, 1H), 5.82 (d, J=1.5 Hz, 1H), 5.02 (dd, J=1.5, 7.8 Hz, 1H), 4.94 (t, J=7.8 Hz, 1H), 3.62 (s, 3H), 3.30 (d, J=7.8 Hz, 1H), 2.26 (s, 3H), 1.37 (s, 3H), 1.21 (s, 3H); $^{13}$C NMR ($CD_3Cl$ 100 MHz) δ 169.7, 159.2, 157.4, 153.5, 151.4, 129.2, 123.9, 122.8, 115.1, 114.6, 104.1, 94.7, 83.4, 78.3, 77.6, 77.5, 61.1, 27.9, 25.2, 22.4; IR (film) $v_{max}$ 1819, 1764, 1615, 1560, 1507, 1375, 1300, 1212, 1168, 1107, 1072, 1034, 1002, 969 cm$^{-1}$; HRMS (FAB$^+$) m/z 420.1285 (M+H$^+$, $C_{20}H_{22}NO_9$ requires 420.1294).

(2R,3R,4R,5R)-2-(3-acetamido-2-oxo-2H-chromen-7-yloxy)-4-hydroxy-5-methoxy-6,6-dimethyl-tetrahydro-2H-pyran-3-yl carbamate (A2), (3R,4S,5R,6R)-6-(3-acetamido-2-oxo-2H-chromen-7-yloxy)-5-hydroxy-3-methoxy-2,2-dimethyl tetrahydro-2H-pyran-4-yl carbamate (A3) and N-(7-((2R,3R,4S,5R)-3,4-dihydroxy-5-methoxy-6,6-dimethyl-tetrahydro-2H-pyran-2-yloxy)-2-oxo-2H-chromen-3-yl)acetamide (A4). Noviosylated coumarin A1 (20 mg, 0.047 mmol) was dissolved in methanolic ammonia (7.0 M, 2 mL) at 25° C. and stirred for 24 h. The solvent was evaporated and the residue purified by preparative HPLC ($SiO_2$, 20% 2-propanol in hexanes) to afford A2 (4.2 mg, 22%), A3 (8.6 mg, 42%) and A4 (3.5 mg, 20%) as colorless solids.

A2: $[\alpha]^{25}_D = -143.2°$ (c, 0.11, 50% MeOH in $CH_2Cl_2$); $^1$HNMR (50% $CD_3OD$ in $CD_2Cl_2$ 400 MHz) δ 8.58 (s, 1H), 7.44 (d, J=8.4 Hz, 1H), 7.01 (s, 1H), 6.97 (d, J=8.4 Hz, 1H), 5.59 (d, J=2.0 Hz, 1H), 5.03 (dd, J=2.0, 3.6 Hz, 1H), 4.25 (dd, J=3.6, 9.7 Hz, 1H), 3.57 (s, 3H), 3.30 (d, J=9.7 Hz, 1H), 2.19 (s, 3H), 1.31 (s, 3H), 1.13 (s, 3H); $^{13}$CNMR (50% $CD_3OD$ in $CD_2Cl_2$ 100 MHZ) δ 168.8, 157.2, 156.4, 155.5, 149.5, 126.9, 122.9, 120.4, 112.6, 112.3, 101.6, 94.8, 82.5, 77.0, 71.9, 64.7, 59.9, 27.0, 22.1, 20.6; IR (film) $v_{max}$ 3473, 1716, 1689, 1610, 1540, 1528, 1505, 1375, 1240, cm$^{-1}$; HRMS (FAB$^+$) m/z 437.1565 (M+H$^+$, $C_{20}H_{25}N_2O_9$ requires 437.1560).

A3: $[\alpha]^{25}_D = -116.2°$ (c, 0.24, 50% MeOH in $CH_2Cl_2$); $^1$HNMR ($CD_3OD$ 400 MHz) δ 8.59 (s, 1H), 7.52 (d, J=10.8 Hz, 1H), 7.04 (s, 1H), 7.03 (d, J=10.8 Hz, 1H), 5.56 (d, J=2.4 Hz, 1H), 5.25 (dd, J=3.2, 9.8 Hz, 1H), 4.20 (dd, J=2.4, 3.2 Hz, 1H), 3.58 (s, 3H), 3.35 (d, J=9.8 Hz, 1H), 2.22 (s, 3H), 1.27 (s, 3H), 1.18 (s, 3H); $^{13}$CNMR ($CD_3OD$ 100 MHZ) δ 171.6, 158.8, 158.7, 158.1, 151.8, 128.9, 125.6, 122.5, 114.4, 114.2, 103.1, 99.1, 81.6, 79.0, 71.8, 69.7, 60.1, 27.9, 22.9, 22.4; IR (film) $v_{max}$ 3470, 1716, 1686, 1615, 1538, 1523, 1505, 1372, 1242, 1120 cm$^{-1}$; HRMS (FAB$^+$) m/z 437.1576 (M+H$^+$, $C_{20}H_{25}N_2O_9$ requires 437.1560).

A4: $[\alpha]^{25}_D = -351.6°$ (c, 0.06, 50% MeOH in $CH_2Cl_2$); $^1$HNMR ($CD_3OD$ 400 MHz) δ 8.58 (s, 1H), 7.51 (d, J=8.3 Hz, 1H), 7.03 (s, 1H), 7.02 (d, J=8.3 Hz, 1H), 5.55 (d, J=2.3 Hz, 1H), 4.10 (dd, J=3.3, 9.6 Hz, 1H), 4.03 (dd, J=2.4, 3.3 Hz, 1H), 3.60 (s, 3H), 3.38 (d, J=9.6 Hz, 1H), 2.21 (s, 3H), 1.30 (s, 3H), 1.13 (s, 3H); $^{13}$CNMR ($CD_3OD$ 100 MHZ) δ 171.6, 158.9, 158.8, 151.8, 128.9, 125.7, 122.5, 114.3, 114.1, 103.1, 99.2, 84.2, 78.8, 71.5, 68.4, 61.1, 28.2, 22.9, 22.4; IR (film) $v_{max}$ 3326, 1714, 1674, 1613, 1558, 1553, 1108 cm$^{-1}$; HRMS (FAB$^+$) m/z 394.1492 (M+H$^+$, $C_{19}H_{24}O_8$ requires 394.1502).

7-((3aR,4R,7R,7aR)-7-methoxy-6,6-dimethyl-2-oxo-tetrahydro-3aH-[1,3]dioxolo[4,5-c]pyran-4-yloxy)-2H-chromen-2-one (B1). Noviose carbonate trichloroacetimidate (90 mg, 0.25 mmol) and 7-hydroxy-coumarin B (48 mg, 0.30 mmol) were dissolved in $CH_2Cl_2$ (2 mL) before boron trifluoride etherate (10 μL, 0.01 mmol) was added to the suspension at 25° C. The mixture was stirred at 25° C. for 8 h and quenched with $Et_3N$ (0.1 mL, 0.7 mmol). The solvent was removed and the residue purified by chromatography ($SiO_2$, 2% acetone in $CH_2Cl_2$) to afford B1 (66 mg, 73%) as a colorless solid: $[\alpha]^{25}_D = -85.6°$ (c, 1.15, $CH_2Cl_2$); $^1$HNMR ($CDCl_3$ 400 MHz) δ 7.69 (d, J=9.5 Hz, 1H), 7.43 (d, J=8.6 Hz, 1H), 7.05 (d, J=2.3 Hz, 1H), 6.95 (dd, J=2.3, 8.6 Hz, 1H), 6.34 (d, J=9.5 Hz, 1H), 5.84 (d, J=1.3 Hz, 1H), 5.03 (dd, J=1.3, 7.7 Hz, 1H), 4.94 (t, J=7.7 Hz, 1H), 3.62 (s, 3H), 3.30 (d, J=7.7 Hz, 1H), 1.37 (s, 3H), 1.20 (s, 3H); $^{13}$CNMR ($CDCl_3$ 100 MHZ) δ 161.2, 158.9, 155.9, 153.5, 143.5, 129.4, 114.7, 114.4, 113.7, 104.4, 94.6, 83.4, 78.3, 77.8, 77.5, 61.0, 27.9, 22.4; IR (film) $v_{max}$ 1809, 1730, 1612, 1171, 1157, 1109 cm$^{-1}$; HRMS (FAB$^+$) m/z 363.1083 (M+H$^+$, $C_{18}H_{19}O_8$ requires 363.1080).

(3R,4S,5R,6R)-5-hydroxy-3-methoxy-2,2-dimethyl-6-(2-oxo-2H-chromen-7-yloxy)-tetrahydro-2H-pyran-4-yl carbamate (B2), (2R,3R,4R,5R)-4-hydroxy-5-methoxy-6,6-dimethyl-2-(2-oxo-2H-chromen-7-yloxy)-tetrahydro-2H-pyran-3-yl carbamate (B3) and 7-((2R,3R,4S,5R)-3,4-dihydroxy-5-methoxy-6,6-dimethyl-tetrahydro-2H-pyran-2-yloxy)-2H-chromen-2-one (B4). Noviosylated coumarin B1 (25 mg, 0.07 mmol) was dissolved in methanolic ammonia (7.0 M, 2 mL) at 25° C. and stirred for 24 h. The solvent was evaporated and the residue purified by preparative TLC ($SiO_2$, 25% acetone in methylene chloride) to afford B2 (4.3 mg, 16%), B3 (14.5 mg, 52%) and B4 (4.0 mg, 17%) as colorless solids.

B2: $[\alpha]^{25}_D = -85.1°$ (c, 0.71, 50% MeOH in $CH_2Cl_2$); $^1$HNMR ($CD_3OD$ 400 MHz) δ 7.91 (d, J=9.5 Hz, 1H), 7.58 (dd, J=1.3, 9.0 Hz, 1H), 7.04 (s, 1H), 7.03 (d, J=9.0 Hz, 1H), 6.30 (d, J=9.5 Hz, 1H), 5.65 (d, J=2.1 Hz, 1H), 5.04 (dd, J=2.6, 3.4 Hz, 1H), 4.28 (dd, J=3.4, 9.9 Hz, 1H), 3.62 (s, 3H), 3.39 (d, J=9.5 Hz, 1H), 1.35 (s, 3H), 1.15 (s, 3H); $^{13}$CNMR ($CD_3OD$ 100 MHZ) δ 161.7, 159.7, 157.5, 155.3, 144.1, 129.1, 113.6, 113.4, 112.8, 103.0, 96.4, 83.9, 78.5, 73.4, 66.2, 60.8, 28.0, 21.8; IR (film) $v_{max}$ 3438, 2982, 2932, 1731, 1616, 1403, 1338, 1280, 1117, 1002, 963 cm$^{-1}$; HRMS (FAB$^+$) m/z 380.1333 (M+H$^+$, $C_{17}H_{21}O_7$ requires 380.1345).

B3: $[\alpha]^{25}_D = -111.8°$ (c, 0.18, 50% MeOH in $CH_2Cl_2$); $^1$HNMR ($CD_3OD$ 400 MHz) δ 7.91 (d, J=9.5 Hz, 1H), 7.58 (d, J=8.3 Hz, 1H), 7.05 (s, 1H), 7.04 (d, J=8.3 Hz, 1H), 6.30 (d, J=9.9 Hz, 1H), 5.59 (d, J=2.4 Hz, 1H), 5.25 (dd, J=3.2, 9.8 Hz, 1H), 4.20 (dd, J=2.4, 3.2 Hz, 1H), 3.59 (d, J=9.5 Hz, 1H), 3.57 (s, 3H), 1.36 (s, 3H), 1.17 (s, 3H); $^{13}$CNMR ($CD_3OD$ 100 MHZ) δ 161.7, 159.9, 157.7, 155.3, 144.2, 129.1, 113.6, 113.5, 112.7, 102.9, 98.6, 81.1, 78.6, 71.4, 69.3, 60.6, 27.5, 22.0; IR (film) $v_{max}$ 3359, 2979, 2937, 1710, 1615, 1317, 1120, 1092, 995 cm$^{-1}$; HRMS (FAB$^+$) m/z 380.1327 (M+H$^+$, C$_{17}$H$_{21}$O$_7$ requires 380.1345).

B4: [α]$^{25}_D$=−129.4° (c, 0.18, 50% MeOH in CH$_2$Cl$_2$); $^1$HNMR (CD$_3$OD 400 MHz) δ 7.91 (d, J=9.5 Hz, 1H), 7.57 (dd, J=2.4, 10.4 Hz, 1H), 7.02 (m, 2H), 6.27 (dd, J=4.5, 9.5 Hz, 1H), 5.57 (d, J=2.4 Hz, 1H), 4.11 (dd, J=3.3, 9.5 Hz, 1H), 4.03 (dd, J=2.4, 3.3 Hz, 1H), 3.60 (s, 3H), 3.39 (d, J=9.5 Hz, 1H), 1.35 (s, 3H), 1.12 (s, 3H); $^{13}$CNMR (CD$_3$OD 100 MHZ) δ 161.7, 160.9, 155.4, 144.2, 129.0, 113.5, 113.4, 112.6, 102.9, 98.8, 83.7, 78.4, 71.1, 67.9, 60.7, 27.7, 22.0; IR (film) ν$_{max}$ 3415, 2984, 2934, 1730, 1718, 1707, 1615, 1118, 999, 957 cm$^{-1}$; HRMS (FAB$^+$) m/z 337.11279 (M+H$^+$, C$_{17}$H$_{21}$O$_7$ requires 337.1287).

7-((3aR,4R,7R,7aR)-7-methoxy-6,6-dimethyl-2-oxo-tetrahydro-3aH-[1,3]dioxolo[4,5-c]pyran-4-yloxy)-4-methyl-3-phenyl-2H-chromen-2-one (C1). Noviose carbonate trichloroacetimidate (90 mg, 0.25 mmol) and 7-hydroxy-4-methyl-3-phenyl-coumarin C (76 mg, 0.30 mmol) were dissolved in CH$_2$Cl$_2$ (2 mL) before boron trifluoride etherate (10 μL, 0.01 mmol) was added to the suspension at 25° C. The mixture was stirred at 25° C. for 8 h and quenched with Et$_3$N (0.1 mL, 0.7 mmol). The solvent was removed and the residue purified by chromatography (SiO$_2$, 1% acetone in CH$_2$Cl$_2$) to afford C1 (92 mg, 73%) as a colorless solid:

[α]$^{25}_D$=−75.8° (c, 1.41, CH$_2$C12); $^1$HNMR (CDCl$_3$ 400 MHz) δ 7.80 (d, J=9.6 Hz, 1H), 7.44 (m, 3H), 7.33 (m, 2H), 7.09 (d, J=2.4 Hz, 1H), 7.01 (dd, J=2.4, 5.2 Hz, 1H), 5.84 (d, J=1.3 Hz, 1H), 5.03 (dd, J=1.3, 7.7 Hz, 1H), 4.94 (t, J=7.7 Hz, 1H), 3.62 (s, 3H), 3.30 (d, J=7.7 Hz, 1H), 2.31 (s, 3H), 1.37 (s, 3H), 1.20 (s, 3H); $^{13}$CNMR (CDCl$_3$ 100 MHZ) δ 161.0, 158.0, 153.9, 153.0, 147.4, 134.3, 130.0 (2C), 128.3 (2C), 128.0, 126.2, 125.2, 115.6, 113.0, 103.7, 94.1, 82.9, 77.8, 76.7, 76.5, 60.5, 27.4, 22.0, 16.5; IR (film) ν$_{max}$ 1874, 1715, 1612, 1564, 1507, 1383, 1262, 1167, 1130, 1113, 1070, 1033, 1006, 968, 936 cm$^{-1}$; HRMS (FAB$^+$) m/z 453.1554 (M+H$^+$, C$_{25}$H$_{25}$O$_8$ requires 453.1549).

(3R,4S,5R,6R)-5-hydroxy-3-methoxy-2,2-dimethyl-6-(4-methyl-2-oxo-3-phenyl-2H-chromen-7-yloxy)-tetrahydro-2H-pyran-4-yl carbamate (C2), (2R,3R,4R,5R)-4-hydroxy-5-methoxy-6,6-dimethyl-2-(4-methyl-2-oxo-3-phenyl-2H-chromen-7-yloxy)-tetrahydro-2H-pyran-3-yl carbamate (C3) and 7-((2R,3R,4S,5R)-3,4-dihydroxy-5-methoxy-6,6-dimethyl-tetrahydro-2H-pyran-2-yloxy)-4-methyl-3-phenyl-2H-chromen-2-one (C4). Noviosylated coumarin C1 (25 mg, 0.055 mmol) was dissolved in methanolic ammonia (7.0 M, 2 mL) at 25° C. and stirred for 24 h. The solvent was evaporated and the residue purified by preparative TLC (SiO$_2$, 25% acetone in methylene chloride) to afford C2 (6.3 mg, 25%), C3 (13.7 mg, 53%) and C4 (3.0 mg, 13%) as colorless solids.

C2: [α]$^{25}_D$=−72.9° (c, 0.19, 50% MeOH in CH$_2$Cl$_2$); $^1$HNMR (CD$_3$OD 400 MHz) δ 7.80 (d, J=9.0 Hz, 1H), 7.43 (m, 3H), 7.32 (m, 2H), 7.10 (m, 2H), 5.69 (d, J=1.8 Hz, 1H), 5.06 (dd, J=2.1, 3.2 Hz, 1H), 4.30 (dd, J=3.2, 9.7 Hz, 1H), 3.63 (s, 3H), 3.40 (d, J=9.7 Hz, 1H), 2.31 (s, 3H), 1.36 (s, 3H), 1.18 (s, 3H); $^{13}$CNMR (CD$_3$OD 100 MHZ) δ 162.2, 159.7, 158.0, 154.2, 149.2, 135.1, 130.3 (2C), 128.4 (2C), 128.1, 127.0, 124.7, 115.3, 113.7, 103.2, 96.8, 84.4, 78.9, 73.8, 66.7, 61.3, 28.4, 22.3, 15.8; IR (film) ν$_{max}$ 3474, 2986, 2924, 1713, 1605, 1382, 1355, 1263, 1124, 1001, 967 cm$^{-1}$; HRMS (FAB$^+$) m/z 470.1821 (M+H$^+$, C$_{25}$H$_{28}$NO$_8$ requires 470.1815).

C3: [α]$^{25}_D$=−92.3° (c, 0.28, 50% MeOH in CH$_2$Cl$_2$); $^1$HNMR (CD$_3$OD 400 MHz) δ 7.75 (d, J=9.5 Hz, 1H), 7.45 (m, 3H), 7.34 (m, 2H), 7.06 (m, 2H), 5.63 (d, J=2.4 Hz, 1H), 5.18 (dd, J=3.2, 9.6 Hz, 1H), 4.18 (dd, J=2.4, 3.2 Hz, 1H), 3.54 (s, 3H), 3.40 (d, J=9.5 Hz, 1H), 2.27 (s, 3H), 1.35 (s, 3H), 1.16 (s, 3H); $^{13}$CNMR (CD$_3$CN 125 MHZ) δ 160.7, 159.0, 156.0, 153.8, 148.0, 135.2, 130.1 (2C), 128.1 (2C), 127.7, 126.7, 124.4, 114.9, 113.1, 103.1, 98.2, 81.0, 78.4, 71.3, 69.0, 60.7, 27.7, 22.4, 15.8; IR (film) ν$_{max}$ 3459, 3331, 2981, 2925, 1714, 1606, 1379, 1335, 1263, 1124, 1072 cm$^{-1}$; HRMS (FAB$^+$) m/z 470.1811 (M+H$^+$, C$_{25}$H$_{28}$NO$_8$ requires 470.1815).

C4: [α]$^{25}_D$=−86.0° (c, 0.12, 50% MeOH in CH$_2$Cl$_2$); $^1$HNMR (CD$_3$OD 400 MHz) δ 7.80 (d, J=9.6 Hz, 1H), 7.44 (m, 3H), 7.33 (m, 2H), 7.09 (m, 2H), 5.60 (d, J=1.9 Hz, 1H), 4.12 (dd, J=3.3, 9.5 Hz, 1H), 4.05 (dd, J=2.4, 3.1 Hz, 1H), 3.61 (s, 3H), 3.40 (d, J=9.5 Hz, 1H), 2.32 (s, 3H), 1.37 (s, 3H), 1.15 (s, 3H); $^{13}$CNMR (CD$_3$OD 100 MHZ) δ 161.9, 159.6, 153.8, 149.1, 134.7, 129.9 (2C), 127.9 (2C), 127.7, 126.5, 124.1, 114.7, 113.4, 102.7, 98.8, 83.8, 78.4, 71.1, 68.0, 60.7, 27.8, 22.0, 15.4; IR (film) ν$_{max}$ 3403, 2977, 2924, 1717, 1607, 1558, 1505, 1381, 1260, 1124, 992 cm$^{-1}$; HRMS (FAB$^+$) m/z 427.1750 (M+H$^+$, C$_{24}$H$_{27}$O$_7$ requires 427.1757).

8-(7-Methoxy-6,6-dimethyl-2-oxo-tetrahydro-[1,3]dioxolo[4,5-c]pyran-4-yloxy)-chromen-2-one (D1) Noviose carbonate trichloroacetimidate (176 mg, 0.49 mmol) and 8-hydroxy-coumarin D (95 mg, 0.59 mmol) were dissolved in CH$_2$Cl$_2$ (5 mL). Boron trifluoride etherate (20 μL, 0.08 mmol) was added to the suspension at 25° C. The resulting slurry was stirred at 25° C. for 10 h before the solvent was removed and the residue purified by chromatography (SiO$_2$, 1% MeOH in CHCl$_3$) to afford D1 (85 mg, 40%) as a colorless solid:

[α]$_D^{31}$=−57° (c=0.1, 50% MeOH in CH$_2$Cl$_2$); $^1$H NMR (CDCl$_3$, 500 MHz) δ 7.69 (d, J=9.6 Hz, 1H), 7.31 (t, J=9.1 Hz, 1H), 7.23 (dd, J=2.8 Hz, 9.0 Hz, 1H), 7.16 (d, J=2.8 Hz, 1H), 6.47 (d, J=9.6 Hz, 1H), 5.77 (d, J=1.0 Hz, 1H), 5.03 (dd, J=1.2 Hz, 7.8 Hz, 1H), 4.95 (t, J=7.7 Hz, 1H), 3.62 (s, 3H), 3.30 (d, J=7.7 Hz, 1H), 1.37 (s, 3H), 1.20 (s, 3H); $^{13}$C NMR (CDCl$_3$, 125 MHz) δ 160.6, 153.1, 152.1, 149.4, 142.9, 120.8, 119.3, 118.0, 117.4, 113.3, 94.5, 82.9, 77.9, 77.2, 76.5, 60.5, 27.5, 22.0; IR (film) ν$_{max}$ 3054, 2987, 1817, 1730, 1572, 1422, 1166, 1112, 1040, 896, 739 cm$^{-1}$; HRMS (FAB$^+$) m/z 363.1088 (M+H$^+$, C$_{18}$H$_{19}$O$_8$ requires m/z 363.1080).

Carbamic acid 4-hydroxy-5-methoxy-6,6-dimethyl-2-(2-oxo-2H-chromen-8-yloxy)-tetrahydro-pyran-3-yl ester (D2), carbamic acid 5-hydroxy-3-methoxy-2,2-dimethyl-6-(2-oxo-2H-chromen-8-yloxy)-tetrahydro-pyran-4-yl ester (D3), 8-(3,4-Dihydroxy-5-methoxy-6,6-dimethyl-tetrahydro-pyran-2-yloxy)-chromen-2-one (D4) D1 (17 mg, 0.047 mmol) was dissolved in methanolic ammonia (2.0 M, 5 mL, 10 mmol) at 25° C. and stirred for 5 h before the solvent was removed. The residue was purified by preparative TLC (SiO$_2$, 25% acetone in CH$_2$Cl$_2$) to afford D2 (3.8 mg, 21%), D3 (5.5 mg, 31%), and D4 (7.2 mg, 46%) as colorless solids.

D2: [α]$_D^{31}$=−19° (c=0.1, 50% MeOH in CH$_2$Cl$_2$); $^1$H NMR (CD$_3$OD in CD$_2$Cl$_2$, 500 MHz) δ 7.79 (d, J=9.6 Hz, 1H), 7.26 (m, 3H), 6.43 (d, J=9.6 Hz, 1H), 5.59 (d, J=2.0 Hz, 1H), 5.05 (dd, J=2.1 Hz, 3.4 Hz, 1H), 4.28 (m, 2H), 3.61 (s, 3H), 3.32 (m, 1H), 1.34 (s, 3H), 1.18 (s, 3H); $^{13}$C NMR (CD$_3$OD in CDCl$_3$, 100 MHz) δ 162.1, 158.0, 153.6, 149.3, 144.6, 121.1, 119.9, 117.7, 116.6, 113.6, 97.1, 84.5, 78.8, 74.1, 66.7, 61.4, 28.6, 22.4; IR (film) ν$_{max}$ 3054, 2987, 1729, 1422, 896, 739, 705 cm$^{-1}$; HRMS (ESI$^+$) m/z 380.1356 (M+H$^+$, C$_{18}$H$_{22}$NO$_8$ requires m/z 380.1345).

D3: [α]$_D^{31}$=−69° (c=0.1, 50% MeOH in CH$_2$Cl$_2$); $^1$H NMR (CD$_3$OD in CD$_2$Cl$_2$, 500 MHz) δ 7.84 (d, J=9.6 Hz, 1H), 7.30 (m, 3H), 6.44 (d, J=9.5 Hz, 1H), 5.51 (d, J=2.3 Hz, 1H), 5.28 (dd, J=3.2 Hz, 9.8 Hz, 1H), 4.21 (m, 1H), 3.56 (s, 1H), 3.55 (s, 3H), 1.35 (s, 3H), 1.20 (s, 3H); $^{13}$C NMR (CD$_3$OD in CDCl$_3$, 125 MHz) δ 161.8, 157.4, 153.3, 148.7, 144.2, 120.8, 119.3, 117.4, 116.2, 113.2, 98.9, 81.3, 78.6, 71.5, 69.5, 60.8, 27.9, 22.3; IR (film) $v_{max}$ 3054, 2987, 1732, 1422, 896, 742 cm$^{-1}$; HRMS (ESI$^+$) m/z 380.1348 (M+H$^+$, C$_{18}$H$_{22}$NO$_8$ requires m/z 380.1345).

D4: $[\alpha]_D^{31}$=−91° (c=0.1, 50% MeOH in CH$_2$Cl$_2$); $^1$H NMR (CD$_3$OD in CD$_2$Cl$_2$, 500 MHz) δ 7.82 (d, J=9.5 Hz, 1H), 7.26 (m, 3H), 6.43 (d, J=9.5 Hz, 1H), 5.50 (d, J=2.3 Hz, 1H), 4.12 (dd, J=3.4 Hz, 9.3 Hz, 1H), 4.05 (d, J=2.4 Hz, 1H), 3.59 (s, 3H), 3.33 (m, 1H), 1.35 (s, 3H), 1.15 (s, 3H); $^{13}$C NMR (CD$_3$OD in CDCl$_3$, 125 MHz) δ 161.7, 153.4, 148.6, 144.2, 120.7, 119.3, 117.3, 116.1, 113.1, 98.9, 83.8, 78.3, 71.1, 68.0, 60.9, 28.0, 22.2; IR (film) $v_{max}$ 3455, 3053, 2988, 1704, 1568, 1112, 738 cm$^{-1}$; HRMS (FAB$^+$) m/z 337.1267 (M+H$^+$, C$_{17}$H$_{21}$O$_7$ requires m/z 337.1287).

6-(7-Methoxy-6,6-dimethyl-2-oxo-tetrahydro-[1,3]di-oxolo[4,5-c]pyran-4-yloxy)-chromen-2-one (E1) Noviose carbonate trichloroacetimidate (150 mg, 0.42 mmol) and 6-hydroxycoumarin E (67 mg, 0.42 mmol) were dissolved in CH$_2$Cl$_2$ (4 mL). Boron trifluoride etherate (20 µL, 0.06 mmol) was added to the suspension at 25° C. The resulting slurry was stirred at 25° C. for 10 h before the solvent was removed and the residue purified by chromatography (SiO$_2$, 1% MeOH in CHCl$_3$) to afford E1 (63 mg, 42%) as a colorless solid:

$[\alpha]_D^{31}$=−59° (c=0.1, 50% MeOH in CH$_2$Cl$_2$); $^1$H NMR (CDCl$_3$, 500 MHz) δ 7.69 (d, J=9.6 Hz, 1H), 7.30 (d, J=9.0 Hz, 1H), 7.23 (dd, J=2.7 Hz, 9.0 Hz, 1H), 7.16 (d, J=2.7 Hz, 1H), 6.47 (d, J=9.6 Hz, 1H), 5.77 (m, 1H), 5.02 (dd, J=1.0 Hz, 7.8 Hz, 1H), 4.95 (d, J=7.7 Hz, 1H), 3.61 (s, 3H), 3.30 (d, J=7.7 Hz, 1H), 1.37 (s, 3H), 1.23 (s, 3H); $^{13}$C NMR (CDCl$_3$, 125 MHz) δ 160.6, 153.1, 152.1, 149.4, 142.9, 120.8, 119.3, 118.0, 117.4, 113.3, 94.5, 82.9, 77.9, 77.2, 76.5, 60.5, 27.5, 22.0; IR (film) $v_{max}$ 3054, 2987, 1818, 1730, 1422, 896, 739, 705 cm$^{-1}$; HRMS (FAB$^+$) m/z 363.1109 (M+H$^+$, C$_{18}$H$_{19}$O$_8$ requires m/z 363.1080).

Carbamic acid 5-hydroxy-3-methoxy-2,2-dimethyl-6-(2-oxo-2H-chromen-6-yloxy)-tetrahydro-pyran-4-yl ester (E2), Carbamic acid 4-hydroxy-5-methoxy-6,6-dimethyl-2-(2-oxo-2H-chromen-6-yloxy)-tetrahydro-pyran-3-yl ester (E3), 6-(3,4-Dihydroxy-5-methoxy-6,6-dimethyl-tetrahydro-pyran-2-yloxy)-chromen-2-one (E4) E1 (17 mg, 0.047 mmol) was dissolved in methanolic ammonia (7.0 M, 5 mL, 35 mmol) at 25° C. and stirred for 5 h before the solvent was removed. The residue was purified by preparative TLC (SiO$_2$, 25% acetone in CH$_2$Cl$_2$) to afford compound E2 (7.8 mg, 34%), E3 (9.9 mg, 43%), and E4 (4.7 mg, 23%) as colorless solids.

E2: $[\alpha]_D^{31}$=−45° (c=0.1, 50% MeOH in CH$_2$Cl$_2$). $^1$H NMR (CD$_3$OD in CD$_2$Cl$_2$, 500 MHz) δ 7.82 (d, J=9.6 Hz, 1H), 7.27 (m, 3H), 6.44 (d, J=9.5 Hz, 1H), 5.60 (d, J=2.0 Hz, 1H), 5.05 (dd, J=2.0 Hz, 3.4 Hz, 1H), 4.28 (m, 1H), 3.61 (s, 3H), 3.32 (m, 1H), 1.34 (s, 3H), 1.18 (s, 3H); $^{13}$C NMR (CD$_3$OD in CD$_2$Cl$_2$, 125 MHz) δ 161.6, 157.2, 153.1, 148.8, 143.9, 120.8, 119.3, 117.4, 116.4, 113.2, 96.7, 84.1, 78.4, 73.7, 66.3, 61.3, 28.4, 22.2; IR (film) $v_{max}$ 3054, 2987, 1729, 1422, 896, 738, 705 cm$^{-1}$; HRMS (ESI$^+$) m/z 380.1327 (M+H$^+$, C$_{18}$H$_{22}$NO$_8$ requires m/z 380.1345).

E3: $[\alpha]_D^{31}$=−80° (c=0.1, 50% MeOH in CH$_2$Cl$_2$); $^1$H NMR (CD$_3$OD in CD$_2$Cl$_2$, 500 MHz) δ 7.79 (d, J=9.5 Hz, 1H), 7.28 (d, J=2.3 Hz, 2H), 7.25 (s, 1H), 6.43 (d, J=9.5 Hz, 1H), 5.50 (d, J=2.3 Hz, 1H), 5.26 (dd, J=3.2 Hz, 9.8 Hz, 1H), 4.21 (t, J=2.7 Hz, 1H), 3.56 (m, 1H), 3.55 (s, 3H), 1.35 (s, 3H), 1.19 (s, 3H); $^{13}$C NMR (CD$_3$OD in CD$_2$Cl$_2$, 125 MHz) δ 159.5, 155.0, 151.1, 146.8, 141.8, 118.7, 117.3, 115.4, 114.4, 111.2, 96.7, 79.3, 76.6, 69.6, 67.4, 59.0, 26.0, 20.4; IR (film) $v_{max}$ 3054, 2987, 1731, 1422, 1265, 896, 742 cm$^{-1}$; HRMS (ESI$^+$) m/z 380.1324 (M+H$^+$, C$_{18}$H$_{22}$NO$_8$ requires m/z 380.1345).

E4: $[\alpha]_D^{31}$=−89° (c=0.05, 50% MeOH in CH$_2$Cl$_2$); $^1$H NMR (CD$_3$OD in CD$_2$Cl$_2$, 400 MHz) δ 7.83 (d, J=9.6 Hz, 1H), 7.26 (m, 3H), 6.44 (d, J=9.5 Hz, 1H), 5.50 (d, J=2.3 Hz, 1H), 4.12 (dd, J=3.4 Hz, 9.3 Hz, 1H), 4.05 (d, J=2.4 Hz, 1H), 3.59 (s, 3H), 3.33 (m, 1H), 1.34 (s, 3H), 1.14 (s, 3H); $^{13}$C NMR (CD$_3$OD in CD$_2$Cl$_2$, 125 MHz) δ 162.1, 153.8, 149.2, 144.5, 121.3, 119.8, 117.8, 116.8, 113.5, 99.3, 84.4, 78.8, 71.6, 68.5, 61.6, 28.6, 22.8; IR (film) $v_{max}$ 3454, 3054, 2987, 1705, 1568, 1422, 1111, 896, 738 cm$^{-1}$; HRMS (FAB$^+$) m/z 337.1275 (M+H$^+$, C$_{17}$H$_{21}$O$_7$ requires m/z 337.1287).

As discussed more fully below, these compounds were then tested for biological activity with respect to Hsp90 inhibition. Based on the results, various additional modifications to the side chains at R$^1$ and R$^2$ in the above scheme are proposed, as well as modifications to the coumarin ring and sugar moiety.

Example 2

Degradation of Phospho-AKT

Inhibition of Hsp90 results in the degradation of Hsp90-dependent clients via ubiquitination of the unfolded client followed by proteasome-mediated hydrolysis. To test whether Hsp90 client proteins were degraded in the presence of these novobiocin analogues, each member of the library from Example 1 was incubated with SKBr3 breast cancer cells at a concentration of 100 µM. Western blot analysis of the protein lysates demonstrated that several of the compounds were capable of causing the degradation of the Hsp90-dependent oncogenic client protein, phospho-AKT as represented in FIG. 1. Phospho-AKT was chosen as a client protein for this assay because of previous reports indicating that phospho-AKT is a more sensitive indicator of Hsp90 inhibition than AKT. Geldanamycin (GDA, 0.5 µM) was used as a positive control for Hsp90 inhibition.

As can be seen from FIG. 1, A4/KU-1 (diol) and A3/KU-2 (3'-carbamate) were the most potent novobiocin analogues identified, based on their ability to inhibit Hsp90 and cause the degradation of phosphorylated AKT. As shown in FIG. 1, the most active compound identified in this assay was A4/KU-1 from the scheme above, which contains an N-acetyl side chain in lieu of the benzamide, lacks the 4-hydroxyl of the coumarin moiety, and has an unmodified diol. Structure-activity relationships for these compounds suggests that attachment of the noviose moiety to the 7-position of the coumarin ring is preferred for biological activity (B vs. D and E). Further, incorporation of the amide linker (A) resulted in greater inhibitory activity than the unsubstituted derivative, B. It is likely that the diol (4) mimics the ribose ring in the normal substrate (ATP) and may explain why replacement with a cyclic carbonate (1) or 2'-carbamate (2) resulted in decrease of activity.

Example 3

Degradation of Her-2

Figure 2:
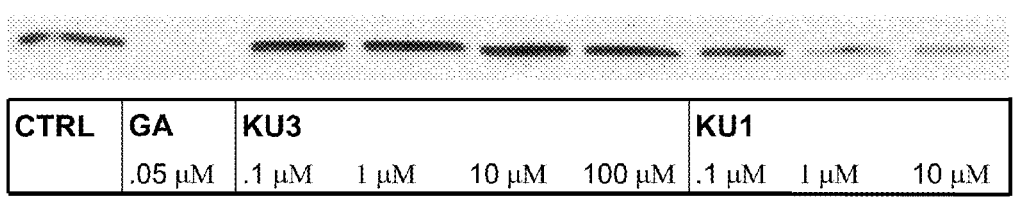
FIG. 2 is a western blot analysis of Skbr3 cells treated with novobiocin analogue denominated herein as KU-3/A2 (2'-carbamate) and KU-1/A4 (diol) for 24 hours. After incubation, the cells were harvested, lysed, and equal amounts of the protein lysates loaded into SDS wells. After electrophoresis, the gel was probed with Her-2 and actin (control) antibodies. The specific decrease in Her-2 levels is a result of Hsp90 inhibition that leads to Her-2 degradation.

The IC$_{50}$ for Hsp90 inhibitors is sometimes determined as the concentration of inhibitor required to produce 50% degradation of Her-2, another therapeutically important Hsp90 client protein involved in breast cancer. When KU-1/A4 was incubated with Skbr3 breast cancer cells at concentrations of 100 nM, 1 µM and 10 µM, a rapid decrease in Her-2 was observed between 100 nM and 1 µM, as shown in the Western blot of FIG. 2. These data are normalized against actin, a non-Hsp90 client protein, used as a control for non-specific degradation. These data suggest the IC$_{50}$ of KU-1/A4 is in the low micromolar range, whereas novobiocin in the same assay produces an IC$_{50}$ of 700 µM.

Example 4

Prostate Cancer

The steroid hormone receptors are also dependent upon the Hsp90 protein folding machinery for activation and hormone binding. To determine whether KU-1/A4 had similar effects on the androgen receptor, KU-1/A4 was tested in both a mutated androgen receptor-dependent prostate cancer cell line (LNCaP) and a wild type androgen receptor prostate cancer cell line (LAPC-4). More specifically, the prostate cancer cells were grown in RPMI with 10% fetal calf serum in a standard fashion. Once the cells had reached near confluence, they were treated with vehicle (DMSO) or varying concentrations of KU-1/A4 ranging from 10 nm to 100 µM for 24 hours. Cells were harvested and cell lysates prepared. Western blot analysis was then performed on the cell lysate utilizing commercially available antibodies against the androgen receptor, AKT, HIF-1α, Her2, and Hsp90. Actin was used as the control. More specifically, Western Blot analysis protein concentrations in serum samples were determined by the Pierce BCA protein assay kit according to the manufacturer's protocol. Western blot analysis (100 mg total protein/lane to start) was electrophoresed under reducing conditions on a SDS-PAGE gel. The separated proteins were transferred to a polyvinylidene difluoride membrane (Millipore, Bedford, Mass.) for 40 minutes at 80 V. The membranes were blocked for two hours at room temperature in Tris-buffered saline (pH 7.5) containing 0.2% I-block (Tropix, Bedford, Mass.), 1% milk, and 0.1% Tween-20 (TBS-T). The membranes were subsequently be incubated with a primary antibody to the above mentioned proteins (all of which have commercially available antibodies) overnight at 4° C. The next day the membrane was washed three times in TBS-T followed by one hour incubation with an appropriate horseradish peroxidase labeled secondary antibody in blocking buffer (TBS-T). The membranes were again washed in TBS-T and Tris-buffered saline and developed in SuperSignal West Pico Chemiluminescent Substrate (Pierce, Rockford, Ill.) according to manufacturer's instructions. The blots were visualized by exposing the enhanced chemiluminescence-reacted blot to X-ray film.

Figure 3:
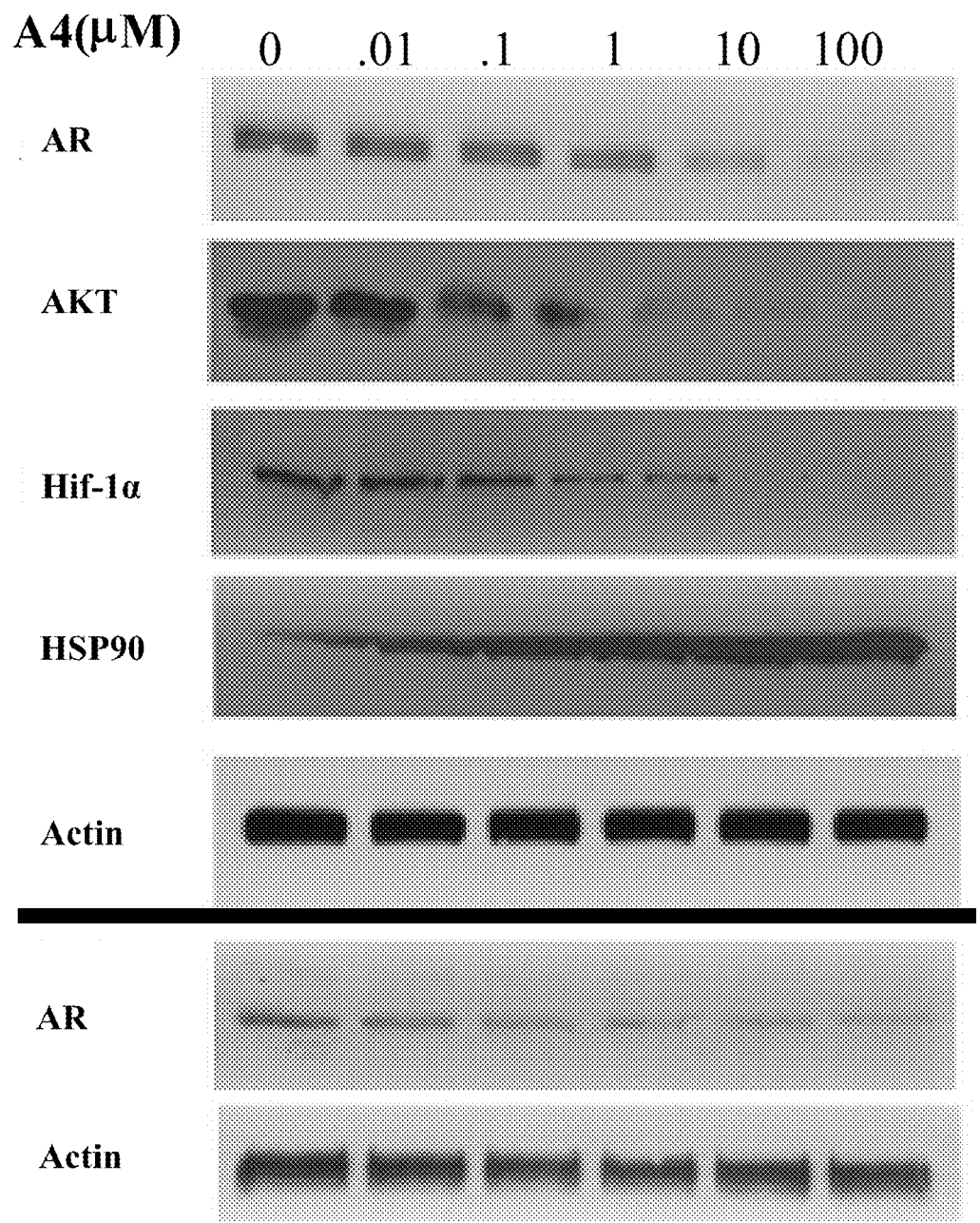
FIG. 3 (top panel) is a western blot analysis of prostate cancer LNCaP cells treated with KU-1/A4. The bottom panel is a western blot analysis of prostate cancer LAPC-4 cells incubated with KU-1/A4. Actin was used as a control in both assays.

As can be seen in FIG. 3, KU-1/A4 had a dramatic effect on the concentrations of the mutant androgen receptor, AKT, and HIF-1α at about 1 µM in the LNCaP cell line. In addition, KU-1/A4 drastically reduced levels of the androgen receptor at lower concentrations in the wild type androgen receptor prostate cancer cell line (LAPC-4). To verify that KU-1/A4 was not affecting other transcriptional or translational processes that could account for decreased protein, Hsp90 levels were determined. Under normal conditions, Hsp90 binds heat shock factor 1 (HSF1), but in the presence of Hsp90 inhibitors this interaction is lost and HSF1 is able to induce the expression of Hsp90. As can be seen in FIG. 3, Hsp90 levels are significantly increased in a manner dependent on the concentration of KU-1/A4 consistent with similar results previously obtained by incubation with geldanamycin and radicicol. Both of these data are in contrast to actin, which is not an Hsp90 client protein and thus remains unaffected by Hsp90 inhibitors.

Prophetic Example 4

Amide Side Chain Modifications

Since KU-1/A4 was shown to be the most potent C-terminal inhibitor of Hsp90 identified in Example 1, additional derivatives of the KU-1/A4 scaffold will be prepared. Modifications of the amide side chain will allow for an in depth study of the hydrophobic cavity that binds to this portion of KU-1/A4 and the analogous benzamide of novobiocin. As such, analogues of KU-1/A4 that have increasingly larger hydrophobic groups by the use of different commercially available or readily synthesized anhydrides, such as those anhydrides shown in the scheme below. See Khoo, L. E., Synthesis of Substituted 3-Aminocoumarins from Ethyl N-2-Hydroxyarylideneglycinates, *Syn. Comm.* 1999, 29, 2533-2538, which is incorporated by reference.

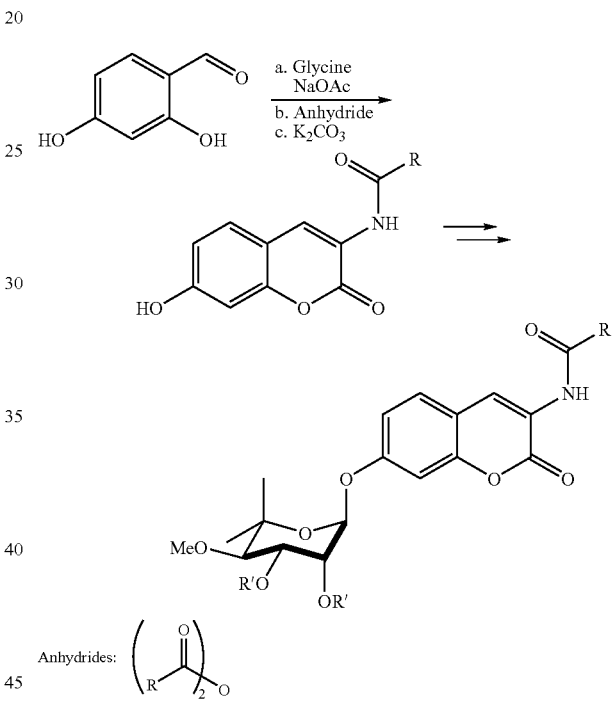

wherein in the scheme R is hydrogen, alkyl, alkenyl, alkynyl, aryl, carbocylic, heterocyclic, aryl, or aralkyl, (and most preferably R is hydrogen, alkyl, aryl, and aralkyl);

and wherein R' is hydrogen or CONH$_2$.

As part of this example, the amide linkage will also be reversed to determine the optimal profile of this functionality. As set forth in the scheme below, the 7-hydroxy-3-ethyl ester coumarin will be hydrolyzed to afford the corresponding acid, which will be coupled with amines that mimic the same side chains used in the KU-1/A4 amide studies for direct comparison of biological activity. Once coupled, the free phenols will be noviosylated as described earlier to afford the cyclic carbonate products. Treatment of the carbonate with methanolic ammonia will give the diol, 2- and 3-carbamoyl products as shown in the scheme below. See Shen et al., Synthesis of Photolabile Novobiocin Analogues, *Bioorg. Med. Chem. Lett.* 2004, 14, 5903-5906, which is incorporated by reference.

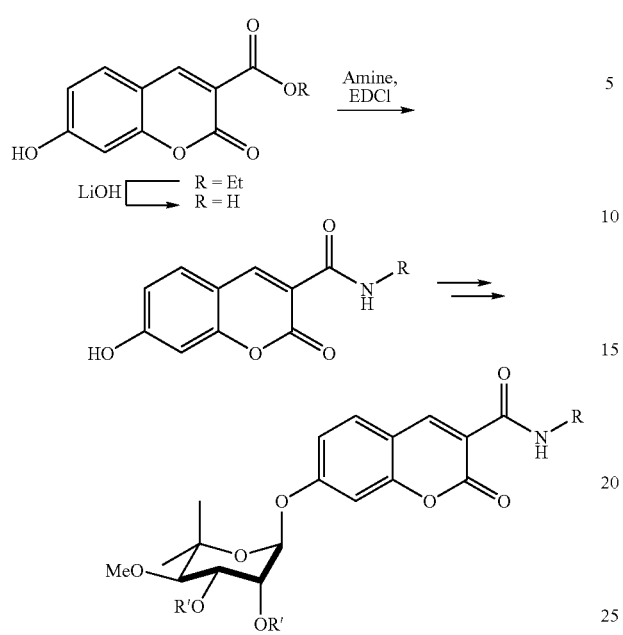

wherein in the scheme R is hydrogen, alkyl, alkenyl, alkynyl, aryl, carbocylic, heterocyclic, aryl, or aralkyl;

and wherein R' is hydrogen or $CONH_2$.

Most preferably, the R in the amide side chain is hydrogen alkyl, aryl, and alkaryl, and the amines used in the above scheme are $NH_3$, methylamine, ethylamine, propylamine, n-butylamine, and phenylamine. However, it will be appreciated to those skilled in the art that other derivatives can be prepared in accordance with the above scheme, in addition to the KU-1/A4 analogues shown. That is, the amide side chain, coumarin ring, and sugar may be modified in accordance with the other examples shown herein.

Prophetic Example 5

Isocoumarin Derivatives

To determine the most favorable interaction of the coumarin lactone with Hsp90, the isocoumarin derivative of the compounds of the present invention will be prepared. For example, with respect to KU-1/A4, the isocoumarin will be prepared from the 4-benzyloxylactone shown in the scheme below. Treatment of the lactone with sodium cyanide, followed by HCl/pyridine is known to produce similar isocoumarins. See Wells et al., Facile synthesis of 3-acylaminoisocoumarins, *J. Org. Chem.* 1971, 36, 1503-1506, which is incorporated by reference. Acylation of the amine followed by removal of the benzyl-protecting group will provide the phenol, which will be coupled with noviose trichloroacetimidate to afford the cyclic carbonate precursor. Ammoniaolysis of the cyclic carbonate will afford both the diol and 3'-carbamoyl products.

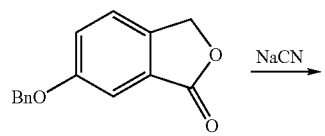

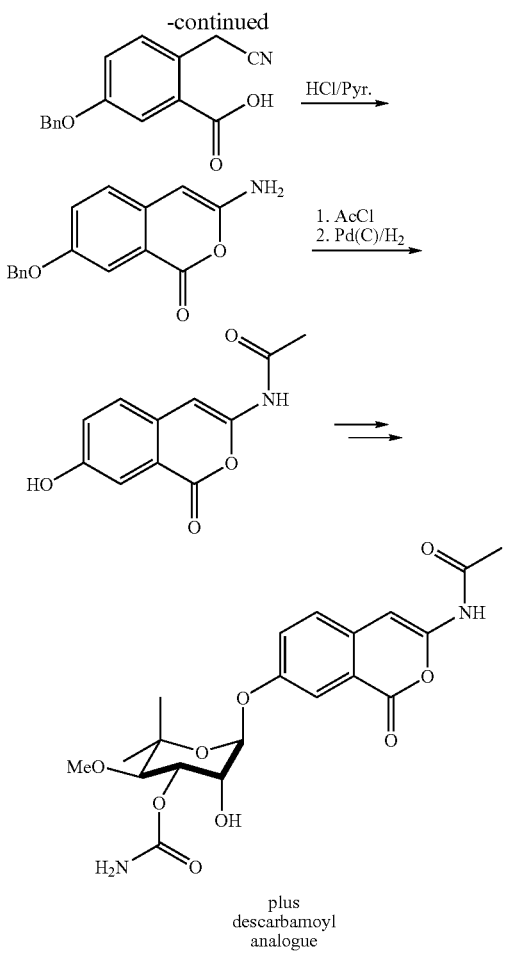

plus descarbamoyl analogue

It will be appreciated to those skilled in the art that other isocoumarin derivatives can be prepared in accordance with the above scheme, in addition to the KU-1/A4 analogue shown. That is, the amide side chain, coumarin ring, and sugar may be modified in accordance with the other examples shown herein.

Prophetic Example 6

Des(Dimethyl) and Desmethoxy Sugar Analogues

Modifications to the gem-dimethyl groups and the methyl ether on the noviose moiety will be prepared. In this example, the des(dimethyl) and desmethoxy sugar analogues will be prepared. Using KU-/1/A4 as an example in the scheme below, 2,3-O-isopropylidene-L-erythronolactol will be converted to the corresponding alkene by Wittig olefination. Dihydroxylation will afford the syn diol as noted in the earlier synthesis of noviose. See Yu et al., Synthesis of (−)-Noviose from 2,3-O-Isopropylidene-D-erythronolactol, *J. Org. Chem.* 2004, 69, 7375-7378. Protection of the primary alcohol, followed by alkylation of the secondary alcohol will afford the orthogonally protected molecule. Selective removal of the benzyl group and oxidation of the resultant alcohol will give the aldehyde. Treatment of this aldehyde with aqueous sulfuric acid will remove the acid-labile protecting groups while simultaneously promoting cyclization. Id.

Similarly, the desmethoxy compound will be prepared from the appropriately functionalized lactone (Stewart et al., 2-Deoxy-L-Ribose from an L-Arabino-1, 5-lactone, *Tetrahedron Assym.* 2002, 13, 2667-2672) by the addition of excess methyl Grignard to provide the primary and tertiary alcohol product. Oxidation of the primary alcohol will give the lactone, which will be reduced to the lactol before deprotection with aqueous sulfuric acid to yield the desmethoxy product. Once obtained, these sugars will be treated with carbonyl diimidazole to furnish the cyclic carbonates before coupling with the coumarin phenol. This set of conditions is based on previous work towards the preparation of novobiocin photoaffinity probes. See Shen et al., Synthesis of Photolabile Novobiocin Analogues, *Bioorg. Med. Chem. Lett.* 2004, 14, 5903-5906.

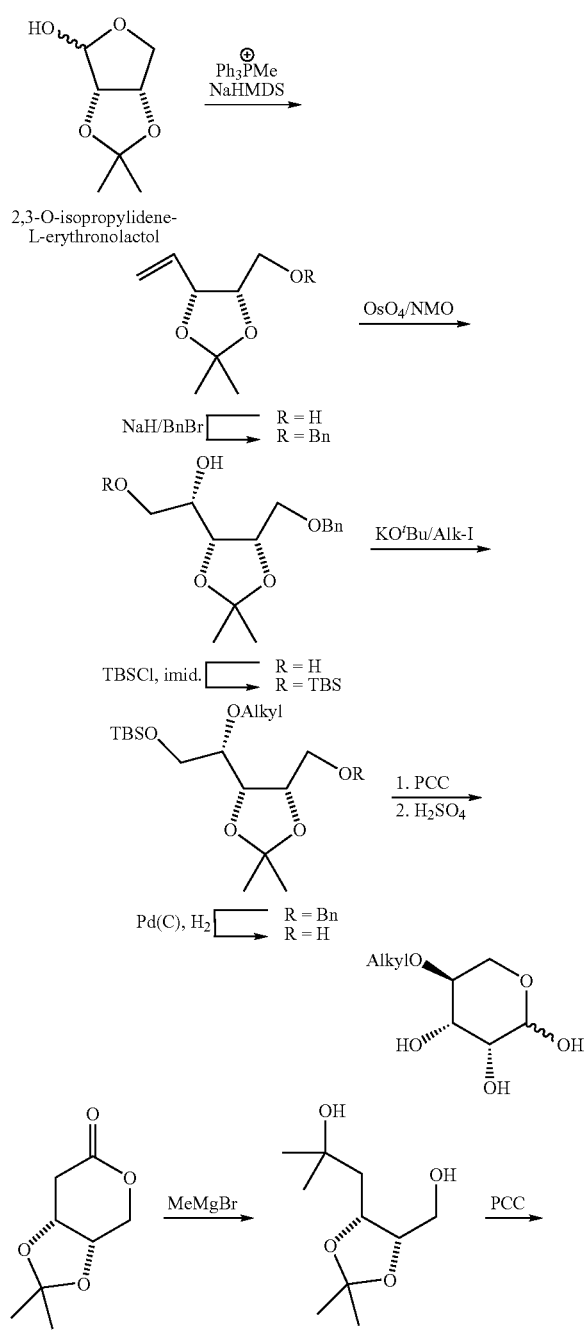

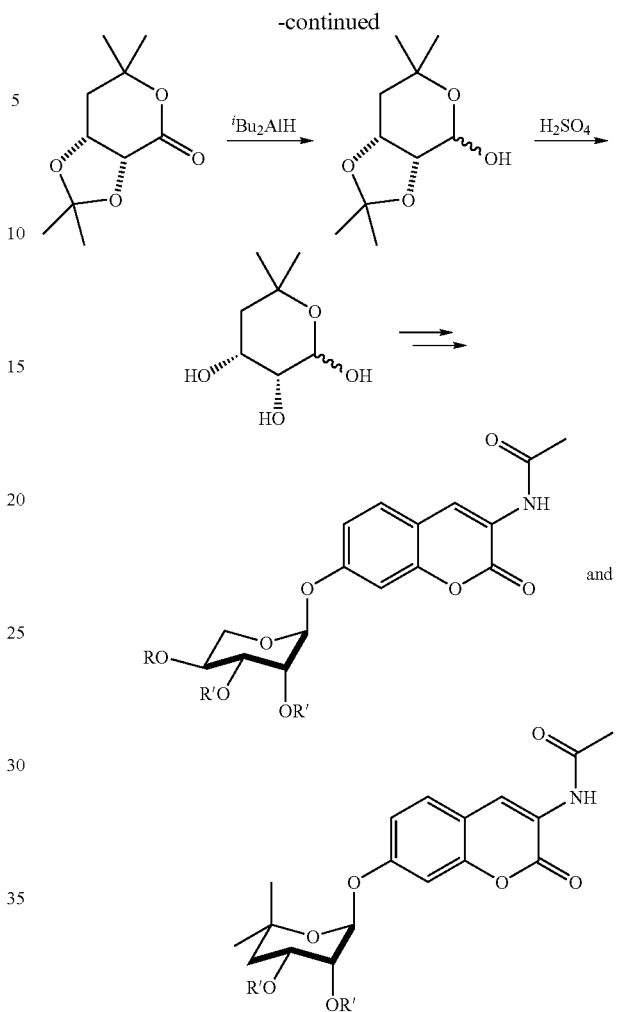

wherein preferably R is lower alkyl; and
wherein R' is preferably hydrogen or —CONH$_2$.

It will be appreciated that other demethylated an/or dealkoxylated derivatives can be prepared in accordance with the above scheme, in addition to the modified KU-1/A4 derivative shown above. That is, the amide side chain, coumarin ring, and sugar may be modified in accordance with the other examples shown herein.

Prophetic Example 7

Modified Novobiocin Derivatives

This example involves the modification to of the compounds of the present invention to complement the hydrogen bonding capabilities of the nucleotide bases (adenine and guanine) with those of the coumarin ring system as shown below. As an example, these analogues contain conformationally restricted hydrogen bond donors/acceptors of KU-1/A4 (F and G) and strategically placed hydrogen bond acceptors/donors to complement those found in guanine (H-L). In all cases, the hydrophobic pocket that accommodates the m-substituted benzamide ring of novobiocin will be probed by alteration of the side chain constituents. Although the schemes below are directed to preparing modifications of KU-1/A4, it will be appreciated to those skilled in the art, that the same modifications could be made in conjunction with other analogues described herein, such as the A-E compounds of Example 1.

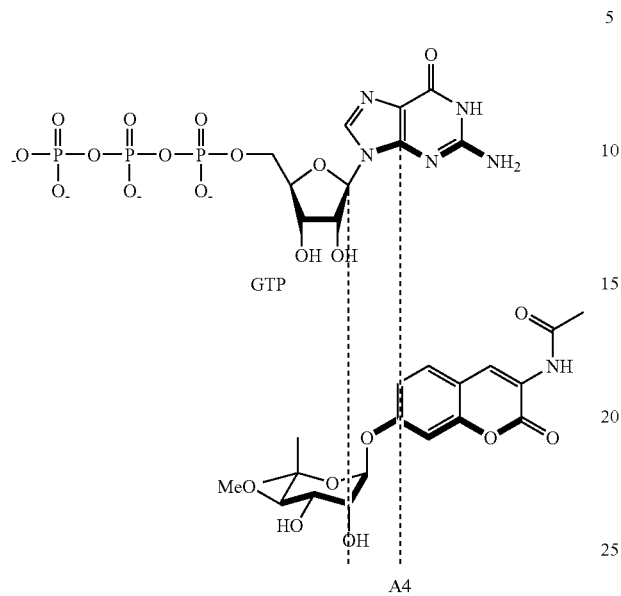

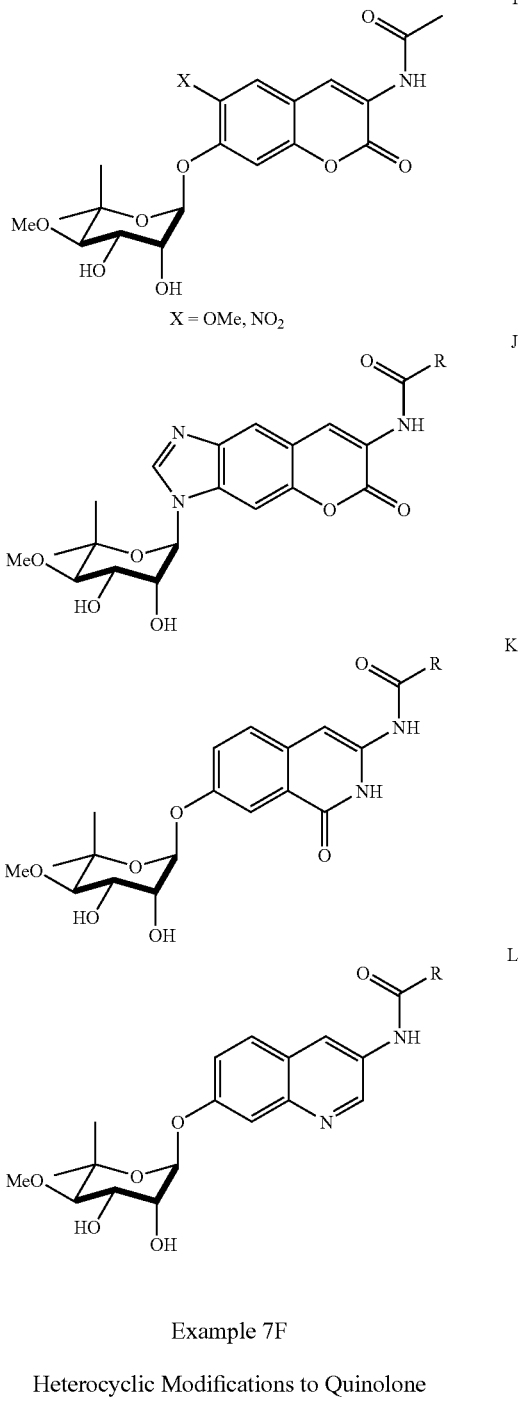

Example 7F

Heterocyclic Modifications to Quinolone

In this example, the coumarin ring will be modified to create F analogues that resemble guanine and contain a conformationally biased hydrogen-bond donor/acceptor. The synthesis begins with commercially available 4-hydroxy-2-nitrobenzaldehyde following the procedure of Meanwell, et al., Inhibitors of Blood Platelet cAMP Phosphodiesterase. 2. Structure-Activity Relationships Associated with 1,3-Dihydro-2H-imidazo[4,5-b]quinolin-2-ones Substituted with Functionalized Side Chains, *J. Med. Chem.* 1992, 35, 2672-2687. The phenol will be protected as the benzylether, followed by treatment with hydantoin phosphonate to give the corresponding olefin. See Meanwell et al., Diethyl 2,4-dioxoimidazolidine-5-phosphonate: A Wadsworth-Emmons Reagent for the Mild and Efficient Preparation of C-5 Unsaturated Hydantoins, *J. Org. Chem.* 1991, 56, 6897-6904. Reduction of the benzylether, nitro, and olefin functionalities will provide the appropriate amine for subsequent addition to the carbonyl upon treatment with iodine. Meanwell et al., Inhibitors of Blood Platelet cAMP Phosphodiesterase, Structure-Activity Relationships Associated with 1,3-Dihydro-2H-imidazo[4,5-b]quinolin-2-ones Substituted with Functionalized Side Chains, *J. Med. Chem.* 1992, 35, 2672-2687. As depicted earlier, the unmasked phenol will be coupled with the trichloroacetimidate of noviose carbonate, followed by removal of the carbonate moiety to furnish analogue F.

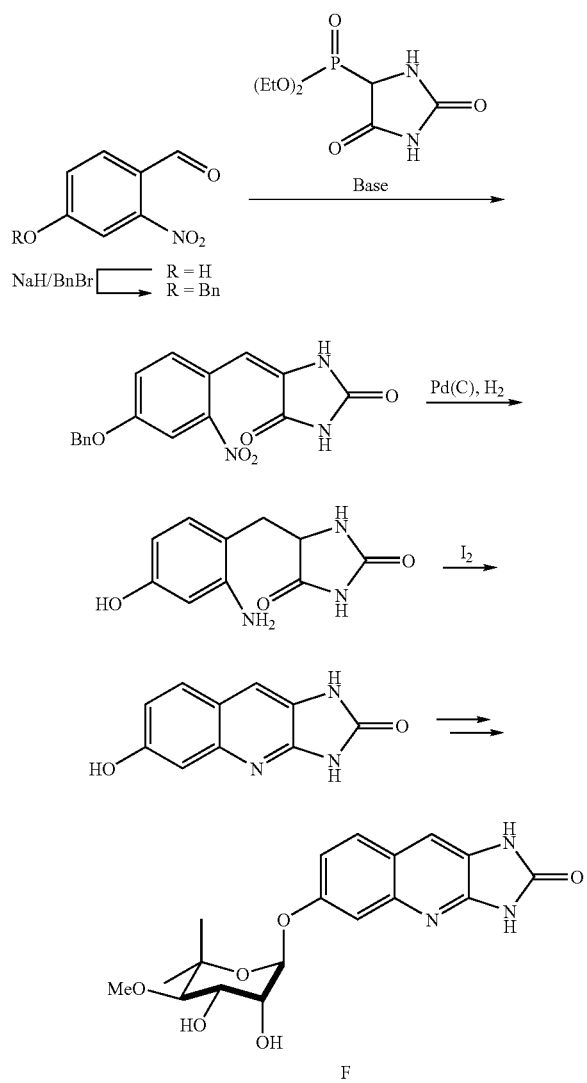

F

It will be readily appreciated to those skilled in the art that the foregoing scheme for the F analogues can be readily modified to prepare the following compounds, in addition to the oxidized imidazole attached to the quinolone shown above, by using commercially available or readily synthesized bases. Thus, the present invention encompasses novobiocin derivatives according to the formula:

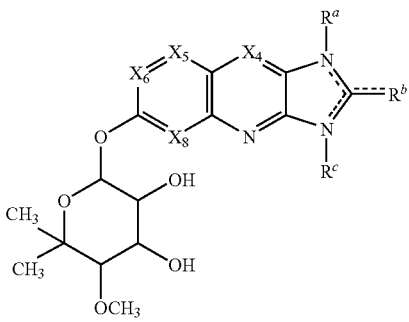

wherein $X_4$, $X_5$ $X_6$ $X_8$ are preferably each —CH—; and wherein $R^a$, $R^b$, and $R^c$ are independently hydrogen, alkyl, alkenyl, alkynyl, carbocyclic, heterocylic, aryl, or aralkyl; or wherein $R^b$ is oxided to form the carbonyl according to the formula:

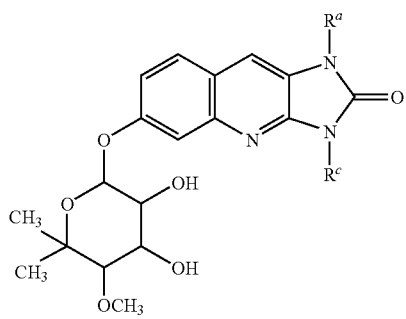

Example 7G

Heterocyclic Modifications

In this example, coumarin G will be prepared from 7-benzyloxy-4-hydroxy-3-nitrocoumarin, according to the scheme below. See Buckle et al., Aryloxyalkyloxy- and aralkyloxy-4-hydroxy-3-nitro coumarins which inhibit histamine release in the rat and also antagonize the effects of a slow reacting substance of anaphylaxis, *J. Med. Chem.* 1979, 22, 158-168. Treatment of the 4-hydroxyl group with phosphorous oxychloride ($POCl_3$) will afford the corresponding 4-amino derivative upon subsequent exposure to ammonia. See Rassochandran et al., Mild method for the preparation of 4-chloro-3-nitro coumarins, *Indian. J. Chem.* 1986, 25B, 328-329. Reduction of the nitro group, followed by reaction with triethyl orthoformate in the presence of acid will afford the desired compound. See Trkovnik et al., Synthesis of new heterocyclocoumarins from 3,4-diamino- and 4-chloro-3-nitrocoumarins, *Prep. Proced. Int.* 1987, 19, 450-455. Treatment of this 3,4-diamine with other commercially or readily available orthoesters (see McElvain et al., Ketene acetals. XVI. Phenylketene diethyl- and dimethylacetals from the pyrolysis of the corresponding orthoesters. *J. Am. Chem. Soc.* 1946, 68, 1917-1921) will provide a direct method for exploration of the hydrophobic pocket surrounding this moiety. The orthoesters readily condense with 1,2-diamines to produce the corresponding heterocylic compounds. Once prepared, these compounds will be coupled with noviose carbonate in analogous fashion to that shown in above to afford the corresponding G analogues of KU-1/A4.

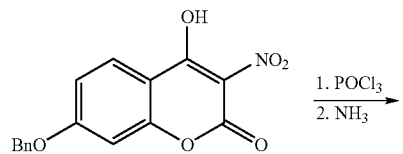

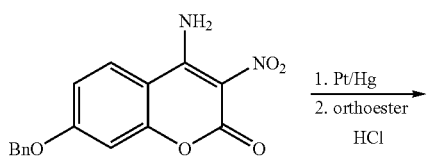

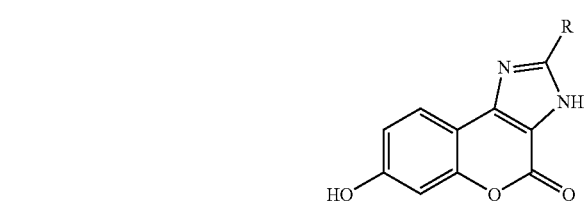

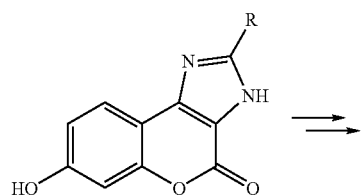

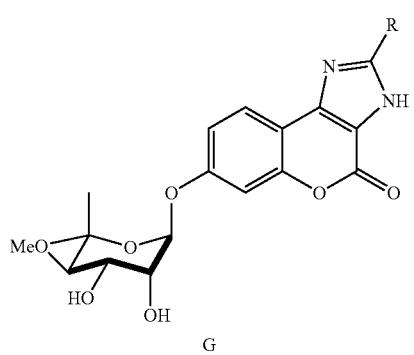

G orthoesters:

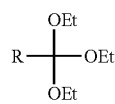

R = H, Me, Et, "Pr, "Bu, Bn

It will be readily appreciated to those skilled in the art that the foregoing scheme can be readily modified to prepare the following compounds, in addition to the imidazole shown above by using different orthoesters.

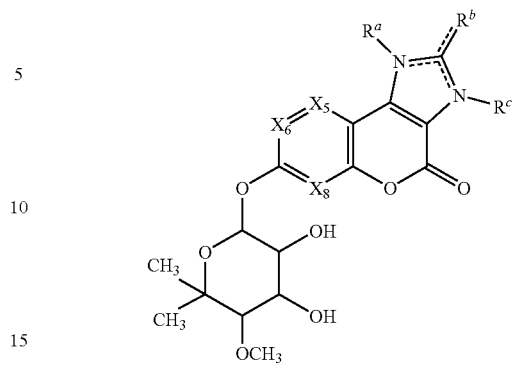

wherein $X_5$ $X_6$ $X_8$ are preferably each —CH—; and wherein $R^a$, $R^b$, and $R^c$ are independently hydrogen, alkyl, alkenyl, alkynyl, carbocyclic, heterocyclic, aryl, or aralkyl; or wherein $R^b$ is oxided to form the carbonyl according to the formula:

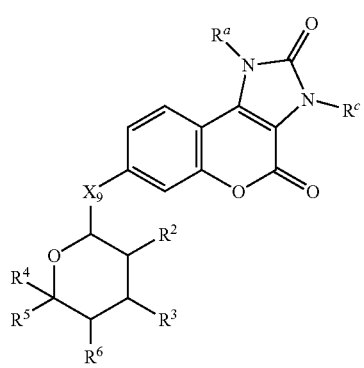

Example 7H

The nitrogen-containing H variants of the coumarin ring will be prepared from 2-methyl-3,5-pyridinediol, by bromination of the benzylic methyl group, followed by hydrolysis and oxidation to the corresponding aldehyde as set forth in the scheme below. See Morisawa et al., Anticoccidal agents. IV. Modification at the 5-position of 4-deoxypyridoxol and α4-norpyridoxol, *Agric. Biol. Chem.* 1975, 39, 1275-1281. Using conditions previously employed for the syntheses of other coumarin derivatives by us, the aldehyde will be treated with glycine under basic conditions to yield the azacoumarin ring system. See Billeret et al., Convenient synthesis of 5-azacoumarins, *J. Hetero. Chem.* 1993, 30, 671-674. Acylation of the amine with various anhydrides will furnish the acylated 7-hydroxyl and 4-amino derivatives, of which the 7-phenolic ester can be readily cleaved by subsequent treatment with potassium carbonate in methanol. The resulting phenol will be coupled with noviose carbonate as described earlier.

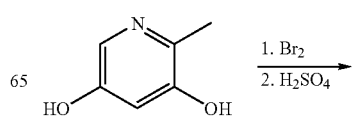

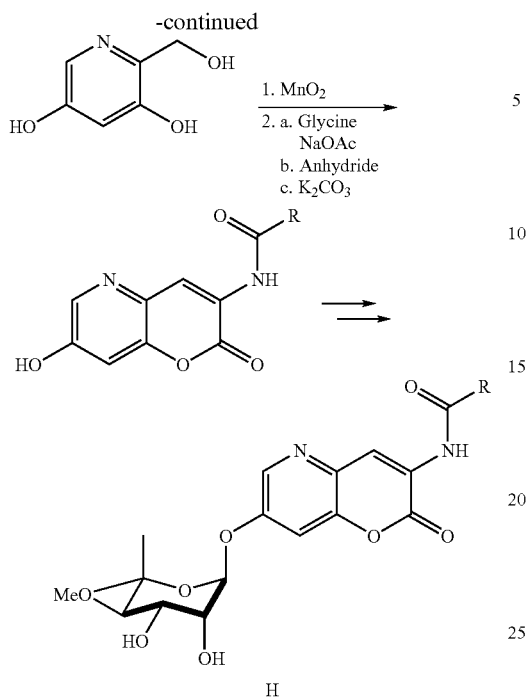

Anhydrides:

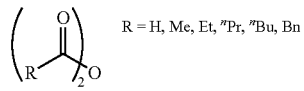

R = H, Me, Et, ⁿPr, ⁿBu, Bn

While the scheme above illustrates the modified coumarin of KU-1/A4 with a limited number of amide side chain substitutions, it will be appreciated to those skilled in the art that other derivatives can be prepared in accordance with the above scheme, in addition to the KU-1/A4 analogues shown. That is, the amide side chain, coumarin ring, and sugar may be modified in accordance with the other examples shown herein.

Example 7I

Coumarin Side Chains

The I analogues are directed to other side-chains extending from the coumarin ring. As an example, the KU-1/A4 coumarin ring will be prepared from 2,4-dihydroxy-5-nitrobenzaldehyde (see Chandrashekhar et al., g-substitution in the resorcinol nucleus, VI. Formylation of 4-nitro and 2-nitro resorcinols, *Proc. Ind. Acad. Sci.* 1949, 29A, 227-230) and 2,4-dihydroxy-5-methoxybenzaldehyde (Demyttenaere et al., Synthesis of 6-methoxy-4H-1-benzopyran-7-ol, a character donating component of the fragrance of *Wisteria sinensis*, *Tetrahedron* 2002, 58, 2163-2166) according to the procedure of Khoo et al., Synthesis of substituted 3-aminocoumarins from ethyl N-2-Hydroxyarylideneglycinates, *Syn. Commun.* 1999, 29, 2533-2538, as generally set forth in the scheme below. The o-hydroxybenzaldehyde will be treated with ethyl glycine under acidic conditions to afford the corresponding free amine upon basic workup. Both the amino and hydroxyl functionalities will be acylated with the same anhydrides as shown above. Subsequent hydrolysis of the phenolic ester will provide the coumarin amide, which can be coupled directly with noviose carbonate as described previously.

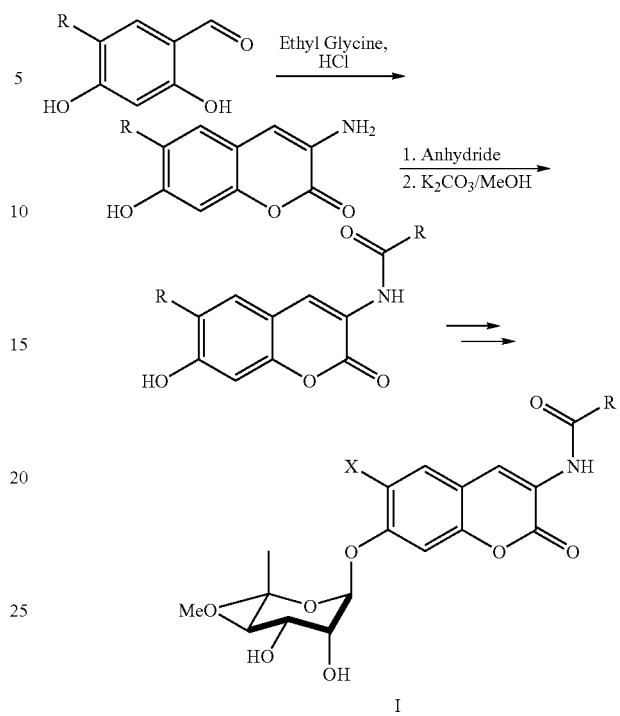

wherein in the scheme R is hydrogen, alkyl, alkenyl, alkynyl, aryl, carbocylic, heterocyclic, aryl, or aralkyl;

wherein X is alkyl, alkenyl, alkynyl, aryl, aralkyl, alkoxy, halogen or nitro.

Again, while the scheme above illustrates the modified coumarin ring of KU-1/A4 with a limited number of amide side chain substitutions, it will be appreciated to those skilled in the art that other derivatives can be prepared in accordance with the above scheme, in addition to the KU-1/A4 analogues shown. That is, the amide side chain, coumarin ring, and sugar may be modified in accordance with the other examples shown herein.

Example 7J

Heterocycles

The J analogues will be prepared from 4-chloro-2-hydroxy-5-nitrobenzaldehyde (see Pal et al., New arylsulfonylhydrazones of substituted benzaldehyde as anticancer agents, *Neoplasms* 1983, 30, 551-556) by treatment with glycine, acetic anhydride, and sodium acetate as mentioned previously for the preparation of other coumarin derivatives as set forth in the following scheme. See Khoo et al., Synthesis of substituted 3-aminocoumarins from ethyl N-2-Hydroxyarylideneglycinates, *Syn. Commun.* 1999, 29, 2533-2538. The chloro substituent will undergo nucleophilic aromatic displacement with ammonia as a consequence of the electron withdrawing p-lactone and o-nitro group. Upon formation of the 7-amino-6-nitrocoumarin, the nitro group will be reduced and immediately treated with triethyl orthoformate to produce the imidazole ring that resembles guanine. See Buckle et al., Aryloxyalkyloxy- and aralkyloxy-4-hydroxy-3-nitro coumarins which inhibit histamine release in the rat and also antagonize the effects of a slow reacting substance of anaphylaxis, *J. Med. Chem.* 1979, 22, 158-168.

Subsequent treatment with lithium diisopropylsilylamide and trimethylsilyl trifluorosulfonic acid will provide the TMS-protected diaza compound. See Vorbruggen et al., *Organic Reactions*, Volume 55, 2000, John Wiley and Sons, NY. pp 12-14 and references therein. The trichloroacetimidate of noviose carbonate will be added to a solution of this TMS-protected coumarin followed by addition of trifluoroacetic acid to afford the coupled product. Upon exposure of the cyclic carbonate to triethylamine in methanol, the resulting diol will be produced in a similar fashion as was used to make KU-1/A4 directly from the corresponding cyclic carbonate.

Example 7K

The K analogues of the KU-1/A4 coumarin moiety will be prepared from 5-methoxy-2-methylbenzonitrile as set forth in the scheme below. See Tomita et al., Schmidt reaction with benzocycloalkenones, *J. Chem. Soc. C: Organic* 1969, 2, 183-188. Bromination of the benzylic methyl group, followed by displacement with potassium cyanide will furnish the dinitrile product, which is a substrate for acid catalyzed cyclization to form the corresponding 2-bromoisoquinoline. See Johnson et al., The cyclization of dinitriles by anhydrous halogen acids. A new synthesis of isoquinolines, *J. Org. Chem.* 27, 3953-3958. Acylation of the free amine with the anhydrides shown in Scheme 4 will furnish the amide products, which will be treated with dilute hydrochloric acid to produce the isoquinolone. As before, the free phenol will be coupled with noviose carbonate trichloroacetimidate, followed by removal of the cyclic carbonate to furnish K and its acylated (R) derivatives.

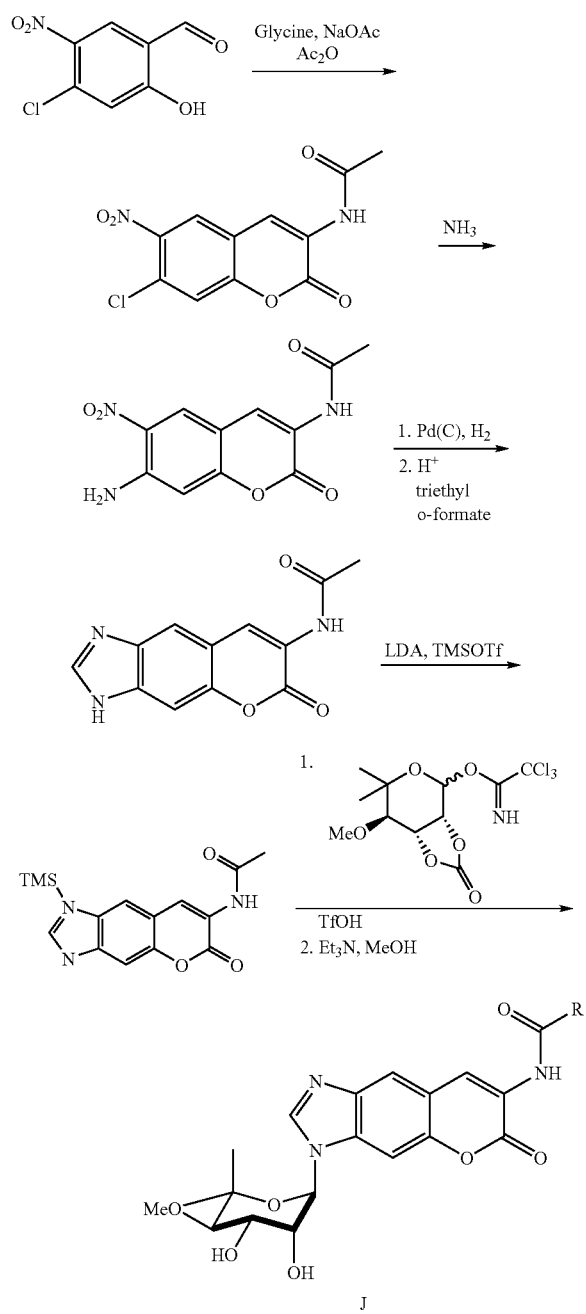

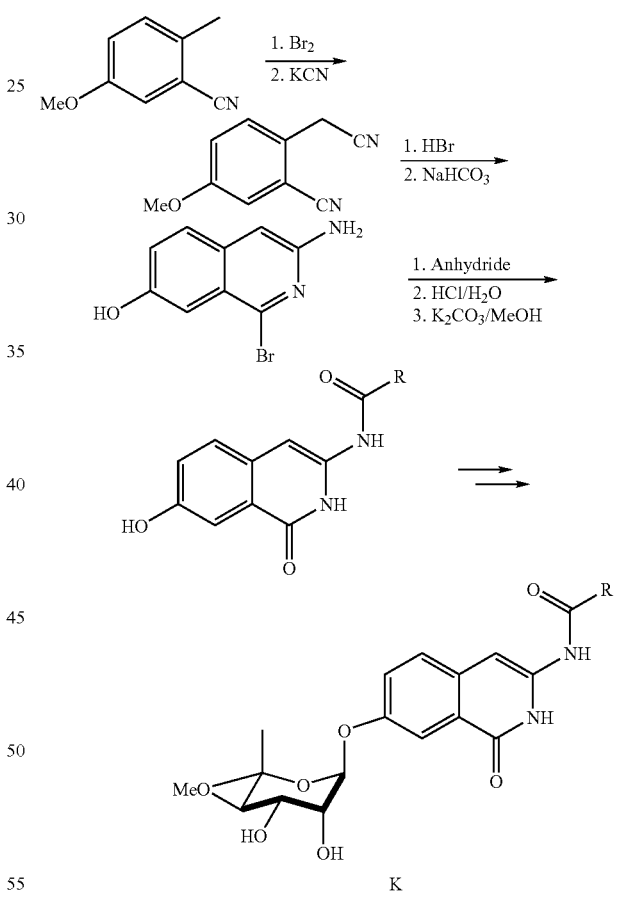

wherein R is hydrogen, alkyl, alkenyl, alkynyl, aryl, carbocyclic, heterocyclic, aryl, or aralkyl.

Again, while the scheme above illustrates the modified coumarin ring of KU-1/A4 with a limited number of amide side chain substitutions, it will be appreciated to those skilled in the art that other derivatives can be prepared in accordance with the above scheme, in addition to the KU-1/A4 analogues shown. That is, the amide side chain, coumarin ring, and sugar may be modified in accordance with the other examples shown herein.

Example 7L

Quinolines

Quinoline derivatives of, L, will be prepared from 7-hydroxyquinoline, by first bromination of the quinoline ring, see Zymalkowski et al., Chemistry of 3-quinolinecarboxaldehyde, *Ann. Chem., Justis Liebigs* 1966, 699, 98-106, followed by a copper-catalyzed amination of the halogenated heterocycle as set forth in the scheme below. See Lang et al., Amination of aryl halides using copper catalysis, *Tetrahedron Lett.* 2001, 42, 4251-3254. Subsequent treatment with various anhydrides (shown previously), followed by hydrolysis of the phenolic ester and coupling with noviose carbonate will ultimately afford these L analogues.

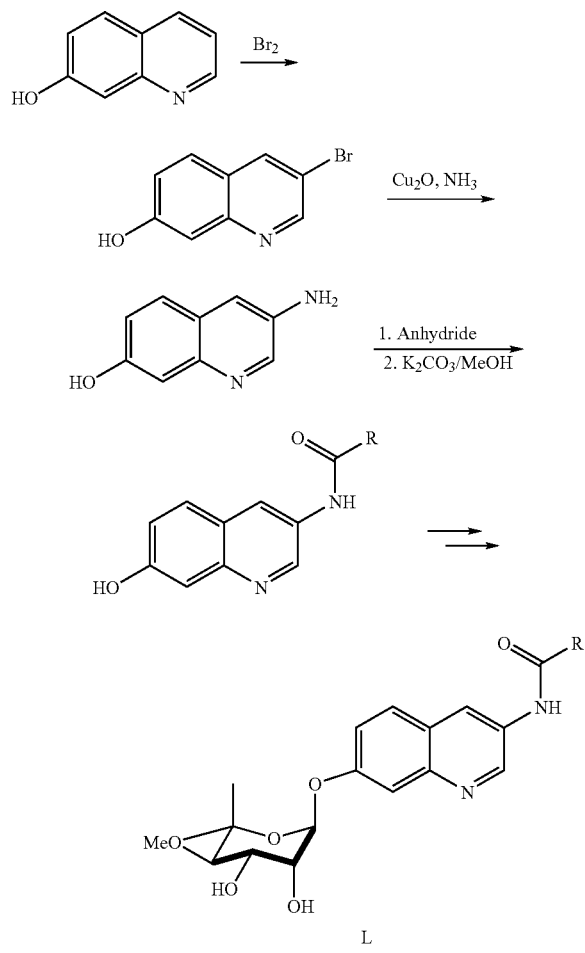

wherein R is hydrogen, alkyl, alkenyl, alkynyl, aryl, carbocyclic, heterocyclic, aryl, or aralkyl.

Again, while the scheme above illustrates the modified coumarin ring of KU-1/A4 with a limited number of amide side chain substitutions, it will be appreciated to those skilled in the art that other derivatives can be prepared in accordance with the above scheme, in addition to the KU-1/A4 analogues shown. That is, the amide side chain, coumarin ring, and sugar may be modified in accordance with the other examples shown herein.

Prophetic Example 8

Chlorobiocin Analogues

This example involves the modification of the carbohydrate reside. More specifically, analogues similar to that of novobiocin's chlorinated pyrollic ester, chlorobiocin, will be prepared.

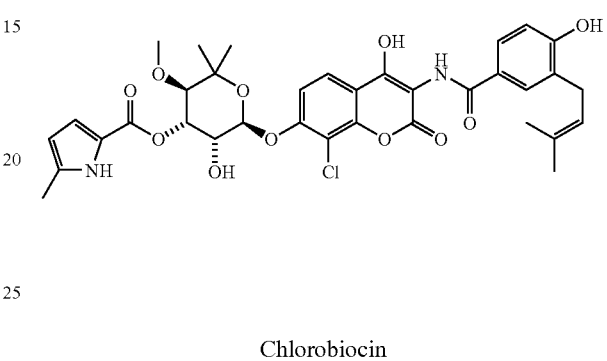

Chlorobiocin

As an example, compound KU-1/A4 will be prepared, and then coupled with a variety of acids to selectively afford the equatorial acylated alcohols. Selective acylation is based upon previous studies aimed at the preparation of photolabile derivatives of novobiocin. See Shen et al., Synthesis of Photolabile Novobiocin Analogues, *Bioorg. Med. Chem. Lett.* 2004, 14, 5903-5906, which is incorporated by reference. These acids will include the pyrrolic acid found in chlorobiocin as well as several other that are shown in the scheme below. Exemplary acids include pyrrolic acids, indolic acids, pyridinic acids, benzoic acids, salicylic acid, para-hydrobenzoic acid, thiobenzoic acid, and pyrazolic acid. In one aspect, the sugar will be modified to include a functional group according to the formula —R'—OR", wherein R' is a covalent bond or alkyl, and R" is an acyl group. Most preferably, the acyl derivative comprises the group —COR wherein R is alkyl, aryl, aralkyl, or an aromatic heterocyclic group. Alkylated, aralkylated, thiolated, halogenated, and hydroxylated pyroles, indoles, pyridines, and pyrazoles are attached to the sugar ring as shown in the scheme below.

In another aspect, various substitutents will be added to the amine of the carbamate side chain. As an example, carbonate KU-9/A1 will be prepared and amines added to provide the 3'-carbamoyl products as generally set forth in the scheme below. Thus, in one aspect the sugar will be modified to include a functional group according to the formula —R'OR", wherein R' is a covalent bond or alkyl, and R" is C-amido. Most preferably, the C-amido group is —CONR'R" wherein R' is H, and R" is alkyl, aryl, aralkyl, or an aromatic heterocyclic group. Pyroles, halogenated benzyls and pyridines, and alkyl groups are shown as the modified side chain of the sugar in the scheme below.

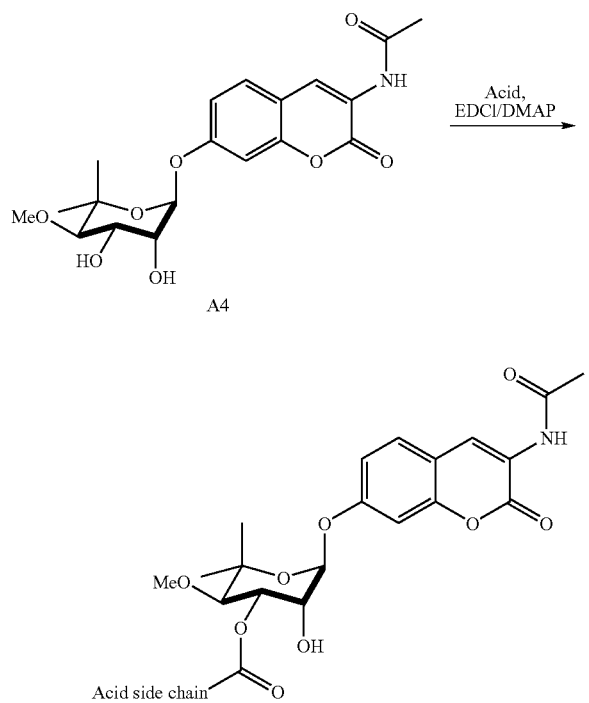

A4

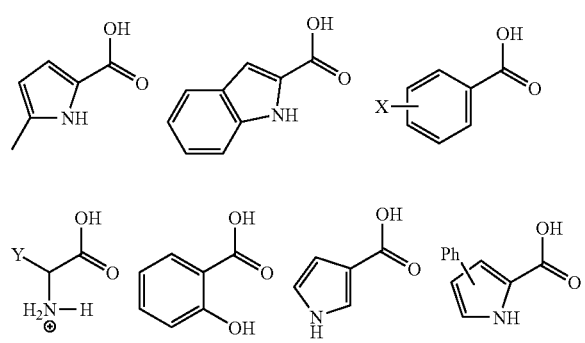

Acids:

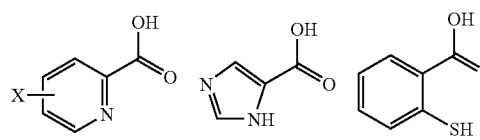

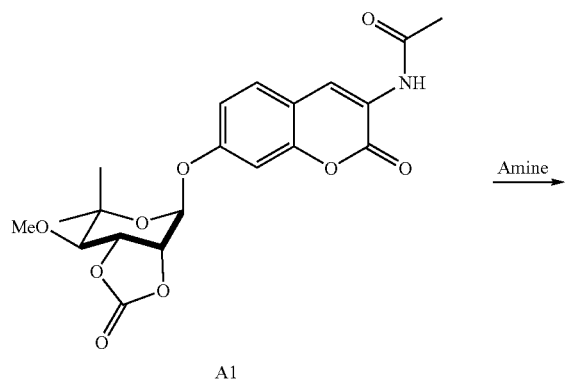

A1

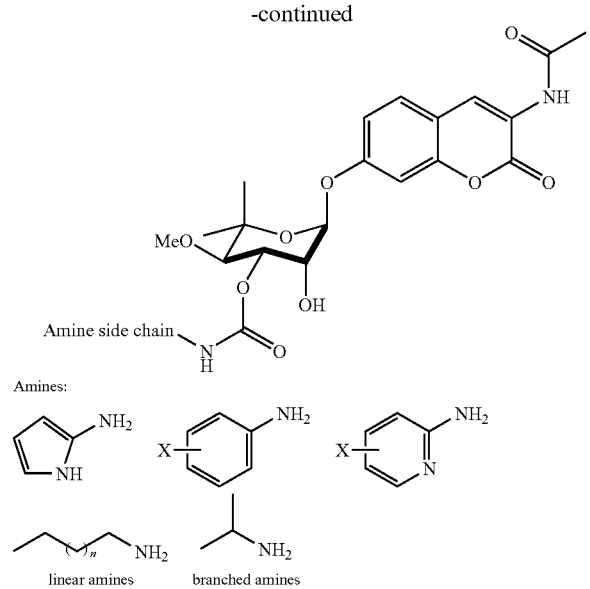

Wherein X is alkyl, alkenyl, alkynyl, hydroxyl, halo, and n is an integer, preferably 0, 1, 2, 3, or 4.

Prophetic Examples 9-11

Furanose and Pyranose Novobiocin Derivatives

In this example, new pyranose and furanose derivatives will be prepared that have affinity with the sugar of GTP and phosphate binding region of Hsp90. These selected compounds are shown in below and include ester, amide, sulfonic ester, phosphonic ester, carbamoyl, sulfonamide, and hydroxyl derivatives. Initial compounds will be coupled with the coumarin ring present in KU-1/A4, but when a more potent analogue is obtained, the best sugar derivative from these studies will be placed onto the optimized ring system.

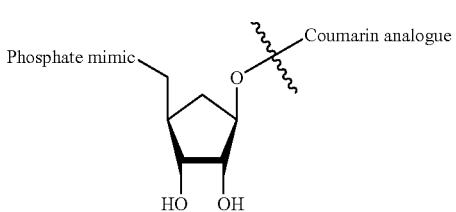

Furanose Derivatives

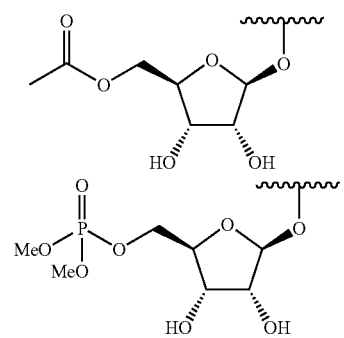

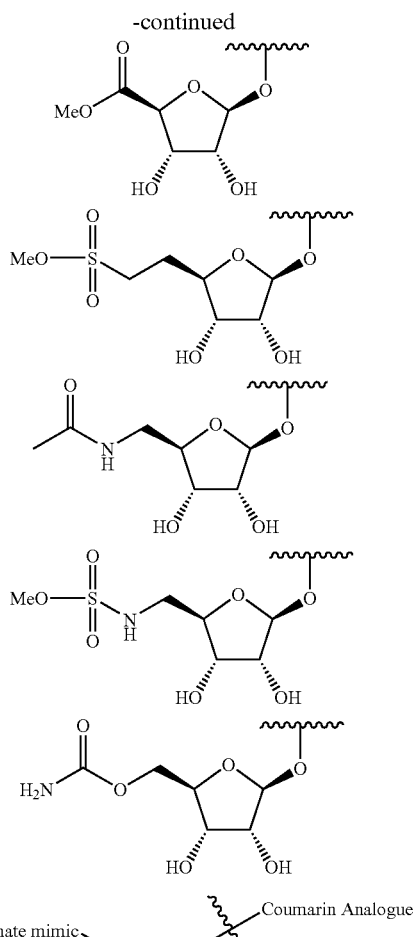

Pyranose Analogues

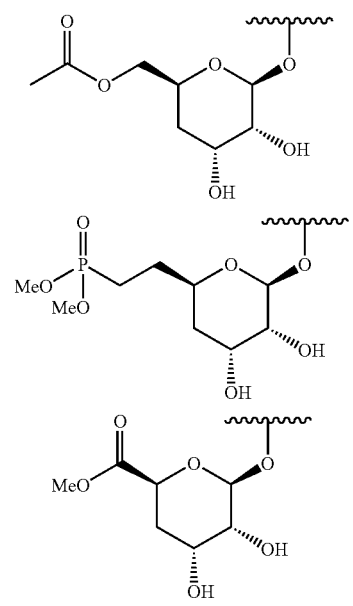

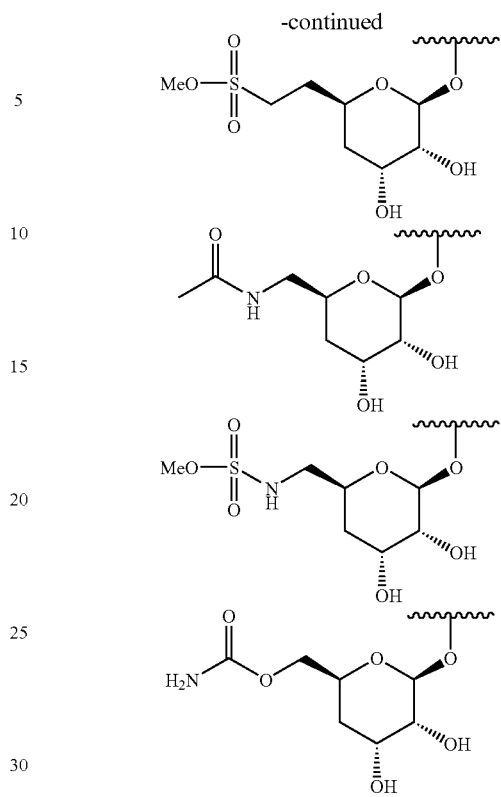

Examples 9 and 10

Synthesis of Furanose Derivatives

The o-acetyl derivative will be prepared from ribose (9.1, Scheme 9). Treatment of the ribose hemiacetal with benzyl alcohol and hydrochloric gas will provide the benzyloxyacetal, 9.2. See Pigro et al., Readily available carbohydrate-derived imines and amides as chiral ligands for asymmetric catalysis, *Tetrahedron* 2002, 58, 5459-5466.

Subsequent reaction with carbonyl diimidazole will furnish the 2,3-cyclic carbonate (9.3), (See Peixoto et al., Synthesis of Isothiochroman 2,2-dioxide and 1,2-benzoxathiin 2,2-dioxide Gyrase B Inhibitors, *Tetrahedron Lett.* 2000, 41, 1741-1745) allowing the primary alcohol to react with acetyl chloride in the following step. Debenzylation, followed by conversion to the trichloroacetimidate 9.5 (See Peixoto et al., Synthesis of Isothiochroman 2,2-dioxide and 1,2-benzoxathiin 2,2-dioxide Gyrase B Inhibitors, *Tetrahedron Lett.* 2000, 41, 1741-1745) will furnish a suitable substrate for coupling with the KU-1/A4 coumarin ring system. As noted in previous work, coupling of trichloroacetimidates with phenols in the presence of catalytic boron trifluoride affords one stereoisomer (9.6), which results from attack of the intermediate oxonium species away from the sterically crowded cyclic carbonate. See Shen et al., Synthesis of Photolabile Novobiocin Analogues, *Bioorg. Med. Chem. Lett.* 2004, 14, 5903-5906. It has been previously observed that treatment of similar cyclic carbonates with methanolic triethylamine readily provides the corresponding diol products (9.7) in high yields (>80%).

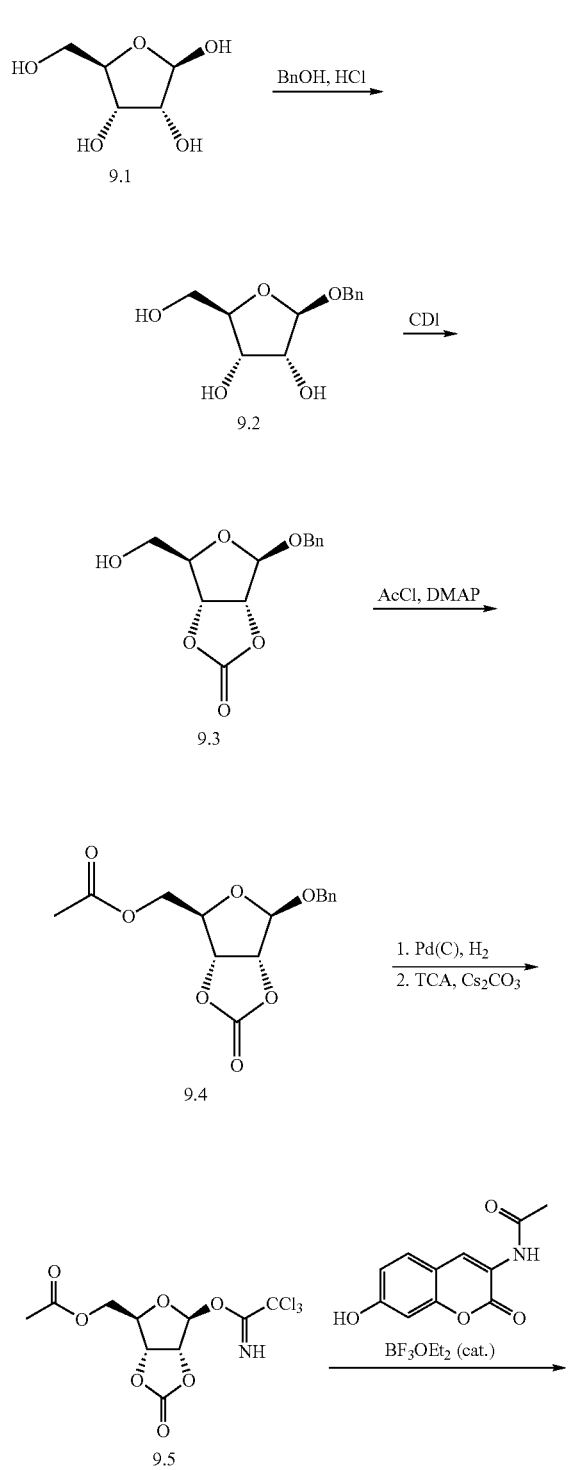

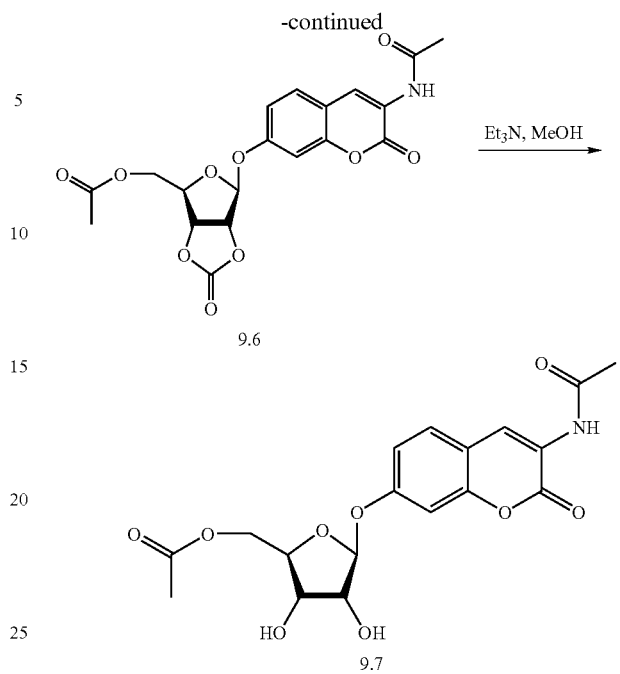

The remaining furanose derivatives will be prepared from benzyl-protected ribose carbonate (9.3, Scheme 10). Both the sulfonamide and N-acetyl analogues will be furnished by conversion of primary alcohol (9.3) to the corresponding azide by a Mitsunobu reaction with bis(azido)zinc pyridine complex. Viaud et al., Zinc azide mediated Mitsunobu substitution. An expedient method for the one-pot azidation of alcohols, *Synthesis* 1990, 130-132. The resulting azide (10.1) will be reduced, and the primary amine converted to the sulfonamide and N-acetyl functionalities, 10.2 and 10.3, respectively. Hansson et al., Synthesis of Beta-benzyl N-(tert-butoxycarbonyl)-L-erythro-Beta-(benzyloxy)aspartate from (R,R)-(+)-tartaric acid, *J. Org. Chem.* 1986, 51, 4490-4492. To prepare methyl ester 10.4, the free alcohol will be oxidized directly to the acid, followed by methylation. Carbamate 10.5 will also be prepared from the same alcohol, simply by treatment with trichloroacetyl isocyanate according to the procedure of Kocovsky, Carbamates: a method of synthesis and some synthetic applications, *Tetrahedron Lett.* 1986, 27, 5521-5524. Both the sulfonic ester and the phosphonic ester will be prepared by conversion of 9.3 to iodide 10.6, followed by generation of the requisite enolate to displace the halide. Callant et al., An efficient preparation and the intramolecular cyclopropanation of Beta-diazo-Beta-ketophosphonates and Beta-diazophosphonoacetates, *Syn. Commun.* 1984, 14, 155-161. Subsequent treatment with palladium (0) and an amine will lead to allyl removal followed by decarboxylation to form 10.10 and 10.8. See Guibe, Allyl esters and their use in complex natural product syntheses, *Tetrahedron* 1998, 54, 2967-3041.

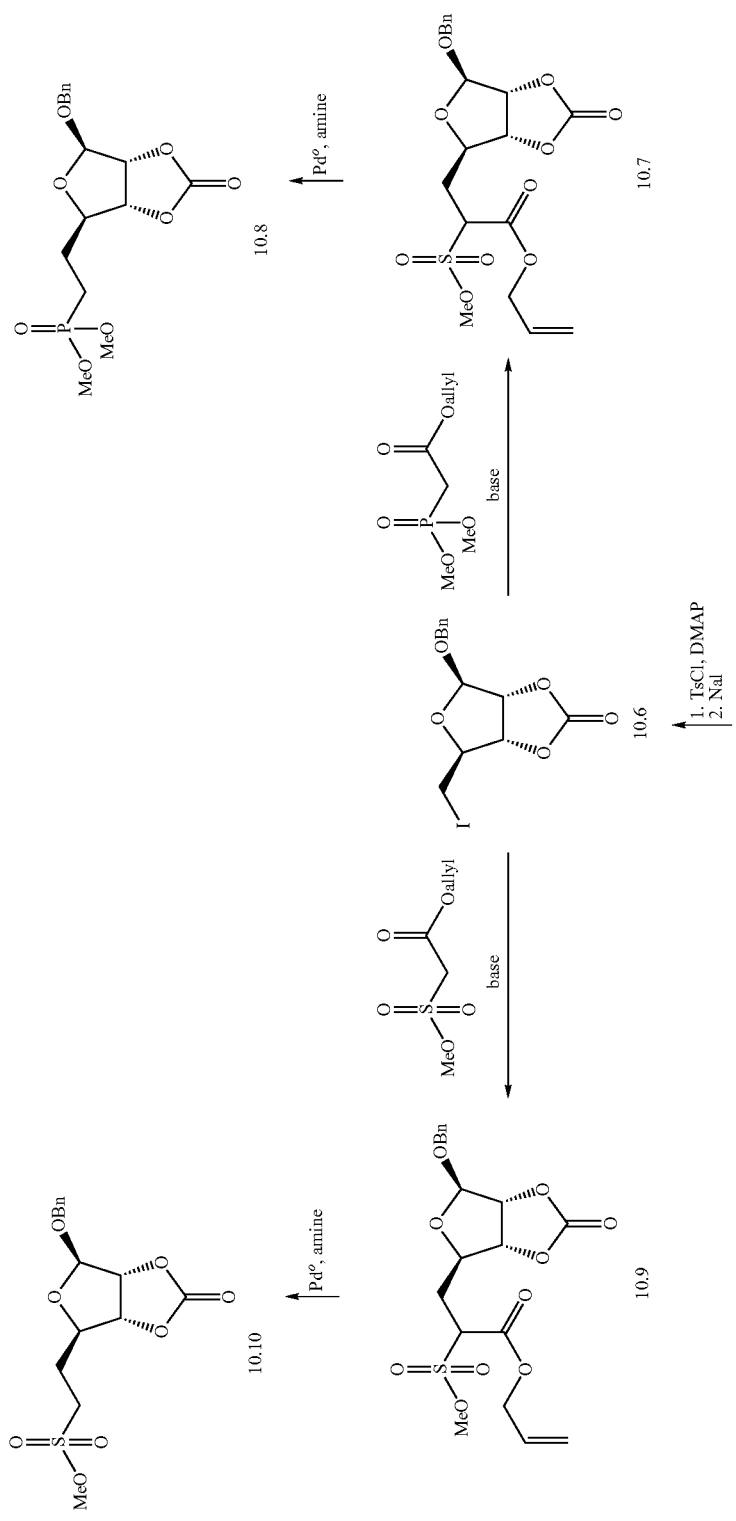

-continued
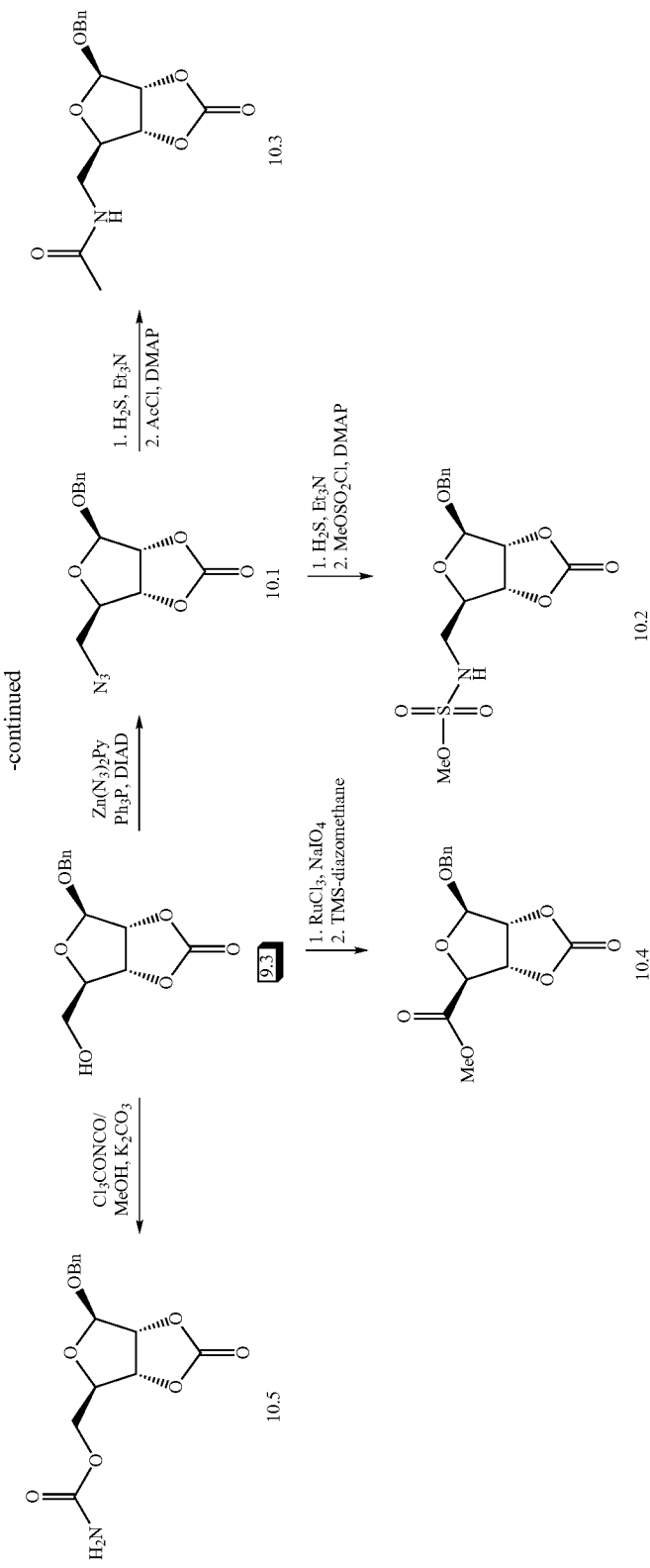

Example 11

Synthesis of Pyranose Derivatives

The pyranose derivatives, which resemble noviose and a ring-expanded ribose ring, will be prepared by our recently reported synthesis of 11.1. See Yu et al., Synthesis of Mono- and dihydroxylated furanoses, pyranoses, and an oxepanose for the Preparation of Natural Product Analogue Libraries, *J. Org. Chem.* 2005, 70, 5599-5605, which is incorporated by reference in its entirety. The pyranose derivatives will be prepared in a similar manner from the known dihydropyrone (See Ahmed et al., Total synthesis of the microtubule stabilizing antitumor agent laulimalide and some nonnatural analogues: The power of Sharpless' Asymmetric Epoxidation, *J. Org. Chem.* 2003, 68, 3026-3042), which is available in four steps from commercially available triacetyl D-glucal (Roth et al., Synthesis of a chiral synthon for the lactone portion of compactin and mevinolin, *Tetrahedron Lett.* 1988, 29, 1255-12158). The pyranose will be furnished by Sharpless asymmetric dihydroxylation (SAD) of the olefin to give the product in high diastereomeric excess (Kolb et al., Catalytic Asymmetric Dihydroxylation, *Chem. Rev.* 1994, 94, 2483-2547), which can be converted to the cyclic carbonate at a later time.

Reduction of the lactone with diisobutylaluminum hydride will give lactol 11.2, which upon treatment with benzyl alcohol and hydrochloric gas will give the benzyloxyacetal 11.3. Similar studies have been used to prepare noviose from arabinose using an identical sequence of steps. See Peixoto et al., Synthesis of Isothiochroman 2,2-dioxide and 1,2-benzoxathiin 2,2-dioxide Gyrase B Inhibitors, *Tetrahedron Lett.* 2000, 41, 1741-1745. The corresponding diol will be treated with carbonyl diimidazole to yield cyclic carbonate 11.4. The primary alcohol will be converted to the same functionalities as shown in the scheme above, using the chemistry depicted for the furanose derivatives.

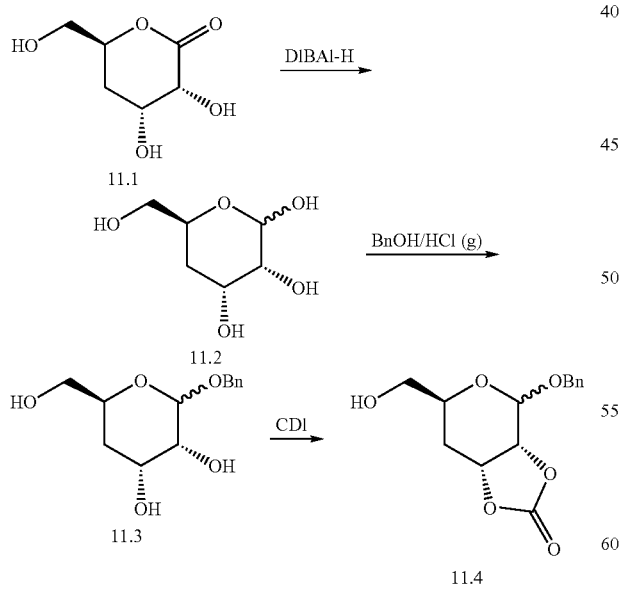

Once the benzyl protected pyranose derivatives are prepared, they will undergo hydrogenolysis to afford the hemi-acetal. Treatment of the lactol with trichloroacetonitrile will furnish the corresponding trichloroacetimidate for subsequent coupling with the requisite coumarin/coumarin analogue. The procedure outlined herein illustrates the success of coupling such compounds with the coumarin phenol and this procedure will be used to prepare the corresponding analogues as described herein.

Using the foregoing schemes, the syntheses of eight protected pyranose analogues that include mono- and dihydroxylated variants of both ring-expanded and ring contracted analogues. All eight of these compounds were orthogonally protected, such that the hemi-acetal could be coupled directly to the coumarin phenol as used similarly for the construction of A4. Subsequent removal of the protecting group(s) or treatment of the cyclic carbonate with ammonia, will afford the corresponding diol or carbamate products as demonstrated earlier.

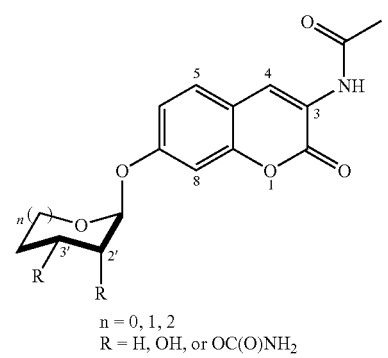

$n = 0, 1, 2$
$R = H, OH, or OC(O)NH_2$

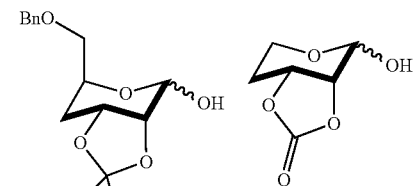

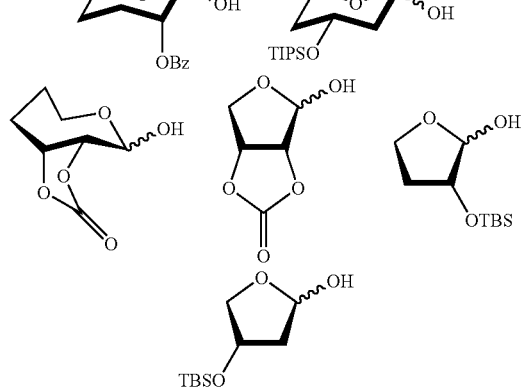

Prophetic Example 12

Preparation of 3-Dyhydroxy and 5-Desmethyoyl Analogues

In this example, the 4-deshydroxy and 8-desmethyl variants of novobiocin will be prepared along with the 8-methyl and 4-hydroxy analogues of KU-2/A3 (3'carbamate) as shown below. Not only will the 3'-carbamoyl derivatives of these compounds be prepared, but also the corresponding diols for direct comparison to KU-1/A4 (diol).

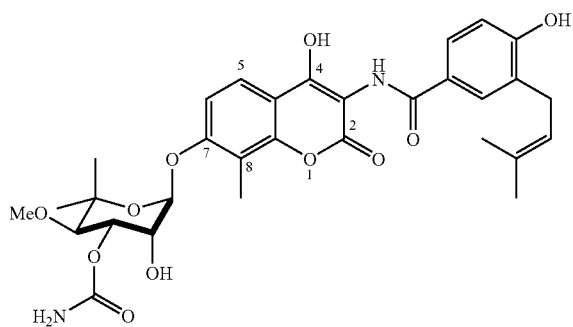

Novobiocin
700 μM inhibitor

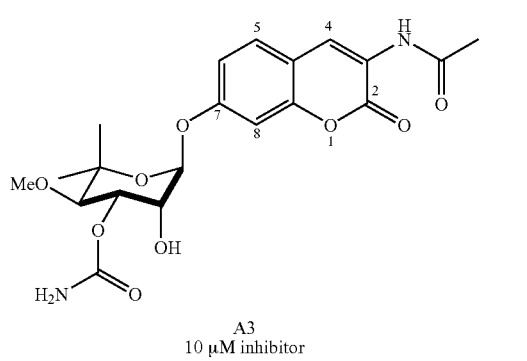

A3
10 μM inhibitor

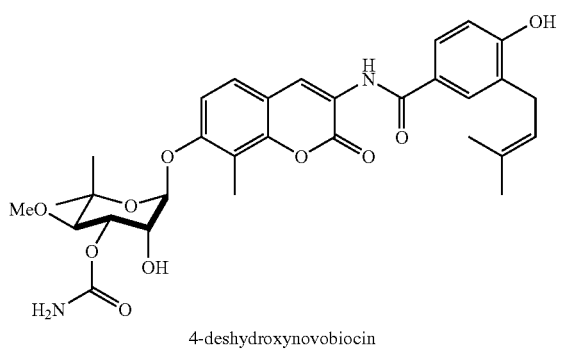

4-deshydroxynovobiocin

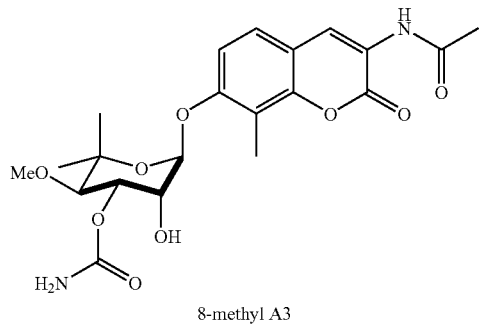

8-methyl A3

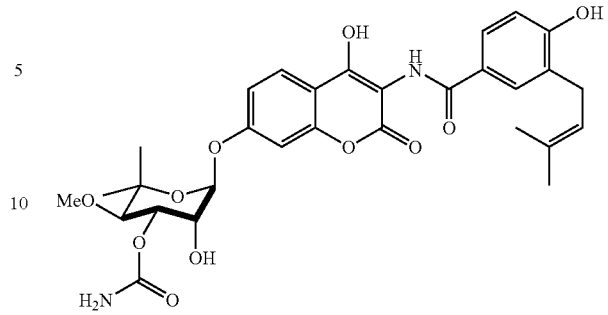

8-desmethylnovobiocin

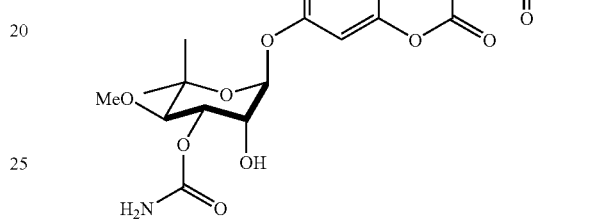

4-hydroxy A3

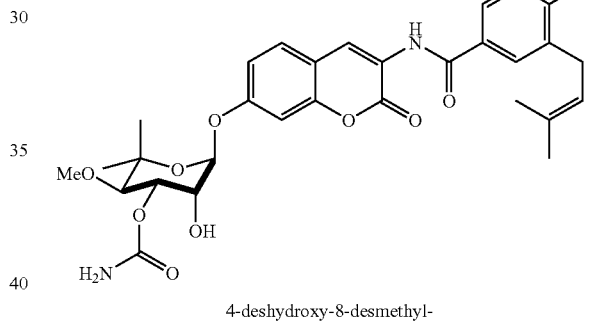

4-deshydroxy-8-desmethyl-novobiocin

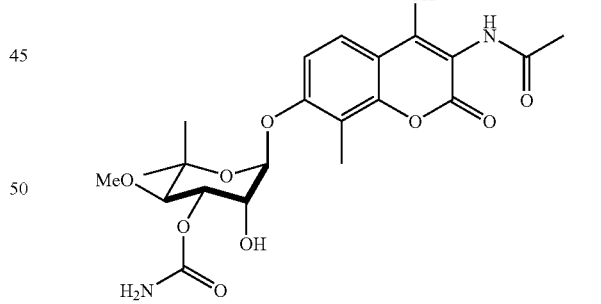

4-hydroxy-8-methyl A3

More specifically, 4-deshydroxynovobiocin will be prepared from 3-N-acetyl-7-hydroxy-8-methyl coumarin and the known carboxylic acid as set forth in the scheme below. Spencer et al., Novobiocin. IV. Synthesis of Dihydronovobiocic Acid and Cyclonovobiocic Acid, *J. Am. Chem. Soc.* 1956, 78, 2655-2656. Coupling of these two substrates will provide the amide, which will be treated with noviose carbonate in analogous fashion to other reported syntheses of novobiocin. See Vaterlaus et al., Die Synthese des Novobiocins, *Experientia* 1963, 19, 383-391; Vaterlaus et al., Novobiocin III Die Glykosidsynthese des Novobiocins, *Helv. Chim. Acta* 1964, 47, 390-398. Likewise, 8-desmethyl-novobiocin will be prepared from 4,7-dihydroxycoumarin and the diazonium salt to afford the masked amino group similar to our syntheses of photolabile derivatives. See Shen et al., Synthesis of Photolabile Novobiocin Analogues, *Bioorg. Med. Chem. Lett.* 2004, 14, 5903-5906.

The 7-hydroxyl will undergo selective noviosylation and the diazine will be reduced. The corresponding amine will be coupled with the known carboxylic acid and the carbonate opened with methanolic ammonia to give both 3-carbamoyl and diol derivatives. 4-Deshydroxy-8-desmethylnovobiocin will be constructed from 3-amino-7-hydroxycoumarin in analogous fashion as depicted in the scheme below. The KU-1/A4 and KU-2/A3 analogues incorporating the same coumarin functionalities will be prepared by an identical method (see Khoo, Synthesis of Substituted 3-Aminocoumarins from Ethyl N-2-Hydroxyarylideneglycinates, *Syn. Comm.* 1999, 29, 2533-2538) using acetic anhydride in lieu of the prenylated 4-hydroxybenzoic acid. Des(carbamoyl) derivatives of these compounds will also be prepared by removal of the cyclic carbonate with triethylamine in methanol, which affords similar products in stoichiometric yields.

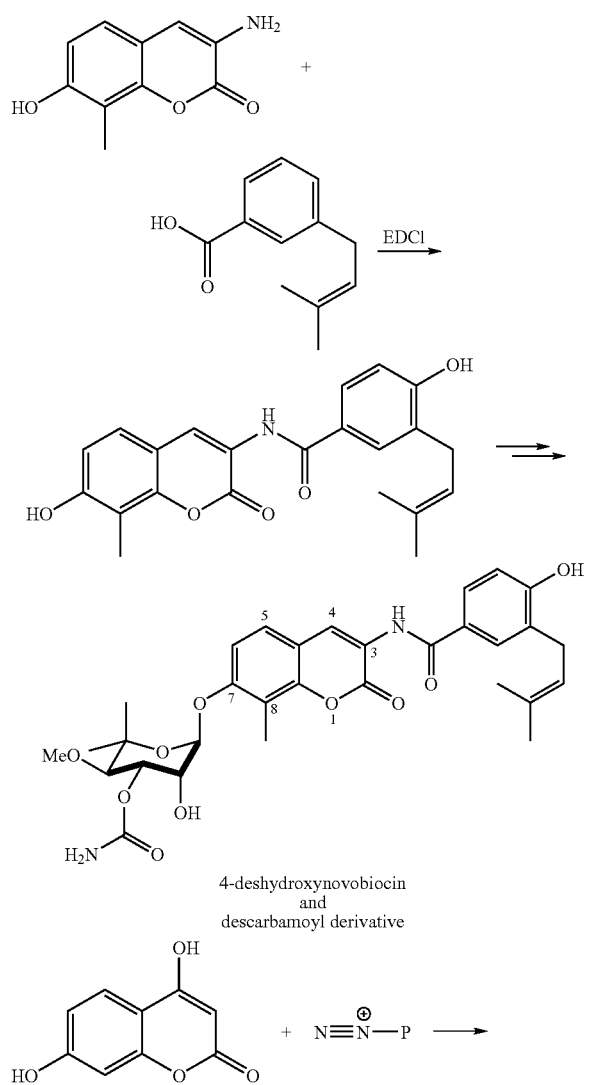

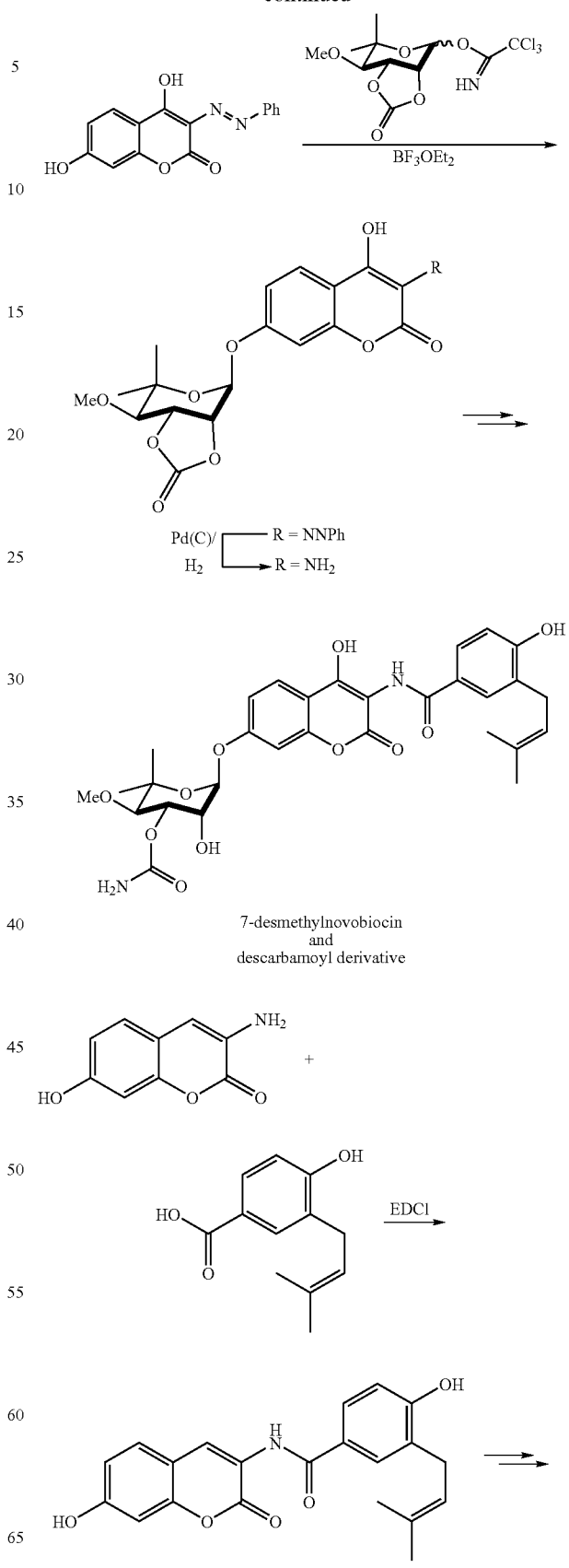

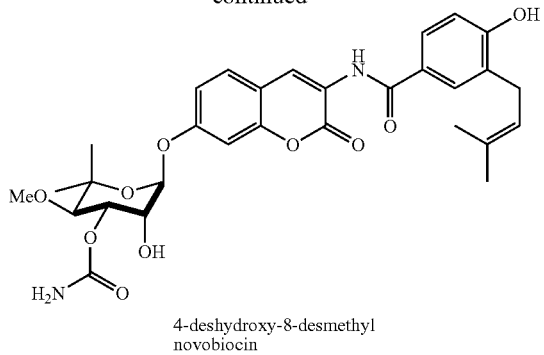

4-deshydroxy-8-desmethyl novobiocin

Prophetic Example 13

Preparation of Dimers

It is contemplated that the C-terminal nucleotide binding sites are in close proximity to the one another along the Hsp90 dimer interface, and therefore dimeric inhibitors of the compounds of the present invention should provide compounds with enhanced inhibitory activity. This is based on the fact that the dimeric compound, coumermycin A1, was shown to be approximately 10 times more active than the monomeric compound, novobiocin.

The present invention thus includes dimers of the compounds disclosed herein. In one aspect, a dimeric inhibitor of KU-1/A4 will be prepared. As set forth in the scheme below, the Cbz group will be removed to furnish the aniline for subsequent coupling with bifunctional linkers to prepare dimeric inhibitors. The dimer containing pyrazole linker found in Coumermycin A1 will be prepared following the procedure developed by Olson et al., Tetrahedron Letters (2002), Volume Date 2003, 44(1), 61-63. The diacid will be coupled with two equivalents of the coumarin amine using O-(7-azabenzotriazol-1-yl)-N,N,N',N'-tetramethyluronium hexafluorophosphate (HATU) to furnish the cyclic carbonate precursor to the KU-1/A4 dimer. The carbonate will be removed upon treatment with methanolic triethylamine to provide the tetraol product. See Yu et al. Hsp90 Inhibitors Identified from a Library of Novobiocin Analogues. *J. Am. Chem. Soc.* 127: 12778-12779 (2005). Similar to this method, a number of dimeric linkers will be used to perturb the dimeric angle and to extend the dimeric tether in an effort to elucidate structure-activity relationships. As such, ortho, meta, and para dibenzoic acids will be used in lieu of the pyrrole biscarboxylic acid to determine optimal angles. Linker length will be probed by the use of about 3-10 carbon dicarboxylic acids. If the studies support that both angle and linker length are important, then combinations of these linkers will be prepared and coupled to furnish the conformationally biased, extended compounds such as that shown below.

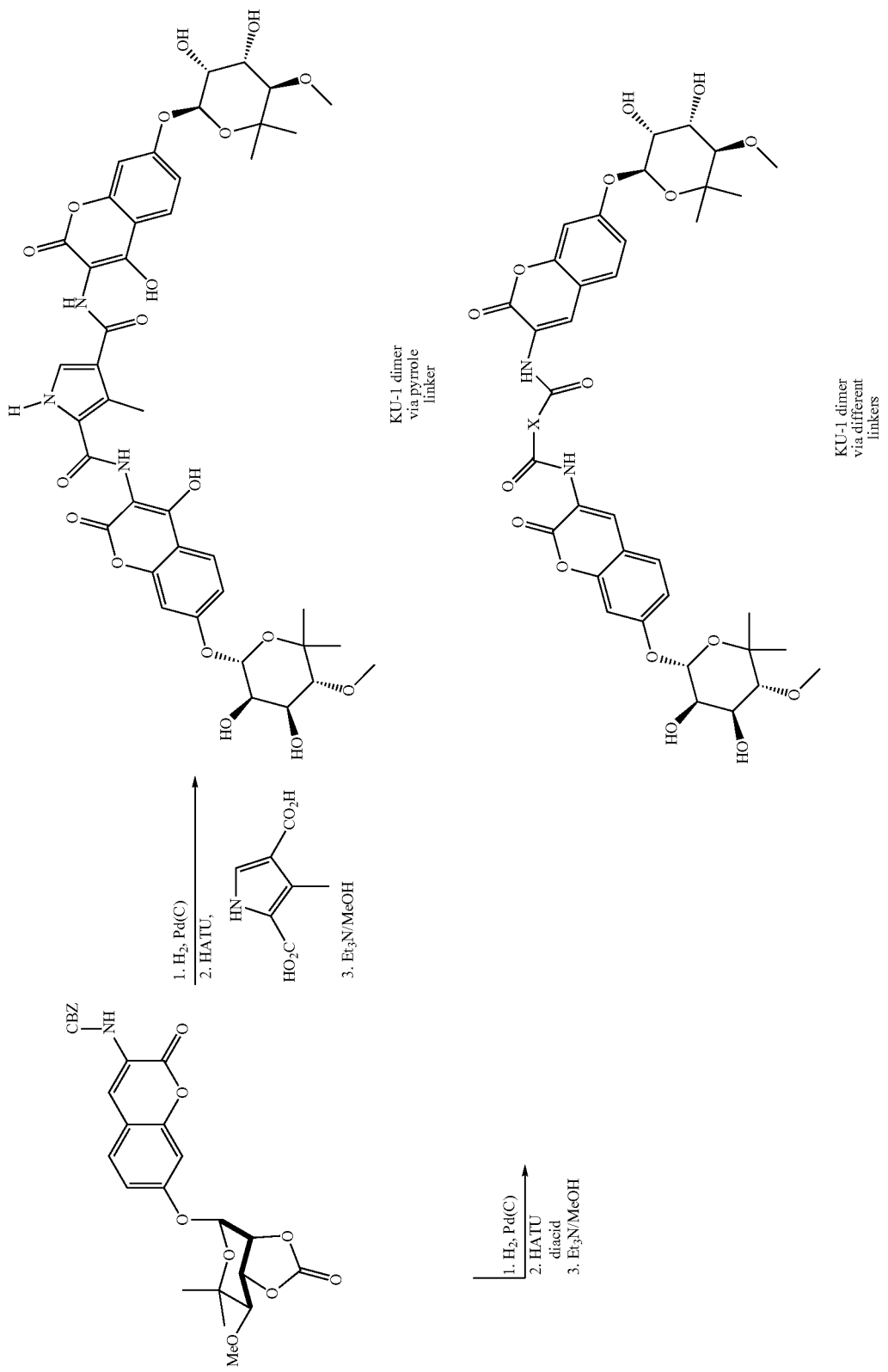

-continued
Potential diacids to be prepared if SAR support 
Diacids with varying chain lengths 
n = 0, 1-8
Diacids with varying angles of projection 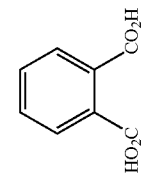 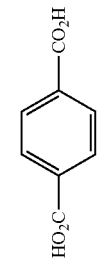

Prophetic Example 14

Prostate Cancer Xenograft Tumor Model

This example involves the in vivo effect of the compounds of the present invention using a prostate cancer mouse model. More specifically, four to six week old BALB/c nu/nu nude mice will be obtained commercially and maintained in ventilated cages under Institutional Animal Care and Use Committee approval. Separate male mice will be inoculated subcutaneously with $10^6$ LNCaP cells suspended in 0.25 mL of Matrigel (BD, Bioscience, Bedford Mass.). Stable serum testosterone levels will be maintained in the mice by the implantation of 12.5 mg 90-day sustained release testosterone pellets (Innovative Research, Sarasota Fla.) subcutaneously prior to inoculation with tumor. Tumor volume will be measured twice a week with vernier calipers with tumor volumes calculated using the formula [length×width×height×0.52]. Mice with established tumor volumes of 5 mm will be selected for KU-1/A4 administration. Utilizing the paradigm for administration of 17-AAG (another Hsp90 inhibitor), animals will be treated with both continuous and intermittent dosing schedules. A control animal will be treated with vehicle alone (DMSO). For the continuous dosing schedule, mice will receive intraperitoneal injections of vehicle or the test compounds (e.g., KU-1/A4) for 5 days per week for 3 weeks. The intermittent group will receive one 5 day cycle and then monitored for progression.

Differing doses of the test compound (e.g., KU-1/A4) will be utilized based on pharmacokinetic information obtained from toxicity studies. When progression occurs, as defined by an increase in tumor size, the mice will receive a second 5 day cycle of the test compound (e.g., KU-1/A4). Response to the test compound will be assessed by measuring tumor volume and serum PSA levels using the PSA Assay Kit (American Qualex Antibodies, San Clemente, Calif.). Further response will be assessed by harvesting the tumor at euthanasia and performing immunohistochemistry and western blot analysis of the Hsp90's client proteins known to be involved in cancer cell survival mechanisms such as signal transduction (e.g., AKT, Her2, PI3kinase), angiogenesis (e.g., HIF-1α), and metastasis (AR, MMP2). Each dose and control will be repeated three times to confirm results.

Statistical analysis will be performed to compare the average tumor volume over time between the different doses of the test compound and the control animals. The null hypothesis which is that KU-1/A4 will cause no change in tumor volume over time will be tested by the squared difference between mean tumor volume summed over all time points. We will use a Wilcoxon sum-rank test to compare PSA levels in the treatment and control group. Immunohistochemistry results will be assessed qualitatively based on staining intensity graded on a scale of 1 to 5.

To investigate toxicity, four to six week old BALB/c nu/nu nude mice will be obtained commercially and maintained in ventilated cages under Institutional Animal Care and Use Committee approval. Intraperitoneal injections of the test compound (e.g., KU-1/A4) will be given to non-tumor bearing mice at ranges of 25 mg/kg to 200 mg/kg 5 days a week for 3 weeks based on similar concentrations used for 17AAG.[12] Serum samples will be obtained on days 5, 10, and 15. Serum chemistry and liver function analysis will be performed. Serum concentrations of test compound (e.g., KU-1/A4) will be determined by high performance liquid chromatography (HPLC). At sacrifice by $CO_2$ euthanasia, a complete blood count, gross necropsy and liver and kidney histopathology will be performed on the animals to determine toxicity. The maximal tolerated dose will be calculated using up/down toxicity studies that will be used as the upper limit of dose for treatment.

Example 15

Neuroprotective Effects

Recently, low concentrations of the Hsp90 inhibitor GDA were reported to induce expression of both Hsp70 and Hsp90, with a concomitant reduction in phosphorylated Tau (Dou et al., 2003). In this example, KU-1/A4, a novel C-terminal Hsp90 inhibitor, was tested for protective effects against Aβ toxicity in primary neurons. See protocols in Michaelis M L, Ansar S, Chen Y, Reiff E R, Seyb K I, Himes R H, Audus K L, Georg G I (2005) B-Amyloidinduced neurodegeneration and protection by structurally diverse microtubule-stabilizing agents. J Pharmacol Exp Ther 312:659-668, which is incorporated by reference.

Figure 4:
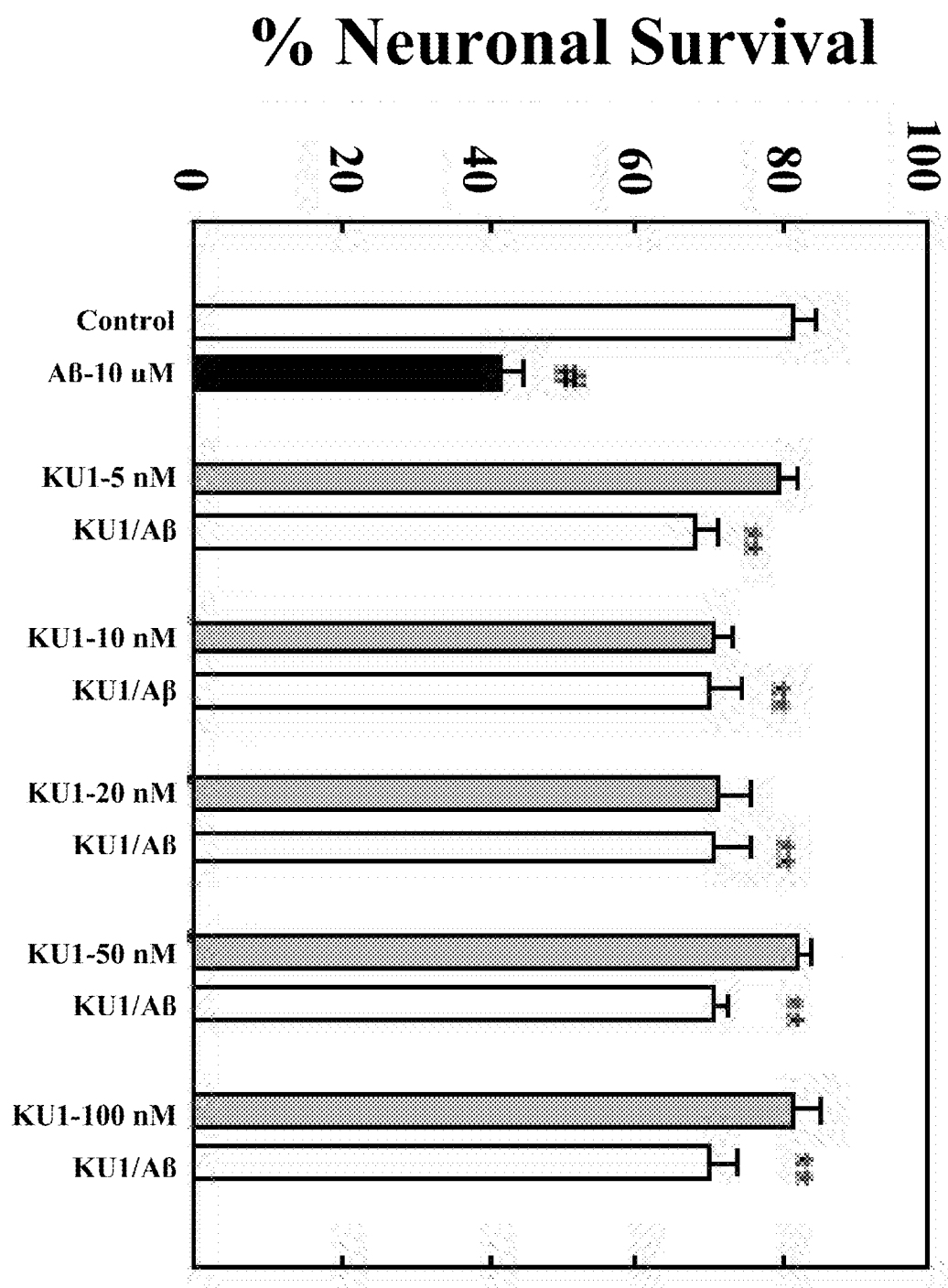
FIG. 4 shows the dose dependent effects of KU-1/A4 on Aβ-induced cell death in primary neurons. The compound was added two hours before the βA and the viability was determined at 48 hours. The data represents standard error of the means ("S.E.M.") from about 1500 cells from 3 preparations. #, $p<0.0001$ for control vs. Aβ only. **, $p<0.001$. Aβ only vs. Aβ+KU-1/A4.

As is shown in FIG. 4, concentrations of KU-1/A4 as low as 5 nM protected the neurons against Aβ, and the drug alone produced no toxicity. GDA partially protect the neurons against Aβ, but the drug alone was toxic to the neurons at concentrations above 20 nM. Thus, although GDA can increase Hsp90 levels, the result may be the degradation of client proteins essential for neuronal survival. This lack of KU1 toxicity in both proliferating and post-mitotic cells suggested that further exploration of its mechanism(s) of action is warranted.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth are to be interpreted as illustrative, and not in a limiting sense. Further, it will be understood that certain features and subcombinations are of utility and may be employed without reference to other features and subcombinations. This is contemplated by and is within the scope of the claims.

The invention claimed is:
1. A compound according to Formula I

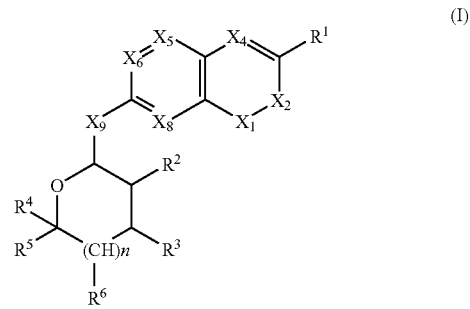

wherein $R^1$ is hydrogen, alkyl, aryl or amido;
wherein $R^2$ is hydrogen; hydroxy or —$R^8$—$OR^9$, wherein $R^8$ is a covalent bond or alkyl, and $R^9$ is C-amido or acyl; or $R^2$ together with $R^3$ and the atoms to which they are attached form a heterocyclic ring having 4 to 8 ring members with at least one heteroatom selected from oxygen or nitrogen;
wherein $R^3$ is hydrogen; hydroxy or —$R^{10}$—$OR^{11}$, wherein $R^{10}$ is a covalent bond or alkyl, and $R^{11}$ is C-amido or acyl; or R³ together with R² and the atoms to which they are attached form a heterocyclic ring having 4 to 8 ring members with at least one heteroatom selected from oxygen or nitrogen;

wherein R⁴ is hydrogen or methyl;
wherein R⁵ is hydrogen or alkyl;
wherein R⁶ is hydrogen, alkyl, alkenyl, alkynyl, aryl, aralkyl, alkoxy, aryloxy, or aralkoxy;
wherein $X_1$ is —O—, —CO—, or —N—;
wherein $X_2$ is —O—, —N—, —NR¹⁸—, —CR¹⁹—, or —CO—;
wherein R¹⁸ and R¹⁹ are hydrogen, alkyl, alkenyl, or alkynyl;
wherein $X_4$ is —CR²⁰—, wherein R²⁰ is hydrogen, alkyl, alkenyl, or alkynyl;
wherein $X_5$ is —CR²¹—, wherein R²¹ is hydrogen, alkyl, alkenyl, or alkynyl;
wherein $X_6$ is —CR²²—, wherein R²² is hydrogen, alkyl, alkenyl, alkynyl, alkoxy, aryl, aralkyl, halogen, or nitro;
wherein $X_8$ is —CR²³— or —N—, wherein R²³ is hydrogen, alkyl, alkenyl, or alkynyl;
wherein $X_9$ is ether;
and wherein at least one of $X_1$, $X_2$, $X_4$, $X_5$, $X_6$, $X_8$ is not —CR—;
wherein n is 1; and
wherein R² and R³ are not simultaneously hydroxy.

2. The coumarin compound of claim 1 wherein $X_1$ is —O— and $X_2$ is —CO—.

3. The isocoumarin compound of claim 1 wherein $X_1$ is —CO— and $X_2$ is —O—.

4. The compound of claim 2 wherein R⁴ and R⁵ are both methyl.

5. The compound of claim 2 wherein $X_4$ is —CR²⁰— and R²⁰ is hydrogen, and wherein $X_8$ is —CR²³— and R²³ is hydrogen or alkyl.

6. The compound of claim 5 wherein R¹ is amido.

7. The compound of claim 6 selected from the group consisting of:

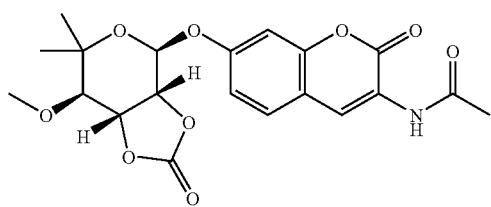

N-(7-((3aR,4R,7R,7aR)-7-methoxy-6,6-dimethyl-2-oxo-tetrahydro-3aH-[1,3]dioxolo[4,5-c]pyran-4-yloxy)-2-oxo-2H-chromen-3-yl)acetamide (A1);

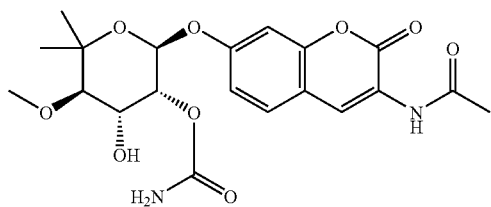

(2R,3R,4R,5R)-2-(3-acetamido-2-oxo-2H-chromen-7-yloxy)-4-hydroxy-5-methoxy-6,6-dimethyl-tetrahydro-2H-pyran-3-yl carbamate (A2);

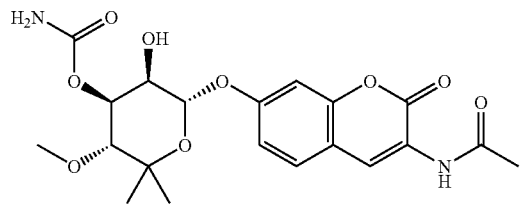

(3R,4S,5R,6R)-6-(3-acetamido-2-oxo-2H-chromen-7-yloxy)-5-hydroxy-3-methoxy-2,2-dimethyl tetrahydro-2H-pyran-4-yl carbamate (A3); and

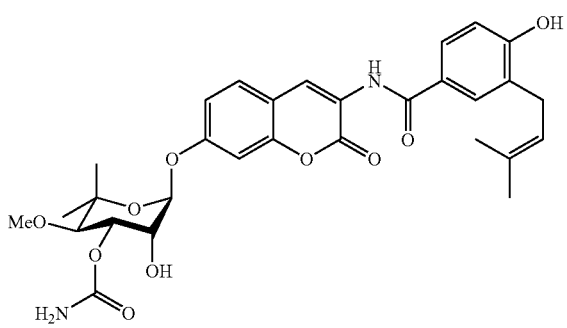

4-deshydroxy-8-desmethylnovobiocin.

8. The compound of claim 5 wherein R¹ is hydrogen.

9. The compound of claim 8 selected from the group consisting of:

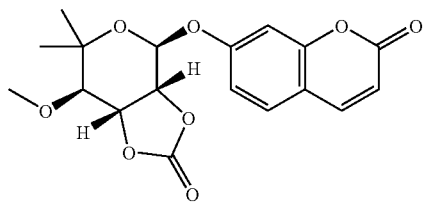

7-((3aR,4R,7R,7aR)-7-methoxy-6,6-dimethyl-2-oxo-tetrahydro-3 aH-[1,3]dioxolo[4,5-c]pyran-4-yloxy)-2H-chromen-2-one (B1);

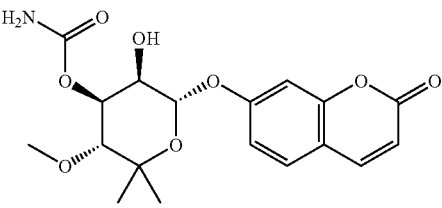

(3R,4S,5R,6R)-5-hydroxy-3-methoxy-2,2-dimethyl-6-(2-oxo-2H-chromen-7-yloxy)-tetrahydro-2H-pyran-4-yl carbamate (B2);

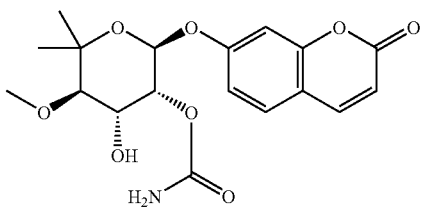

(2R,3R,4R,5R)-4-hydroxy-5-methoxy-6,6-dimethyl-2-(2-oxo-2H-chromen-7-yloxy)-tetrahydro-2H-pyran-3-yl carbamate (B3).

10. The compound of claim 2 wherein $X_4$, is —$CR^{20}$— and $R^{20}$ is alkyl and wherein $R^1$ is aryl.

11. The compound of claim 10 selected from the group consisting of:

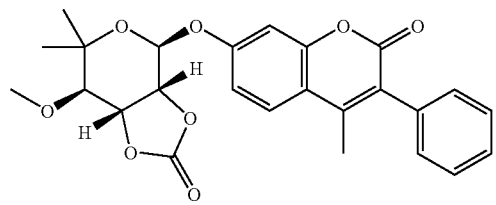

7-((3aR,4R,7R,7aR)-7-methoxy-6,6-dimethyl-2-oxo-tetrahydro-3 aH-[1,3]dioxolo[4,5-c]pyran-4-yloxy)-4-methyl-3-phenyl-2H-chromen-2-one (C1);

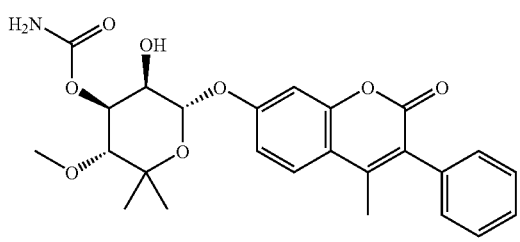

(3R,4S,5R,6R)-5-hydroxy-3-methoxy-2,2-dimethyl-6-(4-methyl-2-oxo-3-phenyl-2H-chromen-7-yloxy)-tetrahydro-2H-pyran-4-yl carbamate (C2); and

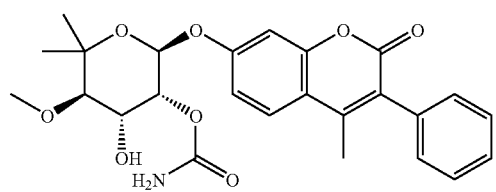

(2R,3R,4R,5R)-4-hydroxy-5-methoxy-6,6-dimethyl-2-(4-methyl-2-oxo-3-phenyl-2H-chromen-7-yloxy)-tetrahydro-2H-pyran-3-yl carbamate (C3).

12. The compound of claim 2 wherein $X_4$ is —$CR^{20}$— and $R^{20}$ is hydrogen, and wherein $X_8$ is —$CR^{23}$— and $R^{23}$ is alkyl.

13. The compound of claim 12 wherein $R^1$ is amido.

14. The compound of claim 13 selected from the group consisting of:

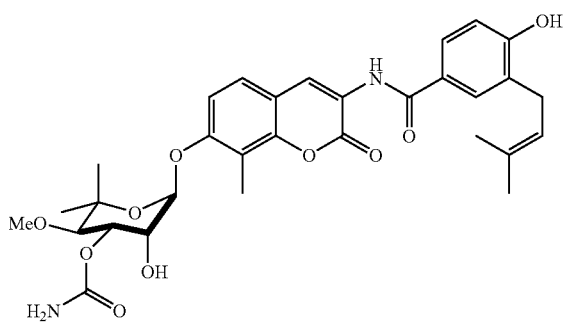

4-deshydroxynovobiocin (DHN1); and

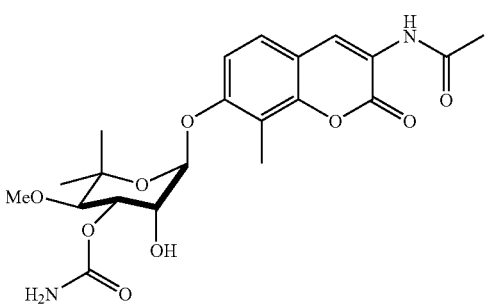

(3R,4S,5R,6R)-6-(3-acetamido-2-oxo-2H-chromen-7-yloxy)-8-methyl-5-hydroxy-3-methoxy-2,2-dimethyltetrahydro-2H-pyran-4-yl carbamate (8-methyl A3).

15. A compound according to Formula II:

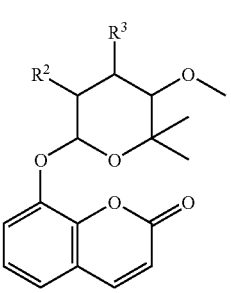

(II)

wherein $R^2$ is hydrogen; hydroxy or —$R^8$—$OR^9$, wherein $R^8$ is a covalent bond or alkyl, and $R^9$ is C-amido or acyl; or $R^2$ together with $R^3$ and the atoms to which they are attached form a heterocyclic ring having 4 to 8 ring members with at least one heteroatom selected from oxygen or nitrogen; and wherein $R^3$ is hydrogen; hydroxyl or —$R^{10}$—$OR^{11}$, wherein $R^{10}$ is a covalent bond or alkyl, and $R^{11}$ is C-amido or acyl; or $R^3$ together with $R^2$ and the atoms to which they are attached form a heterocyclic ring having 4 to 8 ring members with at least one heteroatom selected from oxygen or nitrogen.

16. The compound of claim 15 selected from the group consisting of:

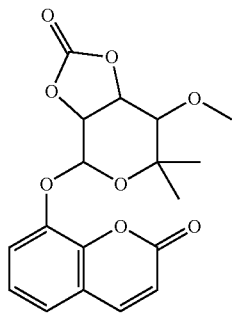

8-(7-Methoxy-6,6-dimethyl-2-oxo-tetrahydro-[1,3]di-oxolo[4,5-c]pyran-4-yloxy)-chromen-2-one (D1);

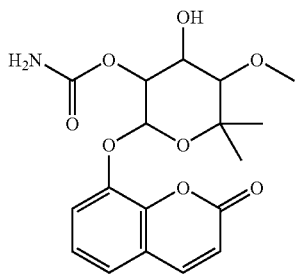

Carbamic acid 4-hydroxy-5-methoxy-6,6-dimethyl-2-(2-oxo-2H-chromen-8-yloxy)-tetrahydro-pyran-3-yl ester (D2);

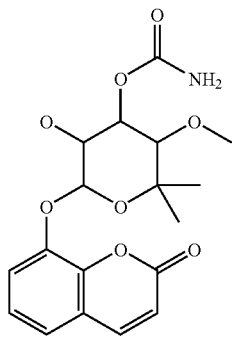

Carbamic acid 5-hydroxy-3-methoxy-2,2-dimethyl-6-(2-oxo-2H-chromen-8-yloxy)-tetrahydro-pyran-4-yl ester (D3); and

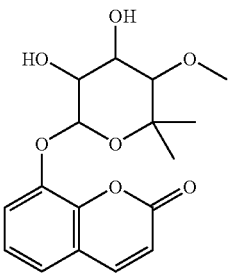

8-(3,4-Dihydroxy-5-methoxy-6,6-dimethyl-tetrahydro-pyran-2-yloxy)-chromen-2-one (D4).

17. A compound according to Formula III:

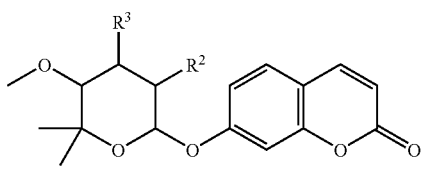

(III)

wherein $R^2$ is hydrogen; hydroxy or —$R^8$—$OR^9$, wherein $R^8$ is a covalent bond or alkyl, and $R^9$ is C-amido or acyl; or $R^2$ together with $R^3$ and the atoms to which they are attached form a heterocyclic ring having 4 to 8 ring members with at least one heteroatom selected from oxygen or nitrogen; and wherein $R^3$ is hydrogen; hydroxyl or —$R^{10}$—$OR^{11}$, wherein $R^{10}$ is a covalent bond or alkyl, and $R^{11}$ is C-amido or acyl; or $R^3$ together with $R^2$ and the atoms to which they are attached form a heterocyclic ring having 4 to 8 ring members with at least one heteroatom selected from oxygen or nitrogen.

18. The compound of claim 17 selected from the group consisting of:

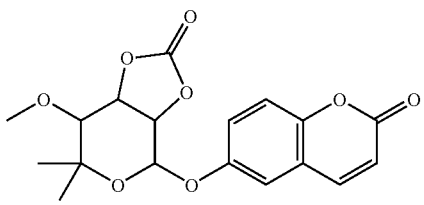

6-(7-Methoxy-6,6-dimethyl-2-oxo-tetrahydro-[1,3]di-oxolo[4,5-c]pyran-4-yloxy)-chromen-2-one [E1];

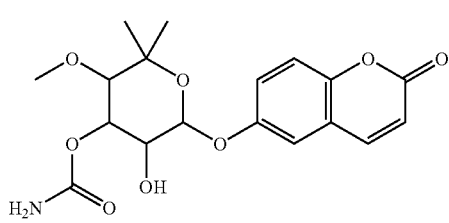

Carbamic acid 5-hydroxy-3-methoxy-2,2-dimethyl-6-(2-oxo-2H-chromen-6-yloxy)-tetrahydro-pyran-4-yl ester (E2);

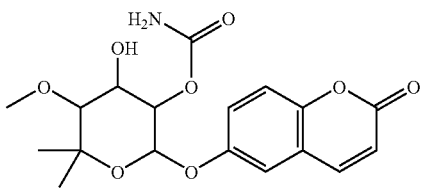
Carbamic acid 4-hydroxy-5-methoxy-6,6-dimethyl-2-(2-oxo-2H-chromen-6-yloxy)-tetrahydro-pyran-3-yl ester (E3); and
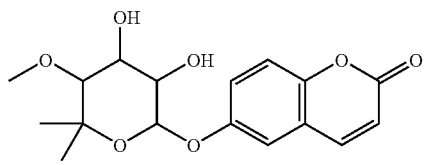
6-(3,4-Dihydroxy-5-methoxy-6,6-dimethyl-tetrahydro-pyran-2-yloxy)-chromen-2-one (E4).
* * * * *